(12) United States Patent
Kato et al.

(10) Patent No.: US 9,086,623 B2
(45) Date of Patent: Jul. 21, 2015

(54) METHOD OF FORMING PATTERN, ACTINIC-RAY- OR RADIATION-SENSITIVE RESIN COMPOSITION AND ACTINIC-RAY- OR RADIATION-SENSITIVE FILM

(75) Inventors: Keita Kato, Shizuoka (JP); Atsushi Nakamura, Shizuoka (JP)

(73) Assignee: FUJIFILM Corporation, Tokyo (JP)

( * ) Notice: Subject to any disclaimer, the term of this patent is extended or adjusted under 35 U.S.C. 154(b) by 24 days.

(21) Appl. No.: 13/598,087

(22) Filed: Aug. 29, 2012

(65) Prior Publication Data

US 2013/0049149 A1 Feb. 28, 2013

(30) Foreign Application Priority Data

Aug. 30, 2011 (JP) ................................. 2011-187055

(51) Int. Cl.

| G03F 7/004 | (2006.01) |
|---|---|
| G03F 7/20 | (2006.01) |
| G03F 7/32 | (2006.01) |
| C08F 220/10 | (2006.01) |
| C08F 212/08 | (2006.01) |
| H01L 21/027 | (2006.01) |
| H01L 21/308 | (2006.01) |
| G03F 7/039 | (2006.01) |

(52) U.S. Cl.
CPC ............ *G03F 7/0045* (2013.01); *C08F 212/08* (2013.01); *C08F 220/10* (2013.01); *G03F 7/0046* (2013.01); *G03F 7/0392* (2013.01); *G03F 7/0397* (2013.01); *G03F 7/325* (2013.01); *H01L 21/0274* (2013.01); *H01L 21/3081* (2013.01); *C07C 2102/14* (2013.01); *C07C 2103/56* (2013.01); *C07C 2103/74* (2013.01); *Y10S 430/114* (2013.01)

(58) Field of Classification Search
CPC ....... G03F 7/004; G03F 7/397; G03F 7/2041; G03F 7/0045; G03F 7/0046; G03F 7/0392; G03F 7/32; C08F 220/10; C08F 212/08; Y10S 430/114; C07C 2103/56; C07C 2103/74; C07C 2102/14; H01L 21/0274; H01L 21/3081
USPC ............... 430/270.1, 434, 435, 905, 913, 914
See application file for complete search history.

(56) References Cited

U.S. PATENT DOCUMENTS

| 6,114,082 | A | 9/2000 | Hakey et al. | |
|---|---|---|---|---|
| 7,214,467 | B2 * | 5/2007 | Kanna et al. | 430/270.1 |
| 8,017,298 | B2 * | 9/2011 | Tsubaki | 430/270.1 |
| 8,227,183 | B2 * | 7/2012 | Tsubaki et al. | 430/434 |
| 8,546,063 | B2 * | 10/2013 | Tsubaki et al. | 430/296 |
| 8,632,942 | B2 * | 1/2014 | Tsubaki | 430/270.1 |
| 2001/0049073 | A1 | 12/2001 | Hada et al. | |
| 2005/0065312 | A1 | 3/2005 | Hada et al. | |
| 2006/0121390 | A1 * | 6/2006 | Gonsalves | 430/270.1 |
| 2008/0187860 | A1 | 8/2008 | Tsubaki et al. | |
| 2008/0261150 | A1 * | 10/2008 | Tsubaki et al. | 430/270.1 |
| 2009/0011366 | A1 | 1/2009 | Tsubaki et al. | |
| 2009/0142693 | A1 | 6/2009 | Iwashita | |
| 2010/0330507 | A1 | 12/2010 | Tsubaki et al. | |
| 2011/0177462 | A1 | 7/2011 | Hatakeyama et al. | |
| 2011/0244392 | A1 * | 10/2011 | Hirano et al. | 430/270.1 |
| 2011/0300485 | A1 | 12/2011 | Tsubaki et al. | |
| 2012/0058436 | A1 | 3/2012 | Tsubaki et al. | |
| 2012/0135355 | A1 * | 5/2012 | Tsubaki | 430/311 |
| 2013/0022911 | A1 * | 1/2013 | Utsumi et al. | 430/270.1 |
| 2013/0344441 | A1 * | 12/2013 | Sooriyakumaran et al. | 430/285.1 |

FOREIGN PATENT DOCUMENTS

| JP | 6-35195 A | 2/1994 |
|---|---|---|
| JP | 6-80724 A | 3/1994 |
| JP | 10-104834 A | 4/1998 |
| JP | 2000-206694 A | 7/2000 |
| JP | 2006-195050 A | 7/2006 |
| JP | 2006-259582 A | 9/2006 |
| JP | 2006-317803 A | 11/2006 |
| JP | 2007-025534 A | 2/2007 |
| JP | 2008-281974 A | 11/2008 |
| JP | 2008-281975 A | 11/2008 |
| JP | 2008-292975 A | 12/2008 |
| JP | 2010-24330 A | 2/2010 |
| JP | 2010-077038 A | 4/2010 |
| JP | 2010-176089 A | 8/2010 |
| JP | 2010-217884 A | 9/2010 |
| JP | 2011-170316 A | 9/2011 |
| WO | 2009/143357 A2 | 11/2009 |

OTHER PUBLICATIONS

Japanese Office Action dated Jul. 9, 2013 issued in Japanese Patent Application No. 2011-187055.
Japanese Office Action dated May 20, 2014 issued in corresponding application No. 2011-187055.

* cited by examiner

*Primary Examiner* — Amanda C Walke
(74) *Attorney, Agent, or Firm* — Sughrue Mion, PLLC

(57) ABSTRACT

Provided is a method of forming a pattern, including forming an actinic-ray- or radiation-sensitive resin composition into a film, the actinic-ray- or radiation-sensitive resin composition including a resin (A) including a repeating unit containing a group that when acted on by an acid, is decomposed to thereby produce a polar group and including an aromatic group, which resin when acted on by an acid, decreases its solubility in an organic solvent, a nonionic compound (B) that when exposed to actinic rays or radiation, generates an acid and a solvent (C), exposing the film to actinic rays or radiation, and developing the exposed film with a developer including an organic solvent to thereby form a negative pattern.

18 Claims, No Drawings

METHOD OF FORMING PATTERN, ACTINIC-RAY- OR RADIATION-SENSITIVE RESIN COMPOSITION AND ACTINIC-RAY- OR RADIATION-SENSITIVE FILM

CROSS-REFERENCE TO RELATED APPLICATIONS

This application is based upon and claims the benefit of priority from Japanese Patent Application No. 2011-187055, filed Aug. 30, 2011, the entire contents of which are incorporated herein by reference.

BACKGROUND OF THE INVENTION

1. Field of the Invention

The present invention relates to a method of forming a pattern that is suitable for use in, for example, a semiconductor production process for an IC or the like, a circuit board production process for a liquid crystal, a thermal head or the like and other photofabrication lithography processes, and relates to an actinic-ray- or radiation-sensitive resin composition for use in the pattern forming method and an actinic-ray- or radiation-sensitive film. More particularly, the present invention relates to a method of forming a pattern that is suitable for the exposure to light by means of a KrF exposure apparatus, an electron beam exposure apparatus or an EUV exposure apparatus, and relates to an actinic-ray- or radiation-sensitive resin composition for use in the pattern forming method and an actinic-ray- or radiation-sensitive film.

2. Description of the Related Art

Since the development of the resist for a KrF excimer laser (248 nm), an image forming method based on chemical amplification has been employed as a resist image forming method in order to compensate for any sensitivity decrease caused by light absorption. A positive image forming method based on chemical amplification will be described by way of example. In this image forming method, the acid generator contained in exposed areas is decomposed upon exposure to light, such as an excimer laser, electron beams or an extreme ultraviolet light, to thereby generate an acid. In the stage of the bake after the exposure (Post-Exposure Bake: PEB), the generated acid is utilized as a reaction catalyst so that alkali-insoluble groups are converted to alkali-soluble groups. Thereafter, the exposed areas are removed by an alkali developer.

For use in the above method, various alkali developers have been proposed. For example, an aqueous alkali developer containing 2.38 mass % TMAH (aqueous solution of tetramethylammonium hydroxide) is universally used.

In another aspect, not only the currently mainstream positive type but also negative chemically amplified resist compositions for use in the pattern formation by alkali development are being developed (see, for example, patent references 1 to 4). This reflects the situation in which in the production of semiconductor elements and the like, while there is a demand for the formation of patterns with various shapes, such as a line, a trench and a hole, there exist patterns whose formation is difficult with the use of current positive resists.

In recent years, also, a pattern forming method using a negative developer, namely, a developer comprising an organic solvent is being developed (see, for example, patent references 5 to 7). For example, patent reference 7 discloses a pattern forming method comprising the operations of applying onto a substrate a positive resist composition that when exposed to actinic rays or radiation, increases its solubility in a positive developer and decreases its solubility in a negative developer, exposing the applied resist composition to light and developing the exposed resist composition with a negative developer. This method realizes the stable formation of a high-precision fine pattern.

However, it has been found that the possibility of residue defect occurrence is high when the development is performed with a developer comprising an organic solvent.

Moreover, the most advanced pattern formation being developed in recent years comprises liquid-immersion exposure by means of an ArF excimer laser so as to realize the formation of a pattern of high resolution. Resins containing an aromatic ring or a double bond absorb ArF light, namely, 193 nm light, so that satisfactory transmission cannot be ensured with the use thereof. Accordingly, the resin to be incorporated in the resist composition for ArF is quite often comprised of an aliphatic compound. Therefore, designing for rendering an Onishi parameter low is difficult, and a poor etching resistance is likely to be exhibited.

PRIOR ART LITERATURE

Patent Reference

[Patent reference 1] Jpn. Pat. Appln. KOKAI Publication No. (hereinafter referred to as JP-A-) 2006-317803,
[Patent reference 2] JP-A-2006-259582,
[Patent reference 3] JP-A-2006-195050,
[Patent reference 4] JP-A-2000-206694,
[Patent reference 5] JP-A-2008-281974,
[Patent reference 6] JP-A-2008-281975, and
[Patent reference 7] JP-A-2008-292975.

BRIEF SUMMARY OF THE INVENTION

It is an object of the present invention to provide a technology that solves the above problem and that realizes the stable formation of a high-precision fine pattern being requisite for the manufacturing of highly integrated high-precision electronic devices. It is particular objects of the present invention to provide a method of forming a pattern in which a negative pattern ensuring high resolution, high etching resistance and reduced development residue defects can be formed by means of a KrF light, electron beams or an EUV light while realizing high resolution and high etching resistance, and to provide an actinic-ray- or radiation-sensitive resin composition for use in the method and an actinic-ray- or radiation-sensitive film.

Some aspects of the present invention are as follows.

[1] A method of forming a pattern, comprising; forming an actinic-ray- or radiation-sensitive resin composition into a film, the actinic-ray- or radiation-sensitive resin composition comprising;
  a resin (A) comprising a repeating unit containing a group that when acted on by an acid, is decomposed to thereby produce a polar group and comprising an aromatic group, which resin when acted on by an acid, decreases its solubility in an organic solvent,
  a nonionic compound (B) that when exposed to actinic rays or radiation, generates an acid, and
  a solvent (C);
exposing the film to actinic rays or radiation; and developing the exposed film with a developer comprising an organic solvent to thereby form a negative pattern.

[2] The method according to item [1], wherein the nonionic compound (B) is expressed by general formula (B1) or (B2) below,

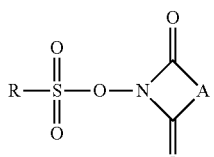

(B1)

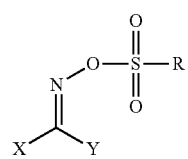

(B2)

in general formula (B1),

R represents an organic group, and

A represents an alkylene group, a cycloalkylene group, an alkenylene group, a cycloalkenylene group or an arylene group; and in general formula (B2), R represents an organic group, and each of X and Y independently represents an alkyl group, a cycloalkyl group, an aryl group, a cyano group or a nitro group, provided that X and Y may be bonded to each other to thereby form a ring, provided that X or Y of any of compounds of general formula (B2) may be bonded to X or Y of any of other compounds of general formula (B2) via a connecting group or a single bond.

[3] The method according to item [1] or [2], wherein the repeating unit containing a group that when acted on by an acid, is decomposed to thereby produce a polar group, contained in the resin (A) is expressed by general formula (I) below,

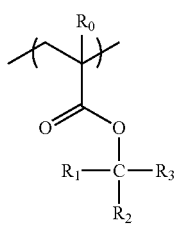

(I)

in which $R_0$ represents a hydrogen atom or a linear or branched alkyl group optionally substituted with a fluorine atom or a hydroxyl group, and each of $R_1$, $R_2$ and $R_3$ independently represents an optionally substituted linear or branched alkyl group or an optionally substituted cycloalkyl group, provided that any two of $R_1$, $R_2$ and $R_3$ may be bonded to each other to thereby form a monocyclic or polycyclic structure.

[4] The method according to any of items [1] to [3], wherein a repeating unit containing the aromatic group contained in the resin (A) is expressed by general formula (II) below,

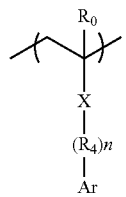

(II)

in which $R_0$ represents a hydrogen atom or a linear or branched alkyl group optionally substituted with a fluorine atom or a hydroxyl group, X represents a single bond or a bivalent connecting group, Ar represents an optionally substituted aromatic group, provided that when a substituent is introduced in the aromatic group, the substituent is any of an alkyl group (optionally substituted), a cycloalkyl group (optionally substituted), an aryl group, a halogen atom, a cyano group, an amino group, a nitro group and a carboxyl group, $R_4$ represents an optionally substituted alkylene group, and n is an integer of 0 to 4.

[5] The method according to item [4], wherein in general formula (II), X is —COO— or —CONH—.

[6] The method according to any of items [1] to [5], wherein any of repeating units of general formula (III) below is contained in the resin (A) in an amount of up to 20 mol % based on all the repeating units of the resin (A),

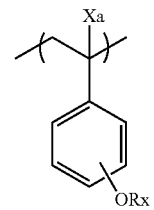

(III)

in which

Xa represents a hydrogen atom or a linear or branched alkyl group, and

Rx represents a hydrogen atom or a group that when acted on by an acid, is decomposed to thereby be cleaved.

[7] The method according to any of items [1] to [6], wherein the resin (A) contains neither any aromatic group containing a phenolic hydroxyl group nor any aromatic group containing a phenolic hydroxyl group whose hydrogen atom is replaced by a group that when acted on by an acid, is decomposed to thereby be cleaved.

[8] The method according to any of items [1] to [7], wherein the developer is a developer comprising at least one organic solvent selected from among a ketone solvent, an ester solvent, an alcohol solvent, an amide solvent and an ether solvent.

[9] An actinic-ray- or radiation-sensitive resin composition for use in the method according to any of items [1] to [8].

[10] The actinic-ray- or radiation-sensitive resin composition according to item [9], comprising a resin (A) comprising a repeating unit containing a group that when acted on by an acid, is decomposed to thereby produce a polar group and comprising an aromatic group, which resin when acted on by an acid, decreases its solubility in an organic solvent, a nonionic compound (B) that when exposed to actinic rays or radiation, generates an acid and a solvent (C).

[11] The actinic-ray- or radiation-sensitive resin composition according to item [9] or [10], wherein the nonionic compound (B) is expressed by general formula (B1) or (B2) below,

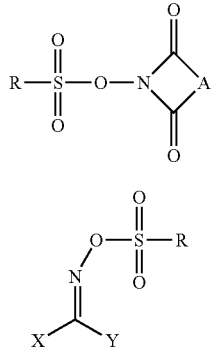

in general formula (B1),
R represents an organic group, and
A represents an alkylene group, a cycloalkylene group, an alkenylene group, a cycloalkenylene group or an arylene group; and
in general formula (B2),
R represents an organic group, and
each of X and Y independently represents an alkyl group, a cycloalkyl group, an aryl group, a cyano group or a nitro group, provided that X and Y may be bonded to each other to thereby form a ring,
provided that X or Y of any of compounds of general formula (B2) may be bonded to X or Y of any of other compounds of general formula (B2) via a connecting group or a single bond.

[12] The actinic-ray- or radiation-sensitive resin composition according to any of items [9] to [11], wherein the repeating unit containing a group that when acted on by an acid, is decomposed to thereby produce a polar group, contained in the resin (A) is expressed by general formula (I) below,

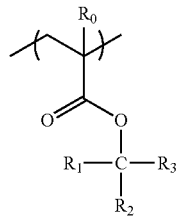

in which
$R_0$ represents a hydrogen atom or a linear or branched alkyl group optionally substituted with a fluorine atom or a hydroxyl group, and
each of $R_1$, $R_2$ and $R_3$ independently represents an optionally substituted linear or branched alkyl group or an optionally substituted cycloalkyl group, provided that any two of $R_1$, $R_2$ and $R_3$ may be bonded to each other to thereby form a monocyclic or polycyclic structure.

[13] The actinic-ray- or radiation-sensitive resin composition according to any of items [9] to [12], wherein a repeating unit containing the aromatic group contained in the resin (A) is expressed by general formula (II) below,

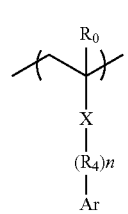

in which
$R_0$ represents a hydrogen atom or a linear or branched alkyl group optionally substituted with a fluorine atom or a hydroxyl group,
X represents a single bond or a bivalent connecting group,
Ar represents an optionally substituted aromatic group, provided that when a substituent is introduced in the aromatic group, the substituent is any of an alkyl group (optionally substituted), a cycloalkyl group (optionally substituted), an aryl group, a halogen atom, a cyano group, an amino group, a nitro group and a carboxyl group,
$R_4$ represents an optionally substituted alkylene group, and
n is an integer of 0 to 4.

[14] The actinic-ray- or radiation-sensitive resin composition according to item [13], wherein in general formula (II), X is —COO— or —CONH—.

[15] The actinic-ray- or radiation-sensitive resin composition according to any of items [9] to [14], wherein the content of any of repeating units of general formula (III) below contained in the resin (A) is up to 20 mol % based on all the repeating units of the resin (A),

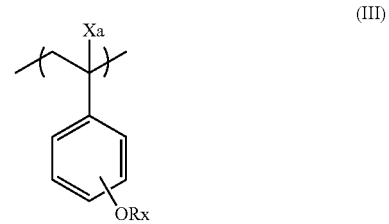

in which
Xa represents a hydrogen atom or a linear or branched alkyl group, and
Rx represents a hydrogen atom or a group that when acted on by an acid, is decomposed to thereby be cleaved.

[16] The actinic-ray- or radiation-sensitive resin composition according to any of items [9] to [15], wherein the resin (A) contains neither any aromatic group containing a phenolic hydroxyl group nor any aromatic group containing a phenolic hydroxyl group whose hydrogen atom is replaced by a group that when acted on by an acid, is decomposed to thereby be cleaved.

[17] An actinic-ray- or radiation-sensitive film formed from the actinic-ray- or radiation-sensitive resin composition according to any of items [9] to [16].

[18] A process for manufacturing a semiconductor device, comprising the method according to any of items [1] to [8].

[19] A semiconductor device manufactured by the process of item [18].

The present invention makes it feasible to provide a resist composition that excels in resolution and etching resistance performance and ensures reduction of development residue defects and to provide a method of forming a pattern with the use of the resist composition.

DETAILED DESCRIPTION OF THE INVENTION

The present invention will be described below.

With respect to the expression of a group (atomic group) used in this specification, the expression even when there is no mention of "substituted and unsubstituted" encompasses groups not only having no substituent but also having substituents. For example, the expression "alkyl groups" encompasses not only alkyls having no substituent (unsubstituted alkyls) but also alkyls having substituents (substituted alkyls).

In the present invention, the terms "actinic rays" and "radiation" mean, for example, a mercury lamp bright line spectrum, far ultraviolet rays represented by an excimer laser, extreme ultraviolet rays (EUV light), X-rays, electron beams (EB) and the like. In the present invention, the term "light" means actinic rays or radiation.

The expression "exposure" used herein, unless otherwise noted, means not only light irradiation using a mercury lamp, far ultraviolet, X-rays, EUV light, etc. but also lithography using particle beams, such as an electron beam and an ion beam.

The method of forming a pattern according to the present invention comprises the operations of forming an actinic-ray- or radiation-sensitive resin composition into a film, the actinic-ray- or radiation-sensitive resin composition comprising an acid-decomposable resin that contains a group that when acted on by an acid, is decomposed to thereby produce a polar group and contains an aromatic group and comprising a nonionic acid generator; exposing the film to light; and developing the exposed film with a developer comprising an organic solvent to thereby form a negative pattern.

It has been found by the inventors that the method of forming a pattern according to the present invention in which use is made of the above actinic-ray- or radiation-sensitive resin composition makes it feasible to form a pattern excelling in resolution and etching resistance performance while ensuring reduction of development residue defects in especially the negative pattern formation through exposure by means of a KrF light, electron beams or an EUV light and development with a developer comprising an organic solvent.

First, the actinic-ray- or radiation-sensitive resin composition for use in the pattern forming method of the present invention (hereinafter also referred to as "the actinic-ray- or radiation-sensitive resin composition of the present invention" or "the composition of the present invention") will be described in detail below.

In this connection, the actinic-ray- or radiation-sensitive film of the present invention is a film formed from the actinic-ray- or radiation-sensitive resin composition of the present invention. For example, it is a film formed by applying the actinic-ray- or radiation-sensitive resin composition onto a substrate.

<Actinic-Ray- or Radiation-Sensitive Resin Composition>

The actinic-ray- or radiation-sensitive resin composition of the present invention finds application in negative development (development in which upon exposure, exposed areas come to have a decreased solubility in a developer to thereby remain as a pattern while unexposed areas are removed). Namely, the actinic-ray- or radiation-sensitive resin composition of the present invention can be an actinic-ray- or radiation-sensitive resin composition for organic solvent development that is used in the development with a developer comprising an organic solvent. Herein, the expression "for organic solvent development" means usage in at least the operation of developing with a developer comprising an organic solvent.

The actinic-ray- or radiation-sensitive resin composition of the present invention is typically a resist composition. From the viewpoint that especially high effects can be attained, it is preferred for the same to be a negative resist composition (namely, resist composition for organic solvent development). Moreover, the composition of the present invention is typically a chemically amplified resist composition.

[1] Resin (A) that when acted on by an acid, decreases its solubility in an organic solvent The resin (A) for use in the actinic-ray- or radiation-sensitive resin composition of the present invention is a resin (hereinafter also referred to as "an acid-decomposable resin") comprising a repeating unit containing a group (hereinafter also referred to as "an acid-decomposable group") that when acted on by an acid, is decomposed to thereby produce a polar group. The resin (A) is a resin that when acted on by an acid, increases its polarity to thereby decrease its solubility in a developer comprising an organic solvent. The resin (A) further contains an aromatic group. This aromatic group may be contained in the repeating unit containing the acid-decomposable group, or in a repeating unit other than this repeating unit. Hereinafter, both of these repeating units are each referred to as "a repeating unit containing an aromatic group."

Incidentally, the resin (A) is a resin that when acted on by an acid, increases its polarity to thereby increase its solubility in an alkali developer.

[Repeating Unit Containing an Acid-Decomposable Group]

The resin (A) comprises a repeating unit containing an acid-decomposable group.

It is preferred for the acid-decomposable group to have a structure in which a polar group is protected by a group that when acted on by an acid, is decomposed and cleaved.

The polar group is not particularly limited as long as it is rendered poorly soluble or insoluble in a developer comprising an organic solvent. As preferred polar groups, there can be mentioned an acid group (group dissociated in a 2.38 mass % aqueous tetramethylammonium hydroxide solution conventionally used as a resist developer), such as a carboxyl group or a sulfonic acid group, an alcoholic hydroxyl group and the like.

The alcoholic hydroxyl group refers to a hydroxyl group bonded to a hydrocarbon group, which is other than the hydroxyl group (phenolic hydroxyl group) directly bonded to an aromatic ring. Any aliphatic alcohol substituted at its α-position with an electron withdrawing group, such as a fluorine atom, as an acid group (for example, a fluorinated alcohol group (a hexafluoroisopropanol group, etc.)) is not included in the category of the alcoholic hydroxyl group. It is preferred for the alcoholic hydroxyl group to be a hydroxyl whose pKa value is in the range of 12 to 20.

It is preferred for the acid-decomposable group to be a group whose hydrogen atom is replaced by a group cleaved by the action of an acid.

As the group cleaved by the action of an acid, there can be mentioned, for example, —$C(R_{36})(R_{37})(R_{38})$, —$C(R_{36})(R_{37})(OR_{39})$, —$C(R_{01})(R_{02})(OR_{39})$ or the like.

In the general formulae, each of $R_{36}$ to $R_{39}$ independently represents an alkyl group, a cycloalkyl group, an aryl group, an aralkyl group or an alkenyl group. $R_{36}$ and $R_{37}$ may be bonded to each other to thereby form a ring.

Each of $R_{01}$ and $R_{02}$ independently represents a hydrogen atom, an alkyl group, a cycloalkyl group, an aryl group, an aralkyl group or an alkenyl group.

Each of the alkyl groups represented by $R_{36}$ to $R_{39}$, $R_{01}$ and $R_{02}$ preferably has 1 to 8 carbon atoms. For example, there can be mentioned a methyl group, an ethyl group, a propyl group, an n-butyl group, a sec-butyl group, a hexyl group, an octyl group or the like.

The cycloalkyl groups represented by $R_{36}$ to $R_{39}$, $R_{01}$ and $R_{02}$ may be monocyclic or polycyclic. When the cycloalkyl group is monocyclic, it is preferably a cycloalkyl group having 3 to 8 carbon atoms. As such, there can be mentioned, for example, a cyclopropyl group, a cyclobutyl group, a cyclopentyl group, a cyclohexyl group, a cyclooctyl group or the like. When the cycloalkyl group is polycyclic, it is preferably a cycloalkyl group having 6 to 20 carbon atoms. As such, there can be mentioned, for example, an adamantyl group, a norbornyl group, an isobornyl group, a camphonyl group, a dicyclopentyl group, an α-pinanyl group, a tricyclodecanyl group, a tetracyclododecyl group, an androstanyl group or the like. With respect to these, at least one carbon atom of each of the cycloalkyl groups may be replaced by a heteroatom, such as an oxygen atom.

Each of the aryl groups represented by $R_{36}$ to $R_{39}$, $R_{01}$ and $R_{02}$ is preferably one having 6 to 10 carbon atoms. For example, there can be mentioned a phenyl group, a naphthyl group, an anthryl group or the like.

Each of the aralkyl groups represented by $R_{36}$ to $R_{39}$, $R_{01}$ and $R_{02}$ is preferably one having 7 to 12 carbon atoms. For example, there can be mentioned a benzyl group, a phenethyl group, a naphthylmethyl group or the like.

Each of the alkenyl groups represented by $R_{36}$ to $R_{39}$, $R_{01}$ and $R_{02}$ preferably has 2 to 8 carbon atoms. For example, there can be mentioned a vinyl group, an allyl group, a butenyl group, a cyclohexenyl group or the like.

The ring formed by the mutual bonding of $R_{36}$ and $R_{37}$ is preferably a cycloalkyl group (monocyclic or polycyclic). The cycloalkyl group is preferably a monocycloalkyl group, such as a cyclopentyl group or a cyclohexyl group, or a polycycloalkyl group, such as a norbonyl group, a tetracyclodecanyl group, a tetracyclododecanyl group or an adamantyl group. A monocycloalkyl group having 5 or 6 carbon atoms is more preferred. A monocycloalkyl group having 5 carbon atoms is most preferred.

The repeating unit containing a group that when acted on by an acid, is decomposed to thereby produce a polar group, contained in the resin (A) is preferably any of repeating units of general formula (I) below.

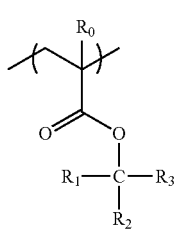

In general formula (I), $R_0$ represents a hydrogen atom, or a linear or branched alkyl group optionally substituted with a fluorine atom or a hydroxyl group.

Each of $R_1$, $R_2$ and $R_3$ independently represents an optionally substituted linear or branched alkyl group, or an optionally substituted cycloalkyl group.

Any two of $R_1$ to $R_3$ may be bonded to each other to thereby form a monocyclic or polycyclic structure.

The linear or branched alkyl group represented by $R_0$ is preferably one having 1 to 4 carbon atoms. As such, there can be mentioned a methyl group, an ethyl group, an n-propyl group, an isopropyl group, an n-butyl group, an isobutyl group, a t-butyl group or the like. A substituent may be introduced in the alkyl group. As the substituent, there can be mentioned a hydroxyl group or a fluorine atom.

It is preferred for $R_0$ to be a hydrogen atom, a methyl group, a trifluoromethyl group or a hydroxymethyl group.

Each of the alkyl groups represented by $R_1$ to $R_3$ is preferably one having 1 to 4 carbon atoms, such as a methyl group, an ethyl group, an n-propyl group, an isopropyl group, an n-butyl group, an isobutyl group or a t-butyl group.

Each of the cycloalkyl groups represented by $R_1$ to $R_3$ may be monocyclic or polycyclic. It is preferred for the cycloalkyl group to be a monocycloalkyl group, such as a cyclopentyl group or a cyclohexyl group, or a polycycloalkyl group, such as a norbonyl group, a tetracyclodecanyl group, a tetracyclododecanyl group or an adamantyl group.

The monocyclic or polycyclic structure formed by the mutual bonding of any two of $R_1$ to $R_3$ is preferably a monocycloalkyl group, such as a cyclopentyl group or a cyclohexyl group, or a polycycloalkyl group, such as a norbonyl group, a tetracyclodecanyl group, a tetracyclododecanyl group or an adamantyl group. A monocycloalkyl group having 5 or 6 carbon atoms is most preferred.

As a preferred form, there can be mentioned a form in which $R_1$ is a methyl group or an ethyl group and in which $R_2$ and $R_3$ are bonded to each other to thereby form the above-mentioned cycloalkyl group.

Substituents may be introduced in the alkyl groups and cycloalkyl groups represented by $R_1$ to $R_3$. As the substituents, there can be mentioned, for example, a hydroxyl group, a halogen atom (e.g., a fluorine atom), an alkyl group (having 1 to 4 carbon atoms), a cycloalkyl group (having 3 to 8 carbon atoms), an alkoxy group (having 1 to 4 carbon atoms), a carboxyl group, an alkoxycarbonyl group (having 2 to 6 carbon atoms) and the like. The number of carbon atoms of each thereof is preferably 8 or less.

In an especially preferred form of the repeating units of general formula (I) above, each of $R_1$, $R_2$ and $R_3$ independently represents a linear or branched alkyl group.

In this form, each of the linear or branched alkyl groups represented by $R_1$, $R_2$ and $R_3$ is preferably one having 1 to 4 carbon atoms. As such, there can be mentioned a methyl group, an ethyl group, an n-propyl group, an isopropyl group, an n-butyl group, an isobutyl group or a tert-butyl group.

$R_1$ is preferably a methyl group, an ethyl group, an n-propyl group or an n-butyl group; more preferably a methyl group or an ethyl group; and most preferably a methyl group.

$R_2$ is preferably a methyl group, an ethyl group, an n-propyl group, an isopropyl group or an n-butyl group; more preferably a methyl group or an ethyl group; and most preferably a methyl group.

$R_3$ is preferably a methyl group, an ethyl group, an n-propyl group, an isopropyl group, an n-butyl group, an isobutyl group or a tert-butyl group; more preferably a methyl group, an ethyl group, an isopropyl group or an isobutyl group; and most preferably a methyl group, an ethyl group or an isopropyl group.

Preferred particular examples of the repeating units of general formula (I) are shown below, which however in no way limit the scope of the present invention.

In the particular examples, Rx represents a hydrogen atom, CH$_3$, CF$_3$ or CH$_2$OH. Each of Rxa and Rxb represents an alkyl group having 1 to 4 carbon atoms. Z represents a substituent. When there are a plurality of Z's, they may be identical to or different from each other. In the formulae, p is 0 or a positive integer. The particular examples and preferred examples of Z's are the same as those of the substituents that can be introduced in the groups represented by R$_1$ to R$_3$, etc.

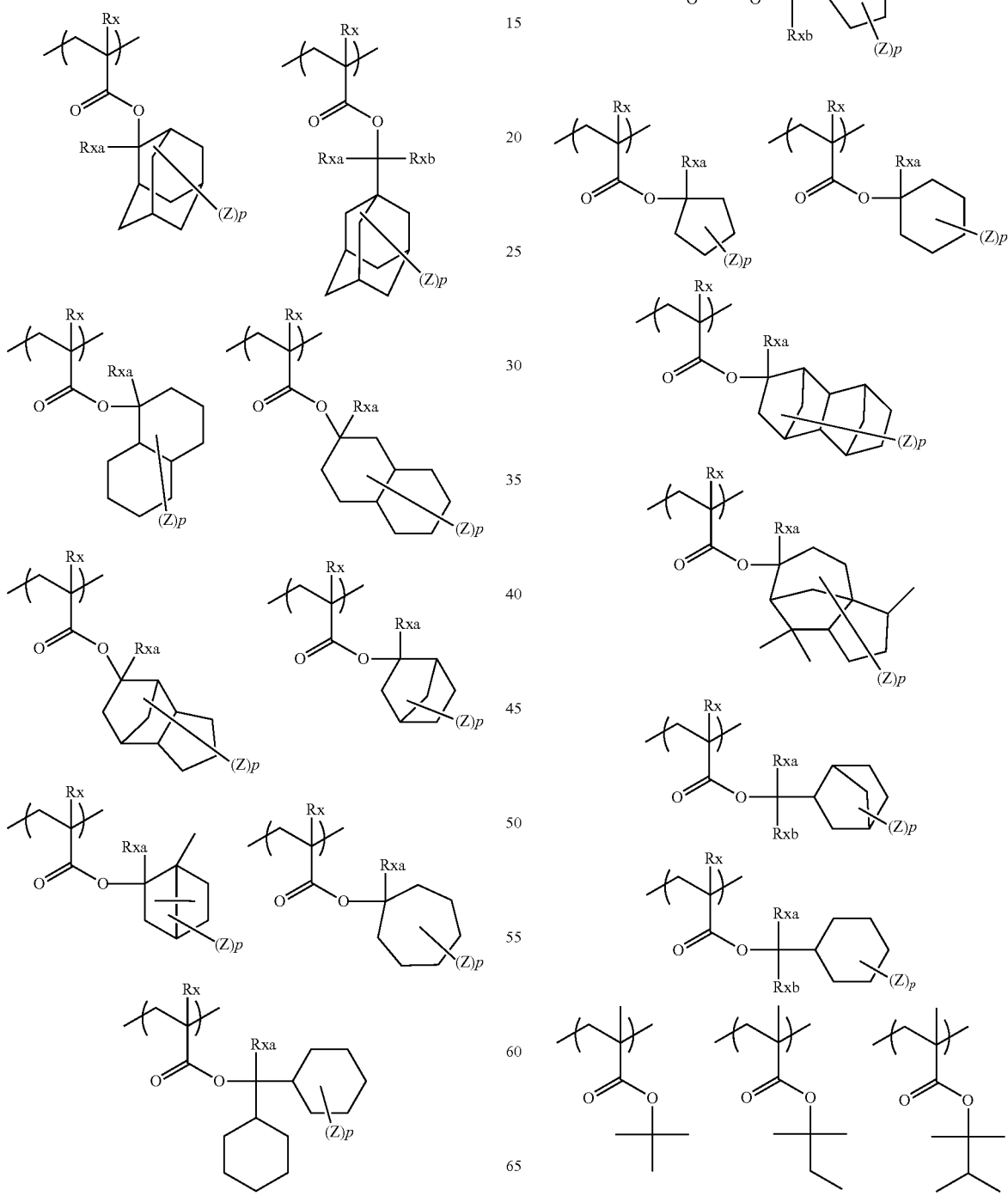

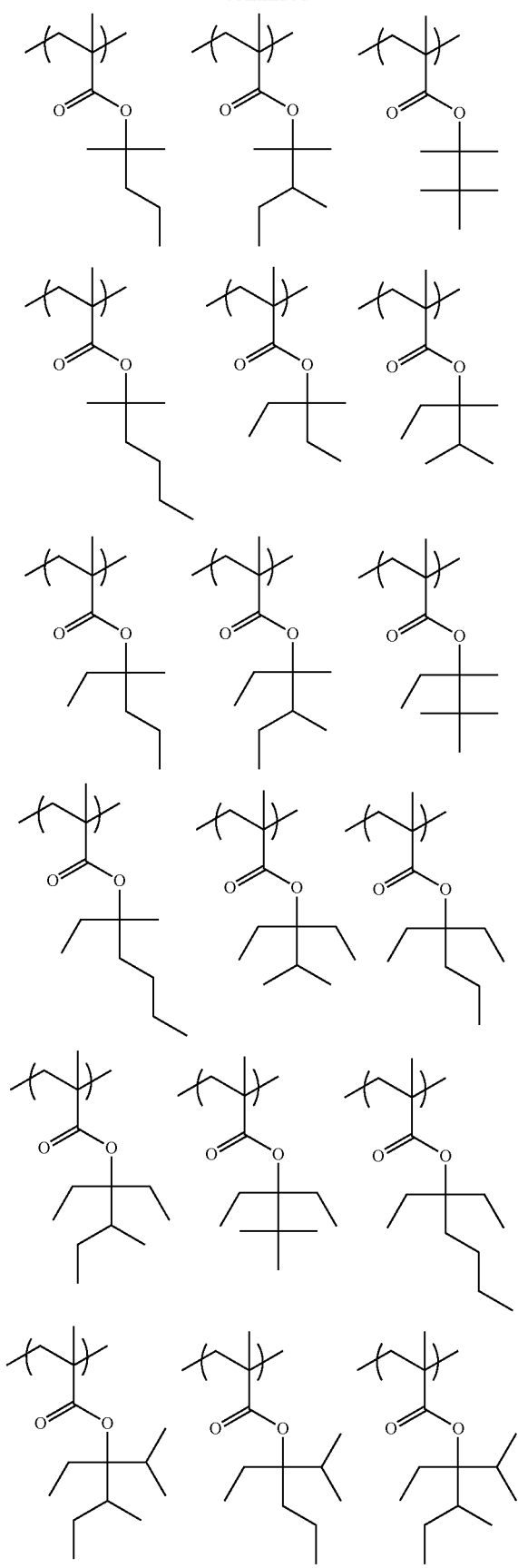
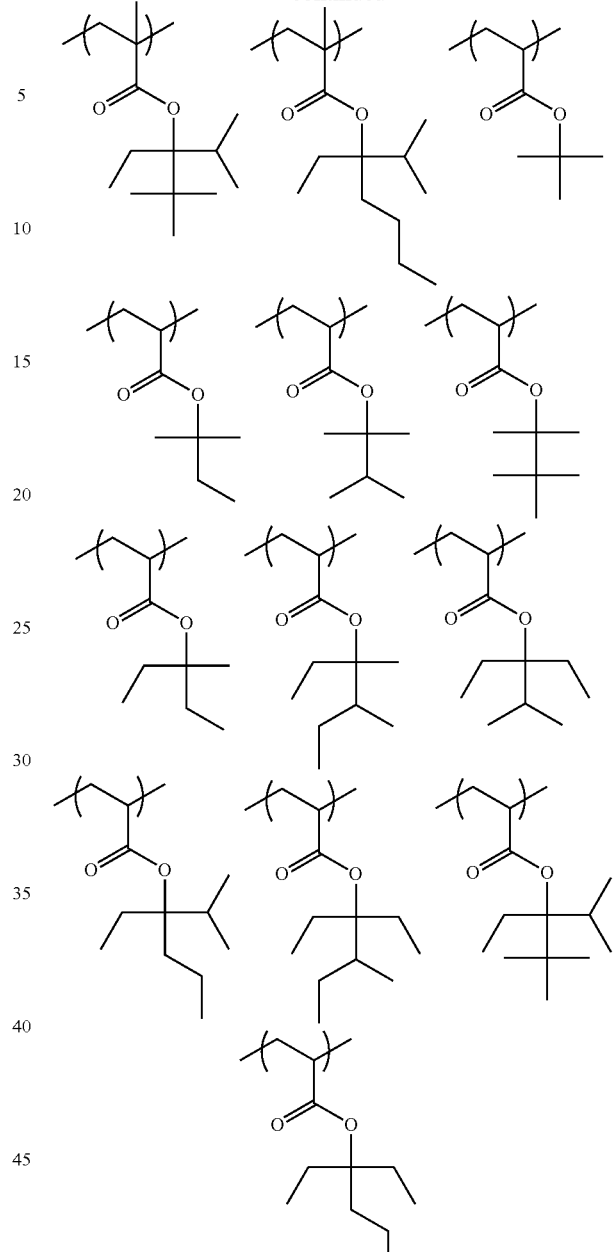

In the resin (A), one type of repeating unit containing an acid-decomposable group may be used alone, or two or more types thereof may be used in combination.

In the resin (A) according to the present invention, the content (when two or more types are contained, the sum thereof) of repeating unit containing an acid-decomposable group (preferably, any of repeating units of general formula (I) above) is preferably in the range of 20 to 90 mol % based on all the repeating units of the resin (A) from the viewpoint that, while the solubility of exposed areas in an organic developer is satisfactorily lowered, the solubility of unexposed areas is held satisfactory to thereby enhance the dissolution contrast. The content is more preferably in the range of 30 to 80 mol %, further more preferably 40 to 70 mol % and most preferably 40 to 60 mol %.

[Repeating Unit Containing an Aromatic Group]

The resin (A) may further comprise a repeating unit containing an aromatic group.

In the present invention, it is preferred for the repeating unit (b) containing an aromatic group to be any of repeating units of general formula (II) below.

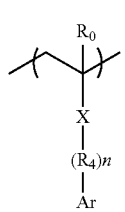

(II)

In general formula (II) above, $R_0$ represents a hydrogen atom, or an optionally substituted linear or branched alkyl group.

X represents a single bond or a bivalent connecting group.

Ar represents an optionally substituted aromatic group. When a substituent is introduced in the aromatic group, the substituent is any of an alkyl group (optionally substituted) a cycloalkyl group (optionally substituted), an aryl group, a halogen atom, a cyano group, an amino group, a nitro group and a carboxyl group.

$R_4$ represents an optionally substituted alkylene group, and n is an integer of 0 to 4.

The particular examples and preferred examples of the linear or branched alkyl groups represented by $R_0$ are the same as mentioned above in connection with the linear or branched alkyl groups represented by $R_0$ in general formula (I).

X is preferably a bivalent connecting group. As preferred bivalent connecting groups, there can be mentioned —COO—, —CONH— and the like.

The alkylene group represented by $R_4$ is optionally substituted, and is preferably an alkylene group having 1 to 4 carbon atoms. As such, there can be mentioned a methylene group, an ethylene group, a propylene group or the like. As a substituent that can be introduced in the alkylene group represented by $R_4$, there can be mentioned an alkyl group having 1 to 4 carbon atoms, a halogen atom such as a fluorine atom, or the like.

A substituent that can be introduced in the alkylene group represented by $R_4$ and a substituent that can be introduced in the aromatic group represented by Ar may be bonded to each other to thereby form a ring. As the group constituting the ring, there can be mentioned an alkylene group (for example, an ethylene group or a propylene group).

From the viewpoint that the resin has an appropriate glass transition temperature (Tg) at pattern formation, it is preferred for $R_4$ to be a single bond or an optionally substituted methylene group.

The aromatic group represented by Ar is optionally substituted, and is preferably an aryl group having 6 to 10 carbon atoms. As such, there can be mentioned, for example, a phenyl group or a naphthyl group.

As a substituent that can be introduced in the aromatic group represented by Ar, there can be mentioned a linear or branched alkyl group (preferably having 1 to 4 carbon atoms), a cycloalkyl group (preferably having 3 to 10 carbon atoms), an aryl group (preferably having 6 to 10 carbon atoms), a halogen atom such as a fluorine atom, a cyano group, an amino group, a nitro group, a carboxyl group, or the like. A substituent may further be introduced in the linear or branched alkyl group, cycloalkyl group and aryl group mentioned above as the substituent. As such a further substituent, there can be mentioned a halogen atom such as a fluorine atom, or the like.

When the aromatic group represented by Ar is a phenyl group and when a substituent is introduced in the phenyl group, it is preferred for the substituent to be introduced in the 4-position of the phenyl group.

From the viewpoint of etching resistance, it is preferred for the aromatic group represented by Ar to be an optionally substituted phenyl group.

In the resin (A) according to the present invention, the content (when two or more types are contained, the sum thereof) of any of repeating units of general formula (II) above is preferably in the range of 10 to 70 mol % based on all the repeating units of the resin (A) from the viewpoint that, while the solubility of exposed areas in an organic developer is satisfactorily lowered, the solubility of unexposed areas is held satisfactory to thereby enhance the dissolution contrast and from the viewpoint that an etching resistance is imparted. The content is more preferably in the range of 15 to 60 mol %, most preferably 20 to 55 mol %.

The resin (A) may comprise any of repeating units of general formula (III) below as the repeating unit containing an aromatic group.

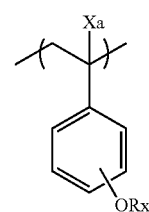

(III)

In general formula (III) above,

Xa represents a hydrogen atom or a linear or branched alkyl group.

Rx represents a hydrogen atom or a group that when acted on by an acid, is decomposed to thereby be cleaved.

The particular examples and preferred examples of the linear or branched alkyl groups represented by Xa are the same as mentioned above in connection with the linear or branched alkyl groups represented by $R_0$ in general formula (I).

The particular examples and preferred examples of the groups that when acted on by an acid, are decomposed to thereby be cleaved, represented by Rx are the same as mentioned above in connection with the groups that when acted on by an acid, are decomposed to thereby be cleaved, which groups protect the polar groups constituting acid-decomposable groups in the resin (A).

In the resin (A) according to the present invention, the content (when two or more types are contained, the sum thereof) of any of repeating units of general formula (III) above is preferably up to 20 mol % based on all the repeating units of the resin (A) from the viewpoint that, while the solubility of exposed areas in an organic developer is satisfactorily lowered, the solubility of unexposed areas is held satisfactory to thereby enhance the dissolution contrast. The content is more preferably up to 10 mol %, further more preferably up to 5 mol % and ideally 0 mol %. Namely, containing none of these repeating units is most preferred. When repeating units of general formula (III) above are contained in an amount of more than 20 mol % based on all the repeating units of the resin (A), it is likely that the dissolution of the resin in an organic solvent is excessive to thereby render the pattern resolution and rectangularity poor.

[Other Repeating Unit]

The resin (A) may further comprise a repeating unit with a lactone structure. It is preferred for the repeating unit with a lactone structure to be any of the repeating units of general formula (AII) below.

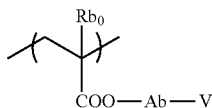

(AII)

In general formula (AII), $Rb_0$ represents a hydrogen atom, a halogen atom or an optionally substituted alkyl group (preferably having 1 to 4 carbon atoms).

As preferred substituents that may be introduced in the alkyl group represented by $Rb_0$, there can be mentioned a hydroxyl group and a halogen atom. As the halogen atom represented by $Rb_0$, there can be mentioned a fluorine atom, a chlorine atom, a bromine atom or an iodine atom. $Rb_0$ is preferably a hydrogen atom, a methyl group, a hydroxymethyl group or a trifluoromethyl group. A hydrogen atom and a methyl group are especially preferred.

Ab represents a single bond, an alkylene group, a bivalent connecting group with a mono- or polycycloalkyl structure, an ether bond, an ester bond, a carbonyl group, or a bivalent connecting group resulting from combination of these. Ab is preferably a single bond or any of the bivalent connecting groups of the formula -$Ab_1$-$CO_2$—.

$Ab_1$ represents a linear or branched alkylene group or a mono- or polycycloalkylene group, preferably a methylene group, an ethylene group, a cyclohexylene group, an adamantylene group or a norbornylene group.

V represents a group with a lactone structure.

The group with a lactone structure is not limited as long as a lactone structure is introduced therein. A 5 to 7-membered ring lactone structure is preferred, and one resulting from the condensation of a 5 to 7-membered ring lactone structure with another cyclic structure effected in a fashion to form a bicycle structure or spiro structure is especially preferred. More preferably, the resin comprises a repeating unit with any of the lactone structures of general formulae (LC1-1) to (LC1-17) below. The lactone structures may be directly bonded to the principal chain. Preferred lactone structures are those of formulae (LC1-1), (LC1-4), (LC1-5), (LC1-6), (LC1-8), (LC1-13) and (LC1-14).

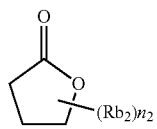

LC1-1

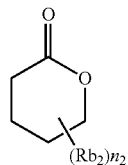

LC1-2

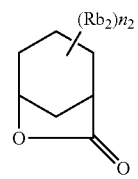

LC1-3

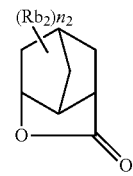

LC1-4

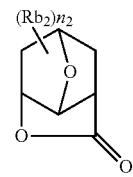

LC1-5

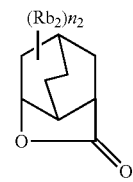

LC1-6

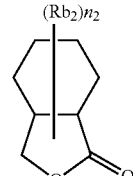

LC1-7

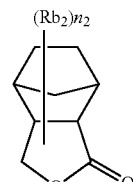

LC1-8

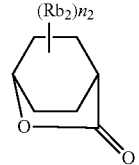

LC1-9

-continued

LC1-10
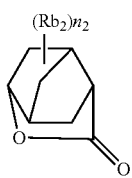

LC1-11
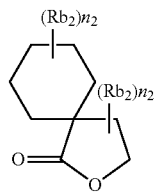

LC1-12
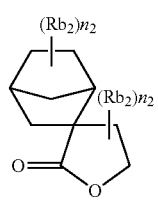

LC1-13
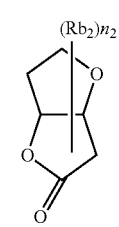

LC1-14
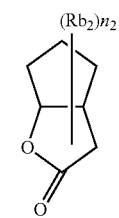

LC1-15
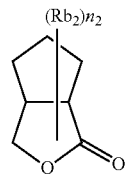

LC1-16
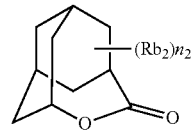

LC1-17
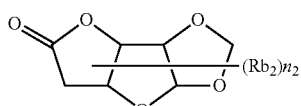

A substituent (Rb₂) is optionally introduced in the portion of the lactone structure. As preferred substituents (Rb₂), there can be mentioned an alkyl group having 1 to 8 carbon atoms, a monocycloalkyl group having 4 to 7 carbon atoms, an alkoxy group having 1 to 8 carbon atoms, an alkoxycarbonyl group having 2 to 8 carbon atoms, a carboxyl group, a halogen atom, a hydroxyl group, a cyano group, an acid-decomposable group and the like. An alkyl group having 1 to 4 carbon atoms, a cyano group and an acid-decomposable group are more preferred. In the formulae, $n_2$ is an integer of 0 to 4. When $n_2$ is 2 or greater, the plurality of introduced substituents (Rb₂) may be identical to or different from each other. Further, the plurality of introduced substituents (Rb₂) may be bonded to each other to thereby form a ring.

The repeating unit containing a lactone group is generally present in the form of optical isomers. Any of the optical isomers may be used. It is both appropriate to use one type of optical isomer alone and to use a plurality of optical isomers in the form of a mixture. When one type of optical isomer is mainly used, the optical purity (ee) thereof is preferably 90% or higher, more preferably 95% or higher.

It is optional for the resin (A) to comprise the repeating unit containing a lactone structure. When the repeating unit containing a lactone structure is contained, the content of thereof in the resin (A), based on all the repeating units of the resin, is preferably in the range of 0.5 to 50 mol %, more preferably 1 to 40 mol % and further more preferably 3 to 30 mol %. One type of this repeating unit may be used alone, or two or more types thereof may be used in combination. Not only the resolution of the pattern but also the rectangular profile thereof can be enhanced by employing specified lactone structures.

Particular examples of the repeating units each having a lactone structure contained in the resin (A) are shown below, which in no way limit the scope of the present invention. In the following formulae, Rx represents H, $CH_3$, $CH_2OH$ or $CF_3$.

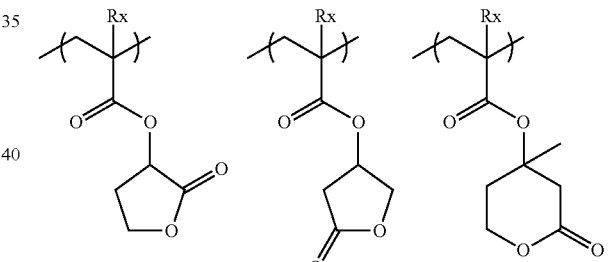

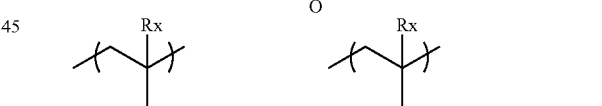

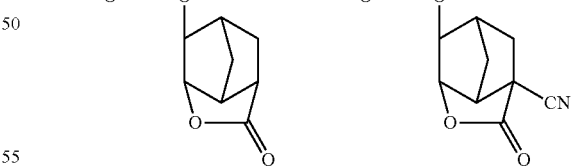

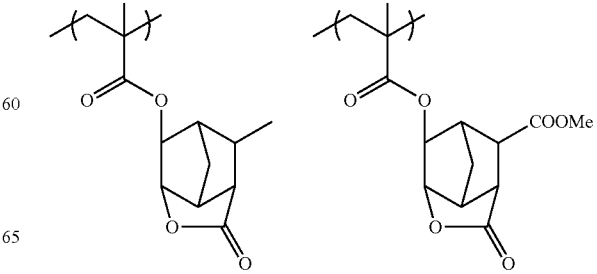

-continued

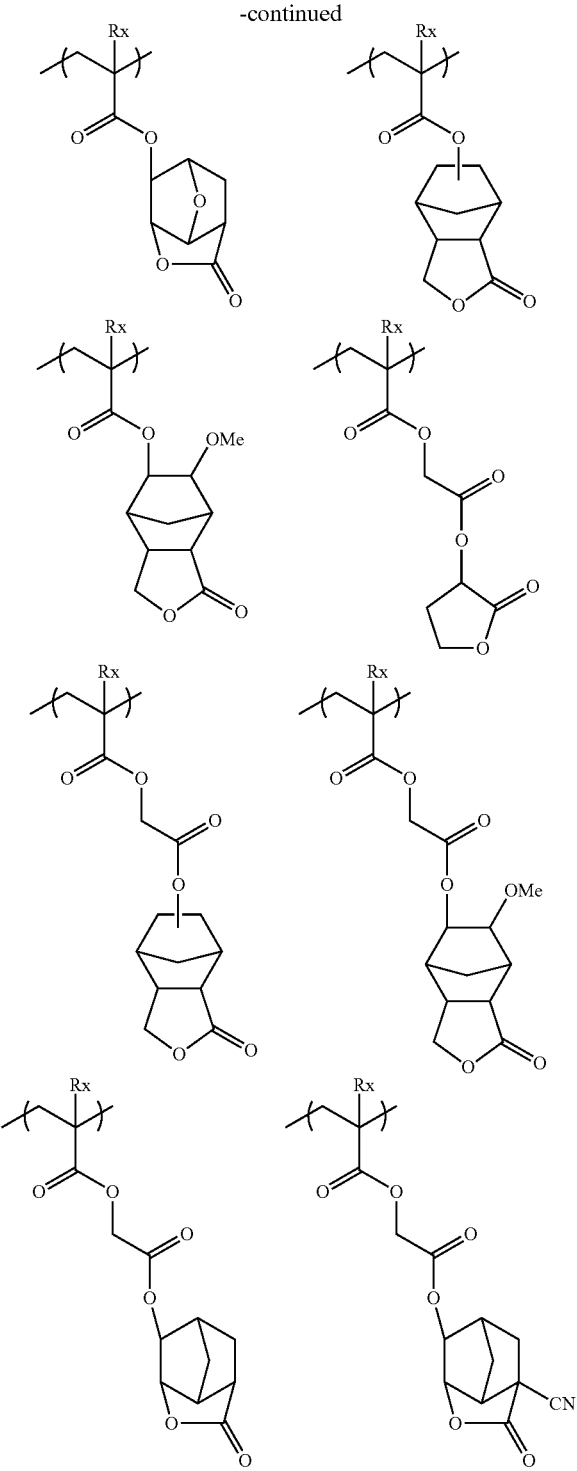

The resin (A) may comprise a repeating unit containing an acid group. As the acid group, there can be mentioned a carboxyl group, a sulfonamido group, a sulfonylimido group, a bisulfonylimido group or an aliphatic alcohol substituted at its α-position with an electron-withdrawing group (for example, a hexafluoroisopropanol group). It is preferred to comprise a repeating unit containing a carboxyl group. The incorporation of the repeating unit containing an acid group would increase the resolution in, for example, contact hole usage. The repeating unit containing an acid group is prefer-ably any of a repeating unit wherein the acid group is directly bonded to the principal chain of a resin such as a repeating unit of acrylic acid or methacrylic acid, a repeating unit wherein the acid group is bonded via a connecting group to the principal chain of a resin and a repeating unit wherein the acid group is introduced in a terminal of a polymer chain by the use of a chain transfer agent or polymerization initiator containing the acid group in the stage of polymerization. The connecting group may have a cyclohydrocarbon structure of a single ring or multiple rings. The repeating unit of acrylic acid or methacrylic acid is especially preferred.

Specific examples of the repeating units each containing an acid group are shown below, which however in no way limit the scope of the present invention.

In the specific examples, Rx represents H, $CH_3$, $CH_2OH$ or $CF_3$.

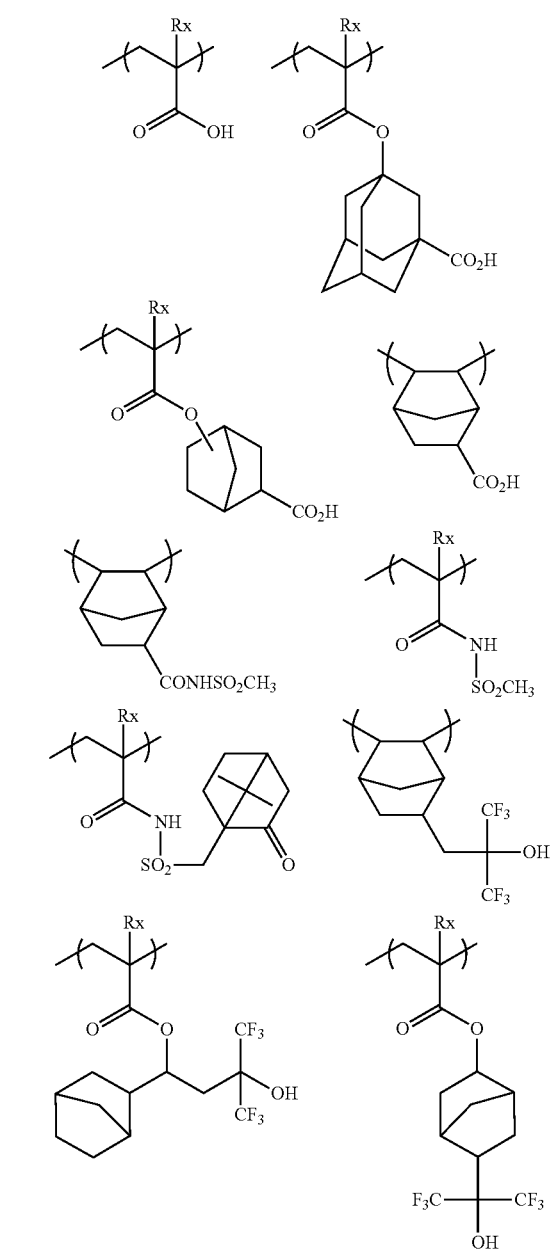

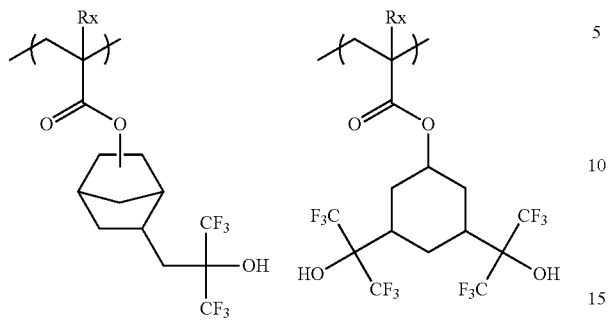

It is optional for the resin (A) to contain the repeating unit containing an acid group. When the repeating unit containing an acid group is contained in the resin (A), the content thereof based on all the repeating units of the resin (A) is preferably in the range of 1 to 25 mol %, more preferably 1 to 20 mol % and further more preferably 3 to 15 mol %.

The resin (A) may further comprise a repeating unit containing a hydroxyl group or a cyano group other than the foregoing repeating units. This would realize enhancements of the adhesion to substrate and developer affinity. The repeating unit containing a hydroxyl group or a cyano group is preferably a repeating unit having an alicyclic hydrocarbon structure substituted with a hydroxyl group or a cyano group, which repeating unit preferably contains no acid-decomposable group. In the alicyclic hydrocarbon structure substituted with a hydroxyl group or a cyano group, the alicyclic hydrocarbon structure is preferably comprised of an adamantyl group, a diamantyl group or a norbornane group, more preferably an adamantyl group. The alicyclic hydrocarbon structure is preferably substituted with a hydroxyl group. It is especially preferred to comprise a repeating unit containing an adamantyl group substituted with at least one hydroxyl group.

From the viewpoint of the inhibition of the diffusion of any generated acid, it is most preferred for the resin (A) to comprise a repeating unit containing a hydroxyadamantyl group or a dihydroxyadamantyl group.

The alicyclic hydrocarbon structure substituted with a hydroxyl group or a cyano group is preferably any of the partial structures of general formulae (VIIa) to (VIId) below, more preferably general formula (VIIa).

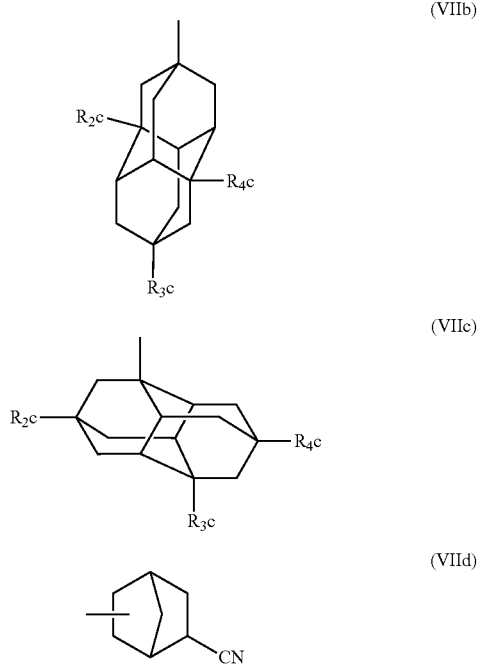

In general formulae (VIIa) to (VIIc), each of $R_2c$ to $R_4c$ independently represents a hydrogen atom, a hydroxyl group or a cyano group, provided that at least one of $R_2c$ to $R_4c$ represents a hydroxyl group or a cyano group. Preferably, one or two of $R_2c$ to $R_4c$ are hydroxyl groups and the remainder is a hydrogen atom. In general formula (VIIa), more preferably, two of $R_2c$ to $R_4c$ are hydroxyl groups and the remainder is a hydrogen atom.

As the repeating units with any of the partial structures of general formulae (VIIa) to (VIId), there can be mentioned the repeating units of general formulae (AIIa) to (AIId) below.

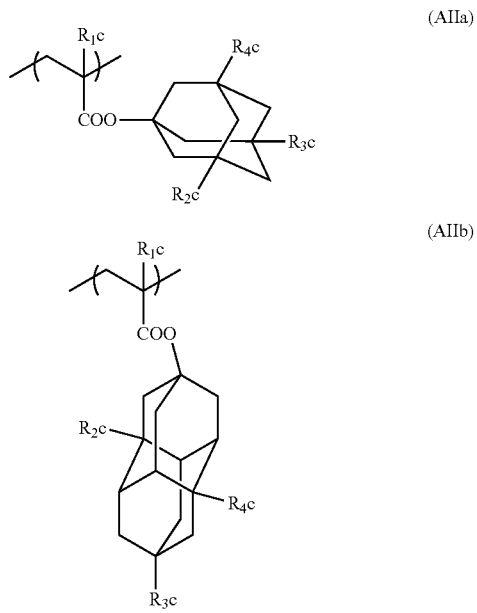

-continued

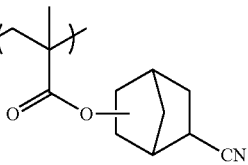

(AIIc)

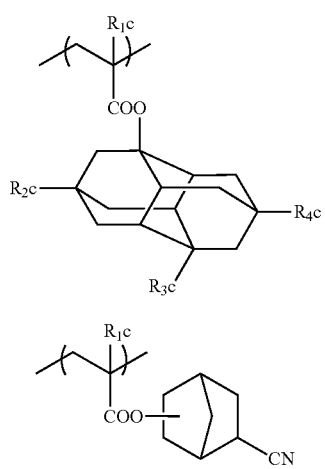

(AIId)

In general formulae (AIIa) to (AIId), $R_1c$ represents a hydrogen atom, a methyl group, a trifluoromethyl group or a hydroxymethyl group.

$R_2c$ to $R_4c$ have the same meanings as those of $R_2c$ to $R_4c$ of general formulae (VIIa) to (VIIc).

Specific examples of the repeating units each containing a hydroxyl group or a cyano group are shown below, which however in no way limit the scope of the present invention.

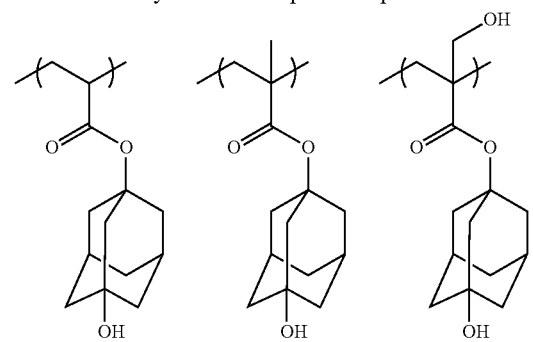

-continued

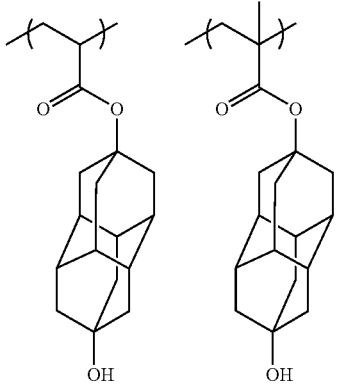

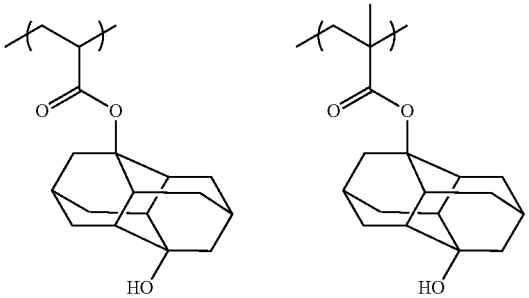

It is optional for the resin (A) to comprise the repeating unit containing a hydroxyl group or a cyano group. When the repeating unit containing a hydroxyl group or a cyano group is contained in the resin (A), the content thereof, based on all the repeating units of resin (A), is preferably in the range of 1 to 40 mol %, more preferably 1 to 30 mol % and further more preferably 3 to 20 mol %.

The resin (A) according to the present invention can further comprise a repeating unit having an alicyclic hydrocarbon structure in which no polar group (for example, the above acid group, hydroxyl group or cyano group) is introduced and exhibiting no acid-decomposability. This realizes an appropriate regulation of the solubility of the resin in the stage of development with a developer comprising an organic solvent. As such a repeating unit, there can be mentioned any of the repeating units of general formula (IV) below.

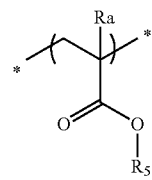

(IV)

In general formula (IV), $R_5$ represents a hydrocarbon group having at least one cyclic structure in which no polar group is introduced.

Ra represents a hydrogen atom, an alkyl group or a group of the formula —CH$_2$—O—Ra$_2$. In this formula, Ra$_2$ represents a hydrogen atom, an alkyl group or an acyl group. Ra is preferably a hydrogen atom, a methyl group, a hydroxymethyl group or a trifluoromethyl group, most preferably a hydrogen atom or a methyl group.

The cyclic structures introduced in R$_5$ include a monocyclic hydrocarbon group and a polycyclic hydrocarbon group. As the monocyclic hydrocarbon group, there can be mentioned, for example, a cycloalkyl group having 3 to 12 carbon atoms, such as a cyclopentyl group, a cyclohexyl group, a cycloheptyl group or a cyclooctyl group, or a cycloalkenyl group having 3 to 12 carbon atoms, such as a cyclohexenyl group. Preferably, the monocyclic hydrocarbon group is a monocyclic hydrocarbon group having 3 to 7 carbon atoms. A cyclopentyl group and a cyclohexyl group can be mentioned as more preferred monocyclic hydrocarbon groups.

The polycyclic hydrocarbon groups include ring-assembly hydrocarbon groups and crosslinked-ring hydrocarbon groups. Examples of the ring-assembly hydrocarbon groups include a bicyclohexyl group and a perhydronaphthalenyl group. As the crosslinked-ring hydrocarbon rings, there can be mentioned, for example, bicyclic hydrocarbon rings, such as pinane, bornane, norpinane, norbornane and bicyclooctane rings (e.g., bicyclo[2.2.2]octane ring or bicyclo[3.2.1]octane ring); tricyclic hydrocarbon rings, such as homobledane, adamantane, tricyclo[5.2.1.0$^{2,6}$]decane and tricyclo[4.3.1.1$^{2,5}$] undecane rings; and tetracyclic hydrocarbon rings, such as tetracyclo[4.4.0.1$^{2,5}$.1$^{7,10}$]dodecane and perhydro-1,4-methano-5,8-methanonaphthalene rings. Further, the crosslinked-ring hydrocarbon rings include condensed-ring hydrocarbon rings, for example, condensed rings resulting from condensation of multiple 5- to 8-membered cycloalkane rings, such as perhydronaphthalene (decalin), perhydroanthracene, perhydrophenanthrene, perhydroacenaphthene, perhydrofluorene, perhydroindene and perhydrophenalene rings.

As preferred crosslinked-ring hydrocarbon rings, there can be mentioned a norbornyl group, an adamantyl group, a bicyclooctanyl group and a tricyclo[5,2,1,0$^{2,6}$]decanyl group and the like. As more preferred crosslinked-ring hydrocarbon rings, there can be mentioned a norbornyl group and an adamantyl group.

Substituents may be introduced in these alicyclic hydrocarbon groups. As preferred substituents, there can be mentioned a halogen atom, an alkyl group, a hydroxyl group having its hydrogen atom substituted, an amino group having its hydrogen atom substituted and the like. The halogen atom is preferably a bromine, chlorine or fluorine atom, and the alkyl group is preferably a methyl, ethyl, butyl or t-butyl group. A substituent may further be introduced in the alkyl group. As the optional further substituent, there can be mentioned a halogen atom, an alkyl group, a hydroxyl group having its hydrogen atom substituted or an amino group having its hydrogen atom substituted.

As the substituent for the hydrogen atom, there can be mentioned, for example, an alkyl group, a cycloalkyl group, an aralkyl group, a substituted methyl group, a substituted ethyl group, an alkoxycarbonyl group or an aralkyloxycarbonyl group. The alkyl group is preferably an alkyl group having 1 to 4 carbon atoms. The substituted methyl group is preferably a methoxymethyl, methoxythiomethyl, benzyloxymethyl, t-butoxymethyl or 2-methoxyethoxymethyl group. The substituted ethyl group is preferably a 1-ethoxyethyl or 1-methyl-1-methoxyethyl group. The acyl group is preferably an aliphatic acyl group having 1 to 6 carbon atoms, such as a formyl, acetyl, propionyl, butyryl, isobutyryl, valeryl or pivaloyl group. The alkoxycarbonyl group is, for example, an alkoxycarbonyl group having 1 to 4 carbon atoms.

It is optional for the resin (A) to comprise the repeating unit having an alicyclic hydrocarbon structure in which no polar group is introduced and exhibiting no acid-decomposability. When the repeating unit having an alicyclic hydrocarbon structure in which no polar group is introduced and exhibiting no acid-decomposability is contained in the resin (A), the content thereof based on all the repeating units of the resin (A) is preferably in the range of 1 to 40 mol %, more preferably 1 to 20 mol %.

Particular examples of the repeating units having an alicyclic hydrocarbon structure in which no polar group is introduced and exhibiting no acid-decomposability are shown below, which in no way limit the scope of the present invention. In the formulae, Ra represents H, CH$_3$, CH$_2$OH or CF$_3$.

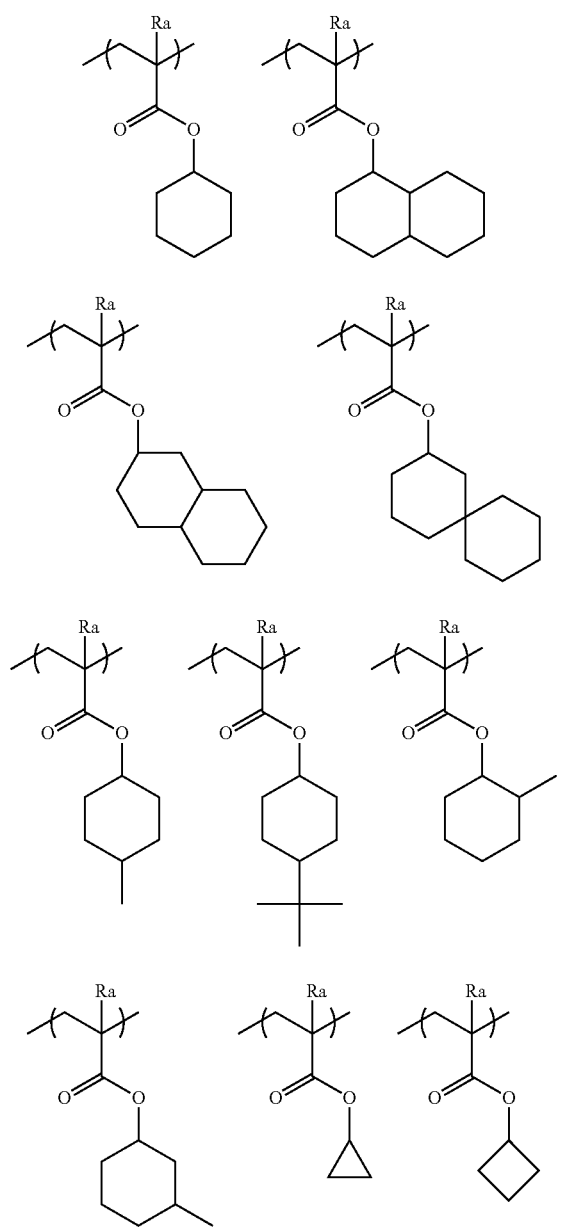

-continued

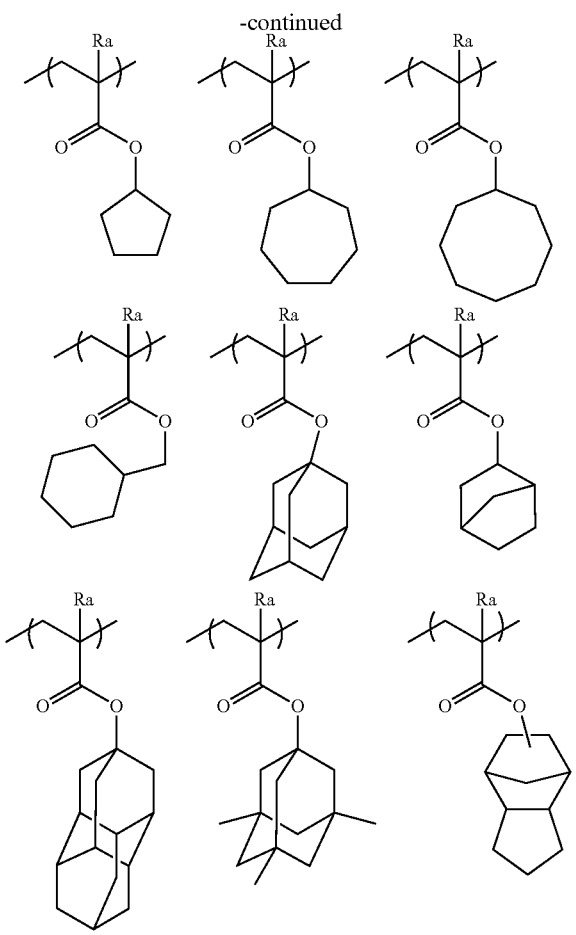

The resin (A) for use in the composition of the present invention can comprise, in addition to the foregoing repeating structural units, various repeating structural units for the purpose of regulating the dry etching resistance, standard developer adaptability, substrate adhesion, resist profile and generally required properties of the actinic-ray- or radiation-sensitive resin composition such as resolving power, heat resistance and sensitivity.

As such repeating structural units, there can be mentioned those corresponding to the following monomers, which however are nonlimiting.

The use of such repeating structural units would realize fine regulation of the required properties of the resin for use in the composition of the present invention, especially:

(1) solubility in applied solvents,
(2) film forming easiness (glass transition point),
(3) alkali developability,
(4) film thinning (selections of hydrophilicity/hydrophobicity and alkali-soluble group),
(5) adhesion of unexposed area to substrate,
(6) dry etching resistance, etc.

As appropriate monomers, there can be mentioned, for example, a compound having one unsaturated bond capable of addition polymerization, selected from among acrylic esters, methacrylic esters, acrylamides, methacrylamides, allyl compounds, vinyl ethers, vinyl esters, styrenes, crotonic esters and the like.

In addition, any unsaturated compound capable of addition polymerization that is copolymerizable with monomers corresponding to the above various repeating structural units may be copolymerized therewith.

In the resin (A) for use in the composition of the present invention, the molar ratios of individual repeating structural units contained are appropriately determined from the viewpoint of regulating the dry etching resistance, standard developer adaptability, substrate adhesion and resist profile of the actinic-ray- or radiation-sensitive resin composition and generally required properties of the resist such as resolving power, heat resistance and sensitivity.

The resin (A) according to the present invention may have any of the random, block, comb and star forms. The resin (A) can be synthesized by, for example, the radical, cation or anion polymerization of unsaturated monomers corresponding to given structures. Alternatively, the intended resin can be obtained by first polymerizing unsaturated monomers corresponding to the precursors of given structures and thereafter carrying out a polymer reaction.

The resin (A) according to the present invention can be synthesized in accordance with routine methods (for example, radical polymerization). As general synthesizing methods, there can be mentioned, for example, a batch polymerization method in which a monomer species and an initiator are dissolved in a solvent and heated to thereby carry out polymerization, a dropping polymerization method in which a solution of monomer species and initiator is dropped into a heated solvent over a period of 1 to 10 hours, and the like. The dropping polymerization method is preferred. As a reaction solvent, there can be mentioned, for example, an ether such as tetrahydrofuran, 1,4-dioxane or diisopropyl ether, a ketone such as methyl ethyl ketone or methyl isobutyl ketone, an ester solvent such as ethyl acetate, an amide solvent such as dimethylformamide or dimethylacetamide, or the solvent capable of dissolving the composition of the present invention, such as propylene glycol monomethyl ether acetate, propylene glycol monomethyl ether or cyclohexanone, to be described hereinafter. Preferably, the polymerization is carried out with the use of the same solvent as that used in the actinic-ray- or radiation-sensitive resin composition of the present invention. This would inhibit any particle generation during storage.

The polymerization reaction is preferably carried out in an atmosphere comprised of an inert gas, such as nitrogen or argon. The polymerization is initiated by use of a commercially available radical initiator (azo initiator, peroxide, etc.) as a polymerization initiator. Among the radical initiators, an azo initiator is preferred, and azo initiators having an ester group, a cyano group and a carboxyl group are especially preferred. As specific preferred initiators, there can be mentioned azobisisobutyronitrile, azobisdimethylvaleronitrile, dimethyl 2,2'-azobis(2-methylpropionate) and the like. If desirable, the initiator may be supplemented, or may be added in fractional amounts. After the completion of the reaction, the reaction liquid is poured into a solvent, and the intended polymer is recovered by a method of powder or solid recovery or the like. The reaction concentration is in the range of 5 to 50 mass %, preferably 10 to 30 mass %. The reaction temperature is generally in the range of 10 to 150° C., preferably 30 to 120° C. and more preferably 60 to 100° C.

After the completion of the reaction, the reaction mixture is allowed to stand still to cool to room temperature and purified. In the purification, use can be made of routine methods, such as a liquid-liquid extraction method in which residual monomers and oligomer components are removed by water washing or by the use of a combination of appropriate solvents, a method of purification in solution form such as ultrafiltration capable of extraction removal of only components of a given molecular weight or below, a re-precipitation method in which a resin solution is dropped into a poor solvent to thereby coagulate the resin in the poor solvent and thus remove residual monomers, etc., and a method of purification in solid form such as washing of a resin slurry obtained by filtration with the use of a poor solvent. For example, the reaction solution is brought into contact with a solvent wherein the resin is poorly soluble or insoluble (poor solvent) amounting to 10 or less, preferably 10 to 5 times the volume of the reaction solution to thereby precipitate the resin as a solid.

The solvent for use in the operation of precipitation or re-precipitation from a polymer solution (precipitation or re-precipitation solvent) is not limited as long as the solvent is a poor solvent for the polymer. Use can be made of any solvent appropriately selected from among a hydrocarbon, a halogenated hydrocarbon, a nitro compound, an ether, a ketone, an ester, a carbonate, an alcohol, a carboxylic acid, water, a mixed solvent containing these solvents and the like, according to the type of the polymer.

The amount of precipitation or re-precipitation solvent used can be appropriately selected taking efficiency, yield, etc. into account. Generally, the amount is in the range of 100 to 10,000 parts by mass, preferably 200 to 2000 parts by mass and more preferably 300 to 1000 parts by mass per 100 parts by mass of polymer solution.

The temperature at which the precipitation or re-precipitation is carried out can be appropriately selected taking efficiency and operation easiness into account. Generally, the temperature is in the range of about 0 to 50° C., preferably about room temperature (for example, about 20 to 35° C.). The operation of precipitation or re-precipitation can be carried out by a routine method, such as a batch or continuous method, with the use of a customary mixing container, such as an agitation vessel.

The polymer resulting from the precipitation or re-precipitation is generally subjected to customary solid/liquid separation, such as filtration or centrifugal separation, and dried before use. The filtration is carried out with the use of a filter medium ensuring solvent resistance, preferably under pressure. The drying is performed at about 30 to 100° C., preferably about 30 to 50° C. under ordinary pressure or reduced pressure (preferably reduced pressure).

Alternatively, after the precipitation and separation of the resin, the resultant resin may be once more dissolved in a solvent and brought into contact with a solvent in which the resin is poorly soluble or insoluble. Specifically, the method may include the operations of, after the completion of the radical polymerization reaction, bringing the polymer into contact with a solvent wherein the polymer is poorly soluble or insoluble to thereby attain resin precipitation (operation a), separating the resin from the solution (operation b), re-dissolving the resin in a solvent to thereby obtain a resin solution A (operation c), thereafter bringing the resin solution A into contact with a solvent wherein the resin is poorly soluble or insoluble amounting to less than 10 times (preferably 5 times or less) the volume of the resin solution A to thereby precipitate a resin solid (operation d) and separating the precipitated resin (operation e).

Further, the operation of dissolving a synthesized resin in a solvent to thereby obtain a solution and heating the solution at about 30 to 90° C. for about 30 minutes to 4 hours as described in, for example, JP-A-2009-037108 may be added in order to inhibit any aggregation, etc. of the resin after the preparation of the composition.

The weight average molecular weight of the resin (A) for use in the composition of the present invention, in terms of polystyrene-equivalent value measured by GPC, is preferably in the range of 1000 to 200,000. It is more preferably in the range of 2000 to 100,000, further more preferably 3000 to 70,000 and most preferably 5000 to 50,000. By regulating the weight average molecular weight so as to fall within the range of 1000 to 200,000, not only can any deteriorations of heat resistance and dry etching resistance be prevented but also any deterioration of developability and any increase of viscosity leading to poor film forming property can be prevented.

The polydispersity index (molecular weight distribution) of the resin is generally in the range of 1.0 to 3.0, preferably 1.0 to 2.6, more preferably 1.2 to 2.4 and most preferably 1.4 to 2.2. When the molecular weight distribution satisfies these ranges, excellent resolution and resist shape can be attained, and the side wall of the resist pattern is smooth to thereby ensure excellent roughness characteristics.

In the actinic-ray- or radiation-sensitive resin composition of the present invention, the content of resin (A) in the whole composition is preferably in the range of 30 to 99 mass %, more preferably 60 to 95 mass %, based on the total solids of the composition.

In the present invention, one type of rein (A) may be used alone, or two or more types thereof may be used in combination.

Moreover, in the actinic-ray- or radiation-sensitive resin composition of the present invention, an acid-decomposable resin (resin that when acted on by an acid, increases its polarity, thereby decreasing its solubility in a developer comprising an organic solvent) other than the resin (A) may be contained together with the resin (A). The acid-decomposable resin other than the resin (A) is an acid-decomposable resin comprising a repeating unit similar to the repeating units that may be contained in the resin (A), in which the preferred range of such a repeating unit and the content thereof in the resin are the same as described above in connection with the resin (A).

When the acid-decomposable resin other than the resin (A) is contained, the content of acid-decomposable resin in the composition of the present invention is such that the sum of the contents of resin (A) and acid-decomposable resin other than the resin (A) falls within the above-mentioned range. The mass ratio between resin (A) and acid-decomposable resin other than the resin (A) can be appropriately regulated within the range ensuring the favorable exertion of the effects of the present invention. The mass ratio of [resin (A)/acid-decomposable resin other than the resin (A)] is preferably in the range of 99.9/0.1 to 10/90, more preferably 99.9/0.1 to 60/40.

From the viewpoint of the realization of rectangular profile and high resolution of resist pattern and the realization of etching resistance at dry etching, it is preferred for the actinic-ray- or radiation-sensitive resin composition of the present invention to contain only the resin (A) as an acid-decomposable resin.

[2] Nonionic compound (B) that when exposed to actinic rays or radiation, generates an acid The actinic-ray- or radiation-sensitive resin composition of the present invention comprises a nonionic compound (also referred to as compound (B)) that when exposed to actinic rays or radiation, generates an acid. The use of the nonionic compound as an acid generator makes it feasible to increase the solubility of the composition in a developer comprising an organic solvent, thereby solving the problem of residue defects.

The compound (B) is not particularly limited as long as it is a nonionic acid generator. As the compound (B), there can be mentioned, for example, an imino sulfonate derivative, an oxime sulfonate derivative, a disulfone derivative, a diazosulfone derivative or the like.

It is preferred for the compound (B) to be any of compounds of general formula (B1) below as an imino sulfonate derivative, or any of compounds of general formula (B2) below as an oxime sulfonate derivative.

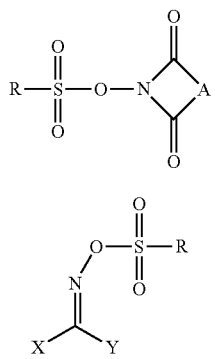

In general formulae (B1) and (B2),

R represents an organic group.

A represents an alkylene group, a cycloalkylene group, an alkenylene group, a cycloalkenylene group or an arylene group.

Each of X and Y independently represents an alkyl group, a cycloalkyl group, an aryl group, a cyano group or a nitro group, provided that X and Y may be bonded to each other to thereby form a ring.

X or Y of any of compounds of general formula (B2) may be bonded to X or Y of any of other compounds of general formula (B2) via a connecting group or a single bond.

In general formula (B1), the alkylene group represented by A is preferably one having 1 to 12 carbon atoms, more preferably one having 1 to 6 carbon atoms. As specific examples of the alkylene groups represented by A, there can be mentioned a methylene group, an ethylene group, a propylene group, an isopropylene group, a butylene group, an isobutylene group and the like.

The cycloalkylene group represented by A may have a monocyclic structure or a polycyclic structure. The cycloalkylene group is preferably one having 3 to 12 carbon atoms, more preferably one having 5 to 10 carbon atoms. As specific examples of the cycloalkylene groups represented by A, there can be mentioned a cyclopentylene group, a cyclohexylene group, a cycloheptylene group, a cyclooctylene group, a cyclododecylene group, an adamantylene group and the like.

The alkenylene group represented by A is preferably one having 2 to 12 carbon atoms, more preferably one having 2 to 6 carbon atoms. As specific examples of the alkenylene groups represented by A, there can be mentioned an ethynylene group, a propenylene group, a butenylene group and the like.

The cycloalkenylene group represented by A may have a monocyclic structure or a polycyclic structure. The cycloalkenylene group is preferably one having 3 to 12 carbon atoms, more preferably one having 5 to 10 carbon atoms. As specific examples of the cycloalkenylene groups represented by A, there can be mentioned a cyclopropenylene group, a cyclohexenylene group, a cyclooctenylene group, a norbornylene group and the like.

The arylene group represented by A is preferably one having 6 to 10 carbon atoms. As specific examples of the arylene groups represented by A, there can be mentioned a phenylene group, a tolylene group, a naphthylene group and the like.

Each of the cycloalkylene group and cycloalkenylene group represented by A may contain a heteroatom, such as a nitrogen atom, an oxygen atom or a sulfur atom, as a ring member.

Substituents may further be introduced in the alkylene group, cycloalkylene group, alkenylene group, cycloalkenylene group and arylene group represented by A. As such further substituents, there can be mentioned an alkyl group (for example, 1 to 15 carbon atoms), a cycloalkyl group (for example, 3 to 15 carbon atoms), an aryl group (for example, 6 to 14 carbon atoms), an alkoxy group (for example, 1 to 15 carbon atoms), a halogen atom, a hydroxyl group, an alkylamido group (for example, 1 to 15 carbon atoms), an alkylthio group (for example, 1 to 15 carbon atoms), an arylthio group (for example, 6 to 14 carbon atoms) and the like.

In general formula (B2), each of the alkyl groups represented by X and Y may be linear or branched. The alkyl group is preferably one having 1 to 15 carbon atoms, more preferably 1 to 5 carbon atoms. As specific examples of the alkyl groups represented by X and Y, there can be mentioned a methyl group, an ethyl group, a propyl group, an n-butyl group, a sec-butyl group, a t-butyl group and the like.

Each of the cycloalkyl groups represented by X and Y may have a monocyclic structure or a polycyclic structure. The cycloalkyl group is preferably one having 3 to 15 carbon atoms, more preferably one having 3 to 10 carbon atoms. As specific examples of the cycloalkyl groups represented by X and Y, there can be mentioned a cyclopropyl group, a cyclobutyl group, a cyclohexyl group and the like.

Each of the aryl groups represented by X and Y is preferably one having 6 to 15 carbon atoms. As specific examples of the aryl groups represented by X and Y, there can be mentioned a phenyl group, a naphthyl group, a fluorenyl group and the like.

As the ring optionally formed by the mutual bonding of X and Y, there can be mentioned, for example, a hydrocarbon ring or a heteroring. The ring optionally formed by the mutual bonding of X and Y is preferably a 5- or 6-membered ring.

As appropriate particular examples of the rings optionally formed by the mutual bonding of X and Y, there can be mentioned a cyclohexane ring, a 1,2,3,4-tetrahydronaphthalene ring, a 2,5-dihydro-5-[(2-methylphenyl)(cyano)methylene]thiophene ring and the like.

Preferably, X is a fluoroalkyl group, a cyano group or a nitro group, while Y is an alkyl group or an aryl group. More preferably, X is a fluoroalkyl group or a cyano group, while Y is an aryl group.

Substituents may further be introduced in the alkyl group, cycloalkyl group and aryl group represented by X and Y. As such further substituents, there can be mentioned those set forth above as being introducible in the alkylene group, etc. represented by A.

A substituent may further be introduced in the ring formed by the mutual bonding of X and Y. As such a further substituent, there can be mentioned not only any of those set forth above as being introducible in the alkylene group, etc. represented by A but also an aryl(cyano)methylene group (for example, 8 to 15 carbon atoms), an alkylaryl(cyano)methylene group (for example, 9 to 20 carbon atoms) or the like. Two substituents may further be introduced in the ring formed by the mutual bonding of X and Y, which two substituents may be bonded to each other to thereby further form a ring. As such a further ring, there can be mentioned a saturated or unsaturated hydrocarbon ring, or a saturated or unsaturated heteroring. It is preferred for this ring to be a 5- or 6-membered ring.

X or Y of any of compounds of general formula (B2) may be bonded to X or Y of any of other compounds of general formula (B2) via a connecting group. In that instance, as the connecting group, there can be mentioned, for example, —COO—, —CO—, —O—, —S—, —SO—, —SO$_2$—, an alkylene group, a cycloalkylene group, an alkenylene group or a group comprised of a combination of these. The number of atoms constituting the connecting group is preferably in the range of 1 to 20.

A substituent may further be introduced in the connecting group. As such a further substituent, there can be mentioned any of those set forth above as being introducible in the alkylene group, etc. represented by A.

In general formulae (B1) and (B2) above, as the organic group represented by R, there can be mentioned, for example, an alkyl group, any of groups of general formula (I) to be described hereinafter, or the like. The alkyl group represented by R may be linear or branched. The alkyl group is preferably one having 1 to 15 carbon atoms, more preferably 1 to 5 carbon atoms. As specific examples of the alkyl groups represented by R, there can be mentioned a methyl group, an ethyl group, a propyl group, an n-butyl group, a sec-butyl group, a t-butyl group and the like.

A substituent may further be introduced in the alkyl group represented by R. As such a further substituent, there can be mentioned a cycloalkyl group (for example, 3 to 15 carbon atoms), an aryl group (for example, 6 to 14 carbon atoms), an alkoxy group (for example, 1 to 15 carbon atoms), a halogen atom, a hydroxyl group, or the like. A fluorine atom is especially preferred.

The alkyl group represented by R is preferably a fluoroalkyl group (preferably having 1 to 15 carbon atoms, more preferably 1 to 5 carbon atoms). This causes the sulfonic acid generated in exposed areas to be a strong acid, thereby enhancing the sensitivity. As a result, not only can EL and DOF be enhanced, but also LWR and residue defects can be reduced.

It is preferred for the fluoroalkyl group represented by R to be a perfluoroalkyl group.

The organic group represented by R is preferably any of groups of general formula (BI) below. The cyclic organic group represented by Cy in general formula (BI) is bulky as compared with a chain group, thereby easing the retention of the sulfonic acid generated in exposed areas in the exposed areas. Therefore, the probability of the occurrence of unintended reaction due to the diffusion of acid to nonexposed areas can be lowered. As a result, not only can EL and DOF be enhanced, but also LWR and residue defects can be reduced.

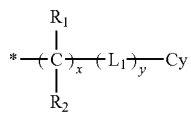

(BI)

In general formula (BI), each of $R_1$ and $R_2$ independently represents a hydrogen atom, a fluorine atom or an alkyl group. Two or more $R_1$s, and $R_2$s may be identical to or different from each other.

$L_1$ represents a bivalent connecting group. Two or more $L_1$s may be identical to or different from each other.

Cy represents a cyclic organic group;

x is an integer of 0 to 20, and y is an integer of 0 to 10.

* represents a bonding hand to a sulfonyl group.

Substituents (preferably a fluorine atom) may be introduced in the alkyl groups represented by $R_1$ and $R_2$. The alkyl group is preferably one having 1 to 4 carbon atoms. A perfluoroalkyl group having 1 to 4 carbon atoms is more preferred. As particular examples of the alkyl groups represented by $R_1$ and $R_2$, there can be mentioned $CF_3$, $C_2F_5$, $C_3F_7$, $C_4F_9$, $C_5F_{11}$, $C_6F_{13}$, $C_7F_{15}$, $C_8F_{17}$, $CH_2CF_3$, $CH_2CH_2CF_3$, $CH_2C_2F_5$, $CH_2CH_2C_2F_5$, $CH_2C_3F_7$, $CH_2CH_2C_3F_7$, $CH_2C_4F_9$ and $CH_2CH_2C_4F_9$. Of these, $CF_3$ is preferred.

It is preferred for each of $R_1$ and $R_2$ to be a fluorine atom or $CF_3$.

$L_1$ is not particularly limited. As the same, there can be mentioned —COO—, —OCO—, —CO—, —O—, —S—, —SO—, —SO$_2$—, an alkylene group, a cycloalkylene group, an alkenylene group or the like. The number of atoms constituting $L_1$ is preferably in the range of 1 to 20, more preferably 1 to 3. Of these groups, —COO—, —OCO—, —CO— and —O— are preferred. —COO— and —OCO— are more preferred.

The cyclic organic group represented by Cy is not particularly limited. For example, there can be mentioned an alicyclic group, an aryl group, a heterocyclic group (aromatic heterocycle or nonaromatic heterocycle, including, for example, tetrahydropyran ring and lactone ring structures), or the like.

The alicyclic group represented by Cy may be monocyclic or polycyclic. As preferred alicyclic groups, there can be mentioned a monocycloalkyl group, such as a cyclopentyl group, a cyclohexyl group or a cyclooctyl group, and a polycycloalkyl group, such as a norbornyl group, a norbornan-1-yl group, a tricyclodecanyl group, a tetracyclodecanyl group, a tetracyclododecanyl group or an adamantyl group. Of these, alicyclic groups with a bulky structure having at least 7 carbon atoms, selected from among a norbornyl group, a tricyclodecanyl group, a tetracyclodecanyl group, a tetracyclododecanyl group and an adamantyl group, are preferred from the viewpoint of inhibition of any in-film diffusion in the PEB (post-exposure bake) operation and enhancement of MEEF (Mask Error Enhancement Factor).

As the aryl groups represented by Cy, there can be mentioned a benzene ring, a naphthalene ring, a phenanthrene ring and an anthracene ring. Of these, a naphthalene ring exhibiting a relatively low light absorbance at 193 nm is preferred.

The heterocyclic group represented by Cy may have a monocyclic structure or a polycyclic structure. As the heterocyclic group, there can be mentioned, for example, any of those derived from a furan ring, a thiophene ring, a benzofuran ring, a benzothiophene ring, a dibenzofuran ring, a dibenzothiophene ring, a pyridine ring, a piperidine ring and a decahydroisoquinoline ring. Of these, those derived from a furan ring, a thiophene ring, a pyridine ring, a piperidine ring and a decahydroisoquinoline ring are preferred.

Further, as the cyclic organic group, there can be mentioned a lactone structure. As particular examples of lactone structures, there can be mentioned those of general formulae (LC1-1) to (LC1-17) above optionally contained in the resin (A).

A substituent may be introduced in the above cyclic organic group. As the substituent, there can be mentioned a halogen atom, an alkyl group (may be linear or branched, preferably having 1 to 12 carbon atoms), a cycloalkyl group (may be any of a monocycle, a polycycle and a spiro ring, preferably having 3 to 20 carbon atoms), an aryl group (preferably having 6 to 14 carbon atoms), a hydroxyl group, a cyano group, an alkoxy group, an ester bond, an amido bond, a urethane bond, a ureido group, an ether bond, a thioether bond, a sulfonamide bond, a sulfonic ester bond, a group resulting from a combination of two or more selected from among these bonds and groups, or the like. The carbon as a constituent of the cyclic organic group (carbon contributing to ring formation) may be a carbonyl carbon.

In the formula, x is preferably 1 to 12, more preferably 1 to 4 and most preferably 1; and y is preferably 0 to 8, more preferably 0 to 4.

More preferably, the groups of general formula (BI) above are those of general formulae (BII) and (BIII) below.

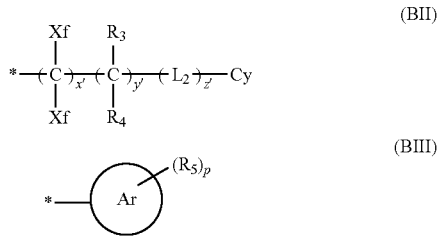

In general formula (BII), each of Xf's independently represents a fluorine atom or an alkyl group substituted with at least one fluorine atom.

Each of $R_3$ and $R_4$ independently represents a hydrogen atom or an alkyl group. Two or more $R_3$s, and $R_4$s may be identical to or different from each other.

$L_2$ represents a bivalent connecting group. Two or more $L_2$'s may be identical to or different from each other.

Cy represents a cyclic organic group; and x' is an integer of 0 to 20, y' is an integer of 0 to 10, and z' is an integer of 0 to 10, provided that $1 \leq x'+y'+z'$.

In general formula (BIII),

Ar represents an aryl group, in which a substituent other than $R_5$ may be introduced.

$R_5$ represents a group containing a hydrocarbon group, and p is an integer of 0 or greater.

In general formulae (BII) and (BIII), * represents a bonding hand to a sulfonyl group.

The groups of general formula (BII) will be described in detail below.

The alkyl group in the alkyl group substituted with a fluorine atom, represented by Xf preferably has 1 to 10 carbon atoms, more preferably 1 to 4 carbon atoms. It is preferred for the alkyl group substituted with a fluorine atom, represented by Xf to be a perfluoroalkyl group.

Xf is preferably a fluorine atom or a perfluoroalkyl group having 1 to 4 carbon atoms. Xf is, for example, a fluorine atom, $CF_3$, $C_2F_5$, $C_3F_7$, $C_4F_9$, $C_5F_{11}$, $C_6F_{13}$, $C_7F_{15}$, $C_8F_{17}$, $CH_2CF_3$, $CH_2CH_2CF_3$, $CH_2C_2F_5$, $CH_2CH_2C_2F_5$, $CH_2C_3F_7$, $CH_2CH_2C_3F_7$, $CH_2C_4F_9$ or $CH_2CH_2C_4F_9$. Of these, a fluorine atom and $CF_3$ are preferred. Most preferably, both Xf's are fluorine atoms.

The alkyl groups represented by $R_3$ and $R_4$ are the same as those represented $R_1$ and $R_2$.

In the formula, x' is preferably an integer of 1 to 10, more preferably 1 to 5;

y' is preferably an integer of 0 to 4, more preferably 0; and z' is preferably an integer of 0 to 8, more preferably 0 to 4.

The bivalent connecting group represented by $L_2$ is not particularly limited, and is the same as any of those represented by $L_1$. (In connection therewith, z' represents the number of repetitions of $L_2$.)

The cyclic organic group represented by Cy is the same as set forth above in connection with general formula (BI).

The groups of general formula (BIII) will be described in detail below.

In general formula (BIII), it is preferred for the aryl group represented by Ar to be an aromatic ring having 6 to 30 carbon atoms.

In particular, Ar is, for example, a benzene ring, a naphthalene ring, a pentalene ring, an indene ring, an azulene ring, a heptalene ring, an indecene ring, a perylene ring, a pentacene ring, an acenaphthalene ring, a phenanthrene ring, an anthracene ring, a naphthalene ring, a chrysene ring, a triphenylene ring, a fluorene ring, a biphenyl ring, a pyrrole ring, a furan ring, a thiophene ring, an imidazole ring, an oxazole ring, a thiazole ring, a pyridine ring, a pyrazine ring, a pyrimidine ring, a pyridazine ring, an indolizine ring, an indole ring, a benzofuran ring, a benzothiophene ring, an isobenzofuran ring, a quinolizine ring, a quinoline ring, a phthalazine ring, a naphthyridine ring, a quinoxaline ring, a quinoxazoline ring, an isoquinoline ring, a carbazole ring, a phenanthridine ring, an acridine ring, a phenanthroline ring, a thianthrene ring, a chromene ring, a xanthene ring, a phenoxathiin ring, a phenothiazine ring or a phenazine ring. Of these, a benzene ring, a naphthalene ring and an anthracene ring are preferred. A benzene ring is more preferred.

A substituent other than $R_5$ may be further introduced in Ar. As the substituent other than $R_5$, there can be mentioned a halogen atom (such as a fluorine atom, a chlorine atom, a bromine atom or an iodine atom), a hydroxyl group, a cyano group, a nitro group, a carboxyl group, or the like. When two or more substituents are introduced, at least two substituents may be bonded to each other to thereby form a ring.

$R_5$ is, for example, an alkoxy group, such as a methoxy group, an ethoxy group or a tert-butoxy group; an aryloxy group, such as a phenoxy group or a p-tolyloxy group; an alkylthioxy group, such as a methylthioxy group, an ethylthioxy group or a tert-butylthioxy group; an arylthioxy group, such as a phenylthioxy group or a p-tolylthioxy group; an alkoxycarbonyl group, such as a methoxycarbonyl group or a butoxycarbonyl group; a phenoxycarbonyl group; an acetoxy group; a linear or branched alkyl group, such as a methyl group, an ethyl group, a propyl group, a butyl group, a heptyl group, a hexyl group, a dodecyl group or a 2-ethylhexyl group; an alkenyl group, such as a vinyl group, a propenyl group or a hexenyl group; an alkynyl group, such as an acetylene group, a propynyl group or a hexynyl group; an aryl group, such as a phenyl group or a tolyl group; an acyl group such as a benzoyl group, an acetyl group or a toluoyl group, or the like.

As the hydrocarbon group contained in the group containing a hydrocarbon group, represented by $R_5$, there can be mentioned, for example, a noncyclic hydrocarbon group or a cycloaliphatic group. The number of carbon atoms thereof is preferably 3 or greater.

In $R_5$, it is preferred for the carbon atom adjacent to Ar to be a tertiary or quaternary carbon atom.

As the noncyclic hydrocarbon group in $R_5$, there can be mentioned an isopropyl group, a t-butyl group, a t-pentyl group, a neopentyl group, a s-butyl group, an isobutyl group, an isohexyl group, a 3,3-dimethylpentyl group, a 2-ethylhexyl group or the like. With respect to the upper limit of the number of carbon atoms of the noncyclic hydrocarbon group, the number is preferably 12 or less, more preferably 10 or less.

As the cycloaliphatic group in $R_5$, there can be mentioned a cycloalkyl group such as a cyclobutyl group, a cyclopentyl group, a cyclohexyl group, a cycloheptyl group or a cyclooctyl group, an adamantyl group, a norbornyl group, a bornyl group, a camphenyl group, a decahydronaphthyl group, a tricyclodecanyl group, a tetracyclodecanyl group, a camphoroyl group, a dicyclohexyl group, a pinenyl group or the like. A substituent may be introduced in the cycloaliphatic group. With respect to the upper limit of the number of carbon atoms of the cycloaliphatic group, the number is preferably 15 or less, more preferably 12 or less.

When a substituent is introduced in the noncyclic hydrocarbon group or cycloaliphatic group, as such a substituent, there can be mentioned, for example, a halogen atom such as a fluorine atom, a chlorine atom, a bromine atom or an iodine atom, an alkoxy group such as a methoxy group, an ethoxy group or a tert-butoxy group, an aryloxy group such as a phenoxy group or a p-tolyloxy group, an alkylthioxy group such as a methylthioxy group, an ethylthioxy group or a tert-butylthioxy group, an arylthioxy group such as a phenylthioxy group or a p-tolylthioxy group, an alkoxycarbonyl group such as a methoxycarbonyl group or a butoxycarbonyl group, a phenoxycarbonyl group, an acetoxy group, a linear or branched alkyl group such as a methyl group, an ethyl group, a propyl group, a butyl group, a heptyl group, a hexyl group, a dodecyl group or a 2-ethylhexyl group, a cycloalkyl group such as a cyclohexyl group, an alkenyl group such as a vinyl group, a propenyl group or a hexenyl group, an alkynyl group such as an acetylene group, a propynyl group or a hexynyl group, an aryl group such as a phenyl group or a tolyl group, a hydroxyl group, a carboxyl group, a sulfonic acid group, a carbonyl group, a cyano group, or the like.

Specific examples of the cycloaliphatic groups and non-cyclic hydrocarbon groups in $R_5$ are shown below.

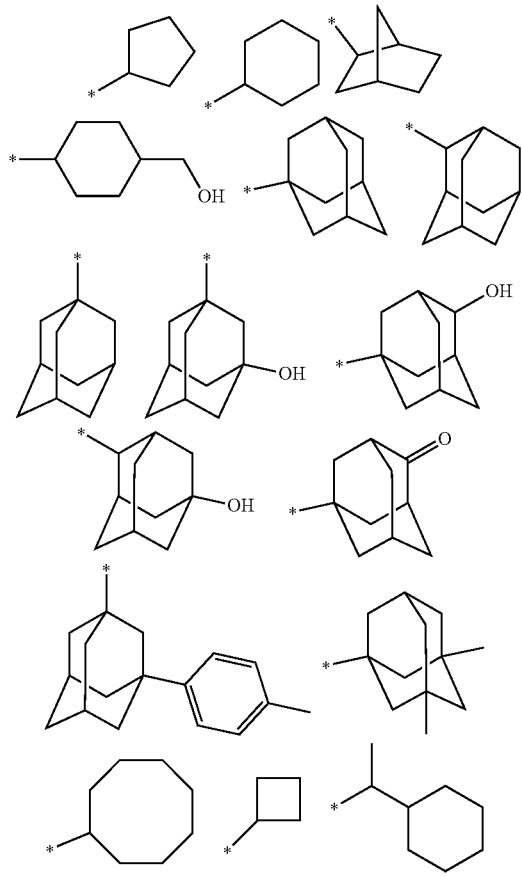

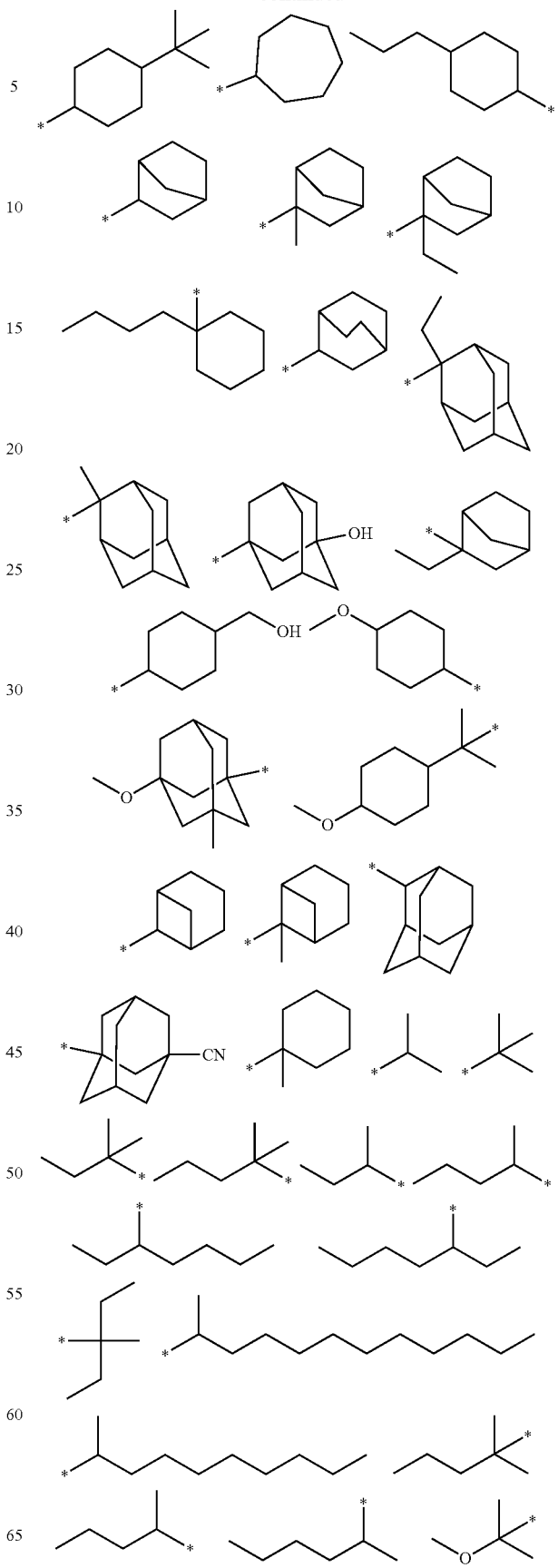

-continued

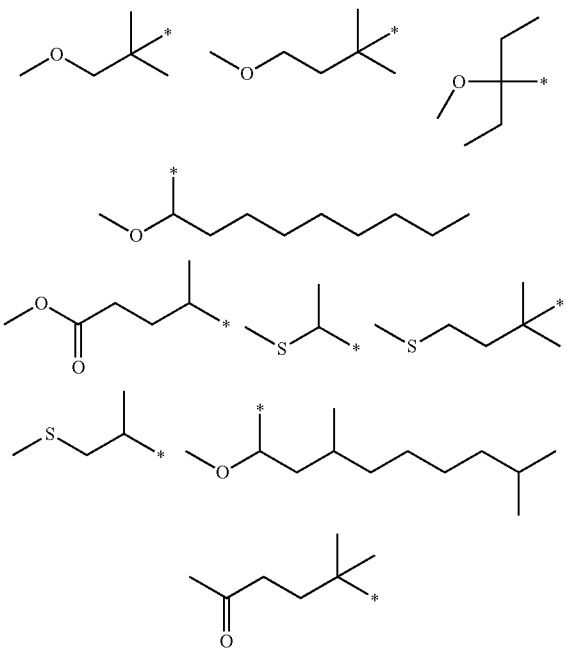

The following structures are preferred among the above from the viewpoint of inhibiting any acid diffusion.

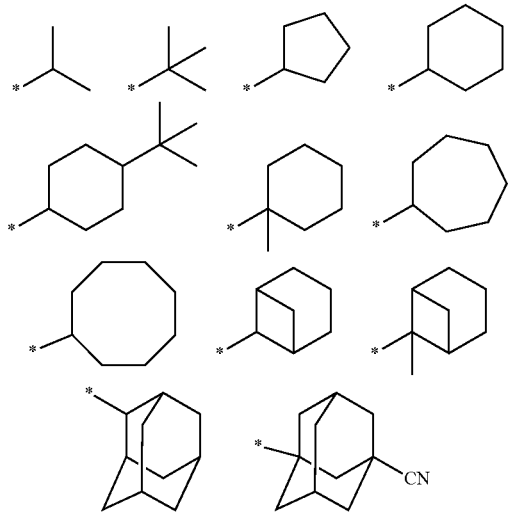

In the formula, p is an integer of 0 or greater. There is no particular upper limit therefor as long as the number is chemically practicable. However, from the viewpoint of inhibiting any acid diffusion, p is generally in the range of 0 to 5, preferably 1 to 4, more preferably 2 or 3 and most preferably 3.

In $R_5$, from the viewpoint of inhibiting any acid diffusion, the structure in which the substitution occurs at an o-position of the aryl ring to the sulfonic acid group is preferred, and the structure in which the substitution occurs at two o-positions is more preferred.

The groups of general formula (BIII) in one form thereof are the groups of general formula (BIII') below.

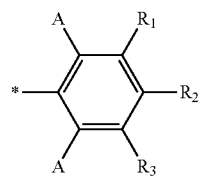

(BIII')

In the formula, A is the same as $R_5$ used in general formula (BIII). Two As may be identical to or different from each other. Each of $R_1$ to $R_3$ independently represents a hydrogen atom, a group containing a hydrocarbon group, a halogen atom, a hydroxyl group, a cyano group or a nitro group. Specific examples of the groups containing a hydrocarbon group are the same as those set forth above.

Among the organic groups of general formulae (BII) and (BIII) above, those of general formula (BII) in which x' is an integer of 1 to 10 are preferred. In this form, the sulfonic acid generated in exposed areas becomes a strong acid, thereby enhancing the sensitivity. As a result, not only can EL and DOE be enhanced, but also LWR and residue defects can be reduced.

Particular examples of the groups of general formula (BI) are shown below.

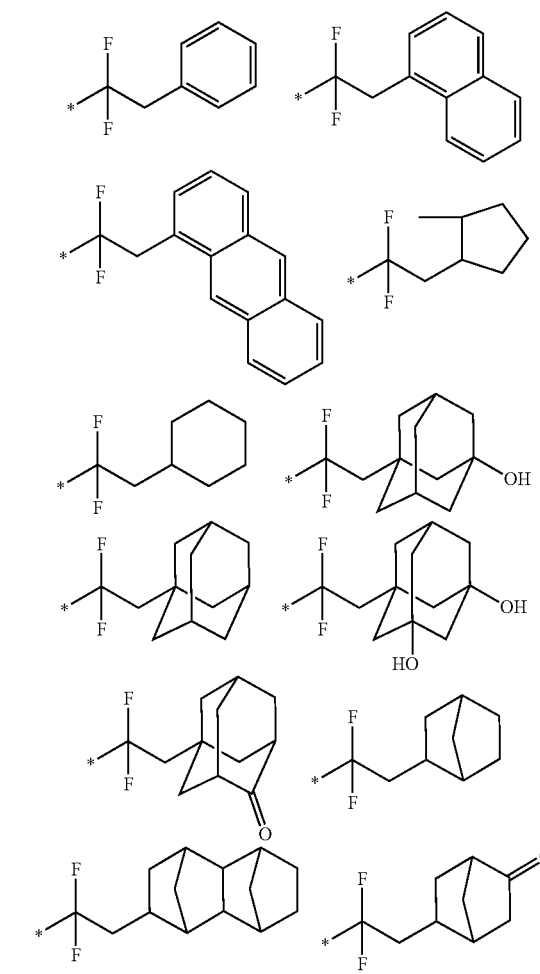

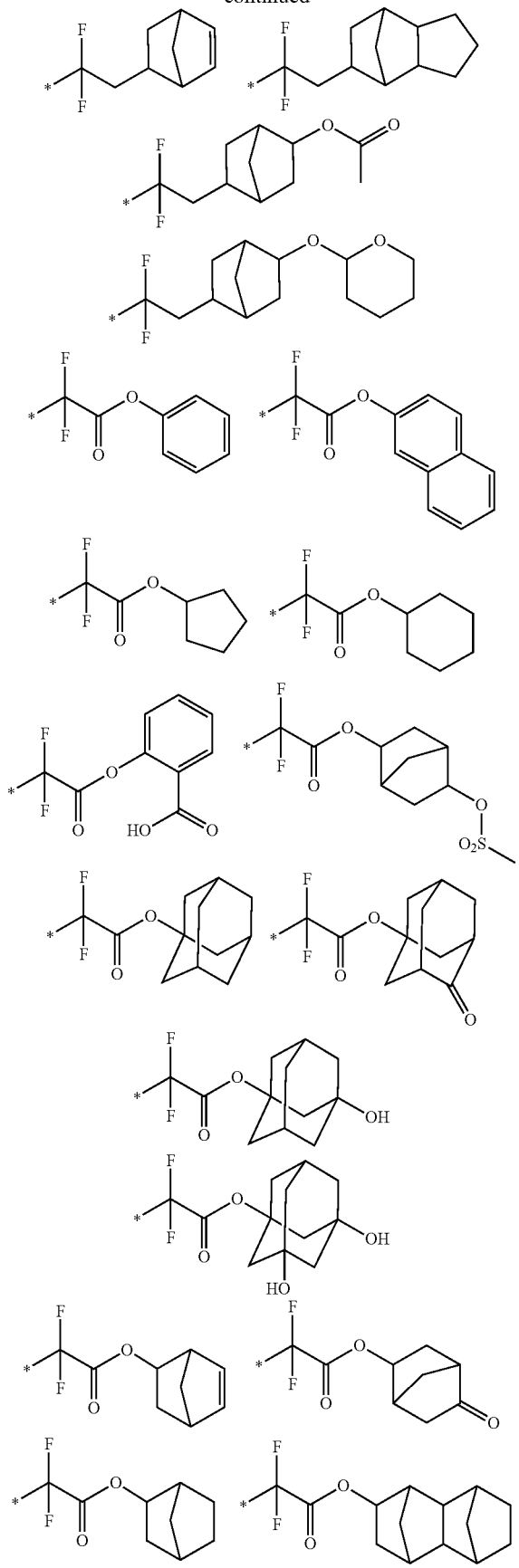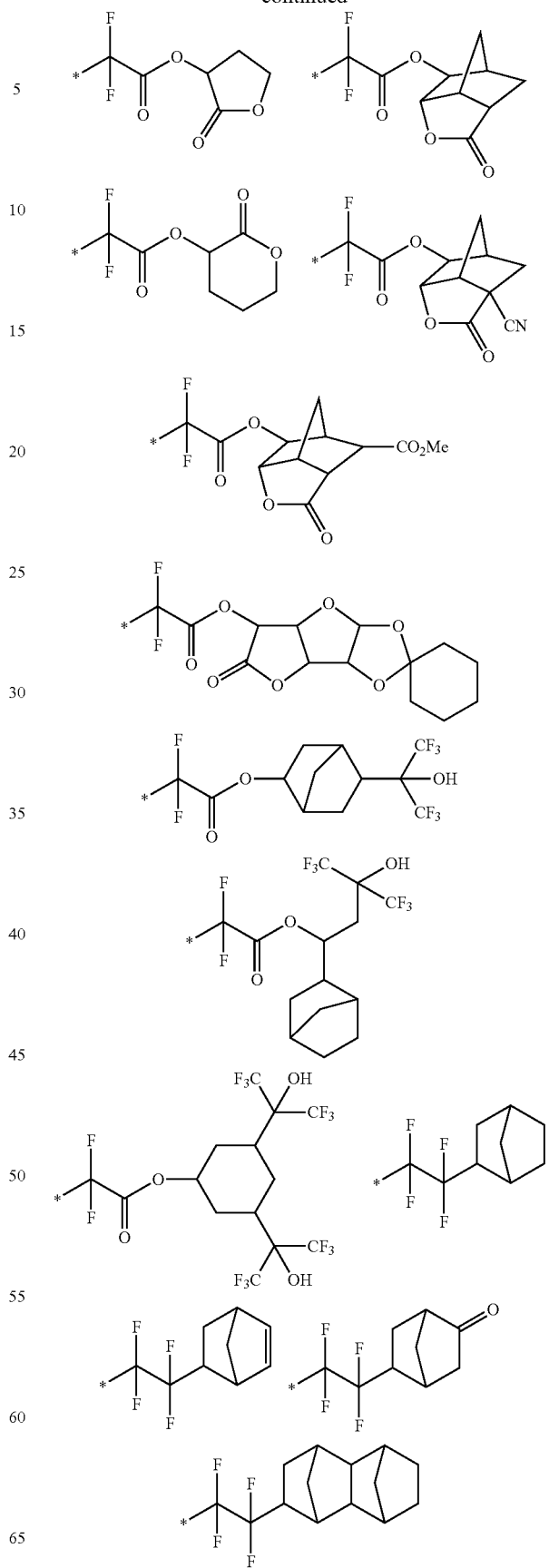

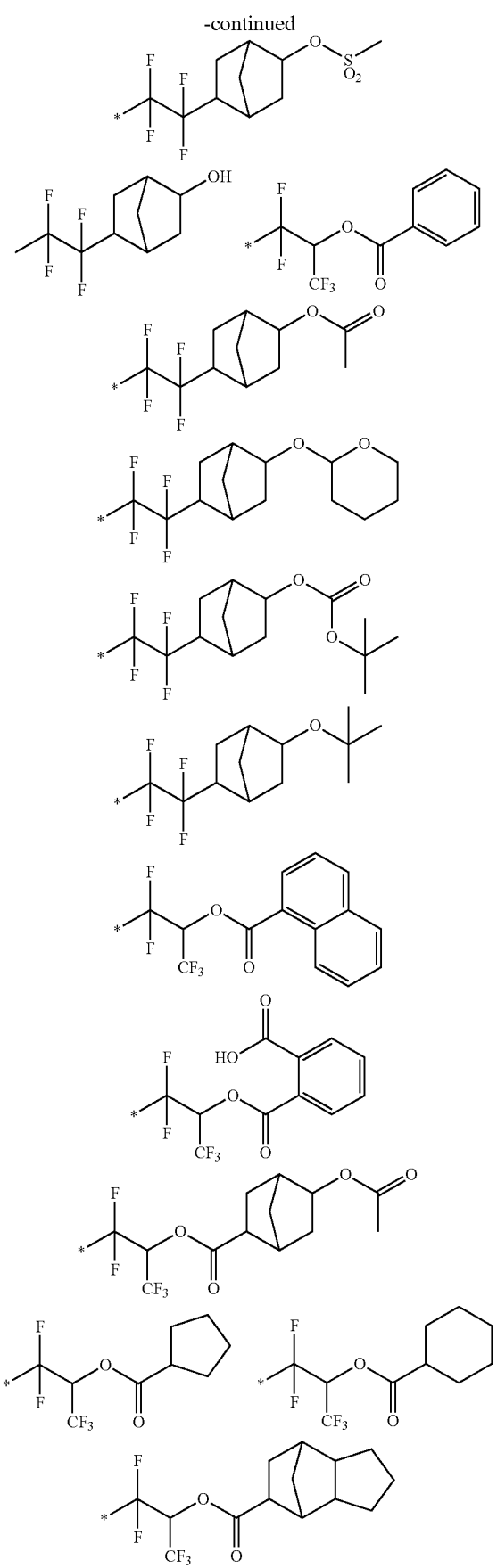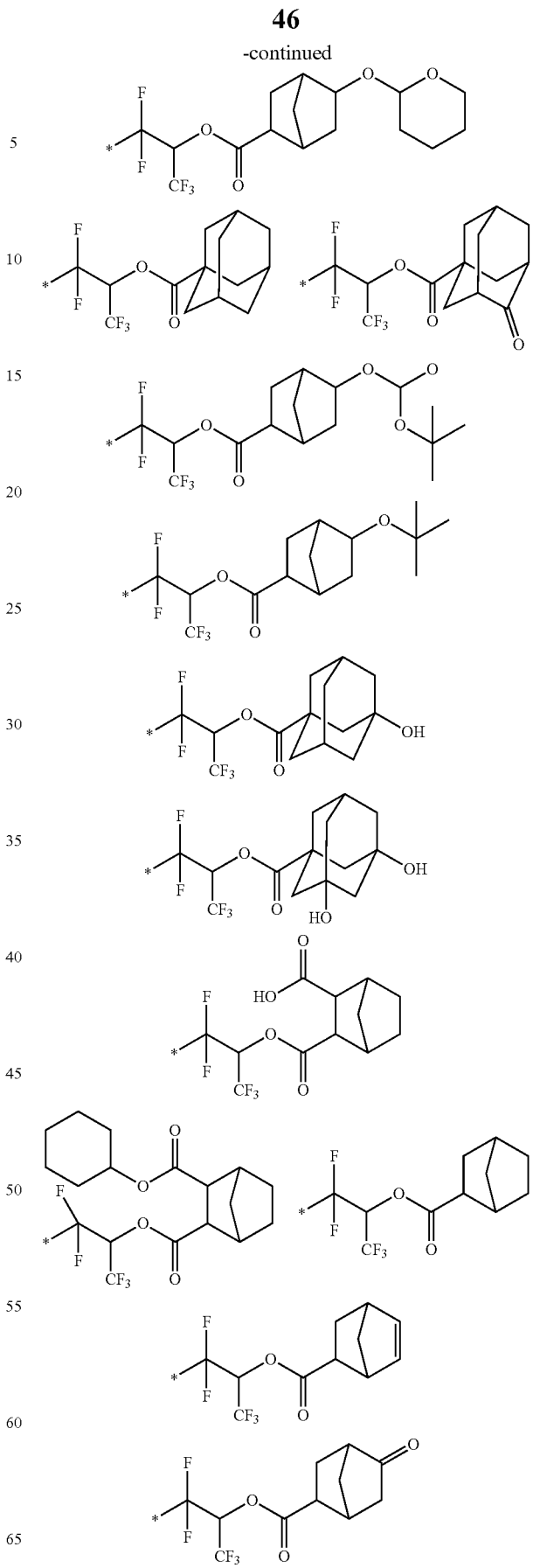

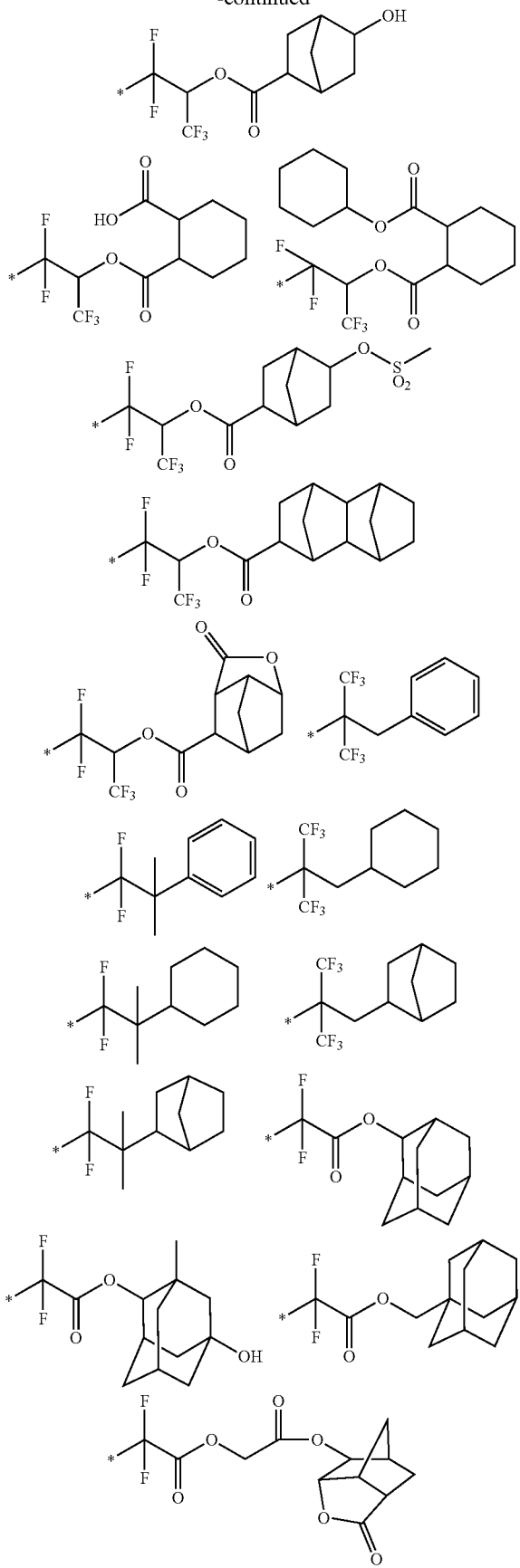

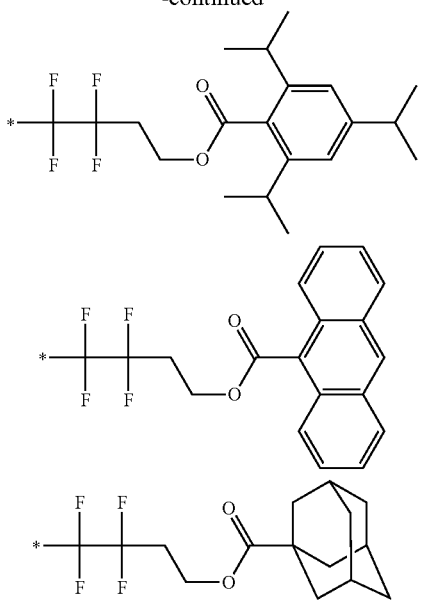

Also, the compound (B) may be any of compounds of general formula (B3) below as a disulfone derivative or any of compounds of general formula (B4) below as a diazosulfone derivative.

$$Ar_1-SO_2-SO_2-Ar_2 \quad (B3)$$

$$Ra_1-\underset{\underset{O}{\|}}{\overset{\overset{O}{\|}}{S}}-\overset{N_2}{C}-\underset{\underset{O}{\|}}{\overset{\overset{O}{\|}}{S}}-Ra_2 \quad (B4)$$

In general formula (B3), each of $Ar_1$ and $Ar_2$ independently represents an aryl group.

In general formula (B4), each of $Ra_1$ and $Ra_2$ independently represents an alkyl group, a cycloalkyl group or an aryl group.

The aryl groups represented by $Ar_1$, $Ar_2$, $Ra_1$ and $Ra_2$ can be those mentioned above as being represented by X and Y of general formula (B2).

The alkyl groups and cycloalkyl groups represented by $Ra_1$ and $Ra_2$ can be those mentioned above as being represented by X and Y of general formula (B2).

Substituents may further be introduced in $Ar_1$, $Ar_2$, $Ra_1$ and $Ra_2$. As such further substituents, there can be mentioned those mentioned above as being introducible in X and Y of general formula (B2).

The molecular weight of the compound (B) is preferably in the range of 100 to 1500, more preferably 200 to 1000.

Nonlimiting particular examples of the compounds (B) are shown below.

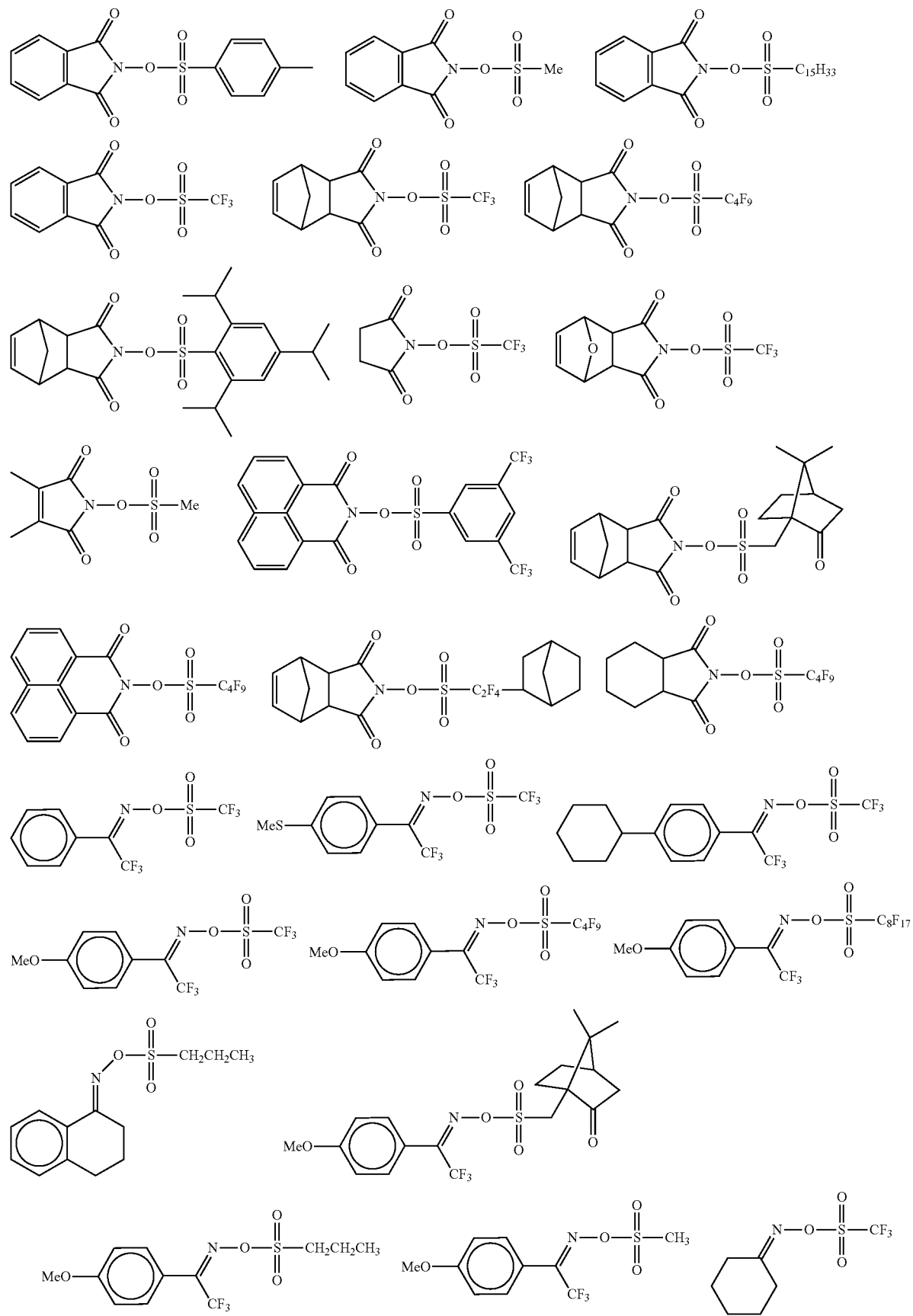

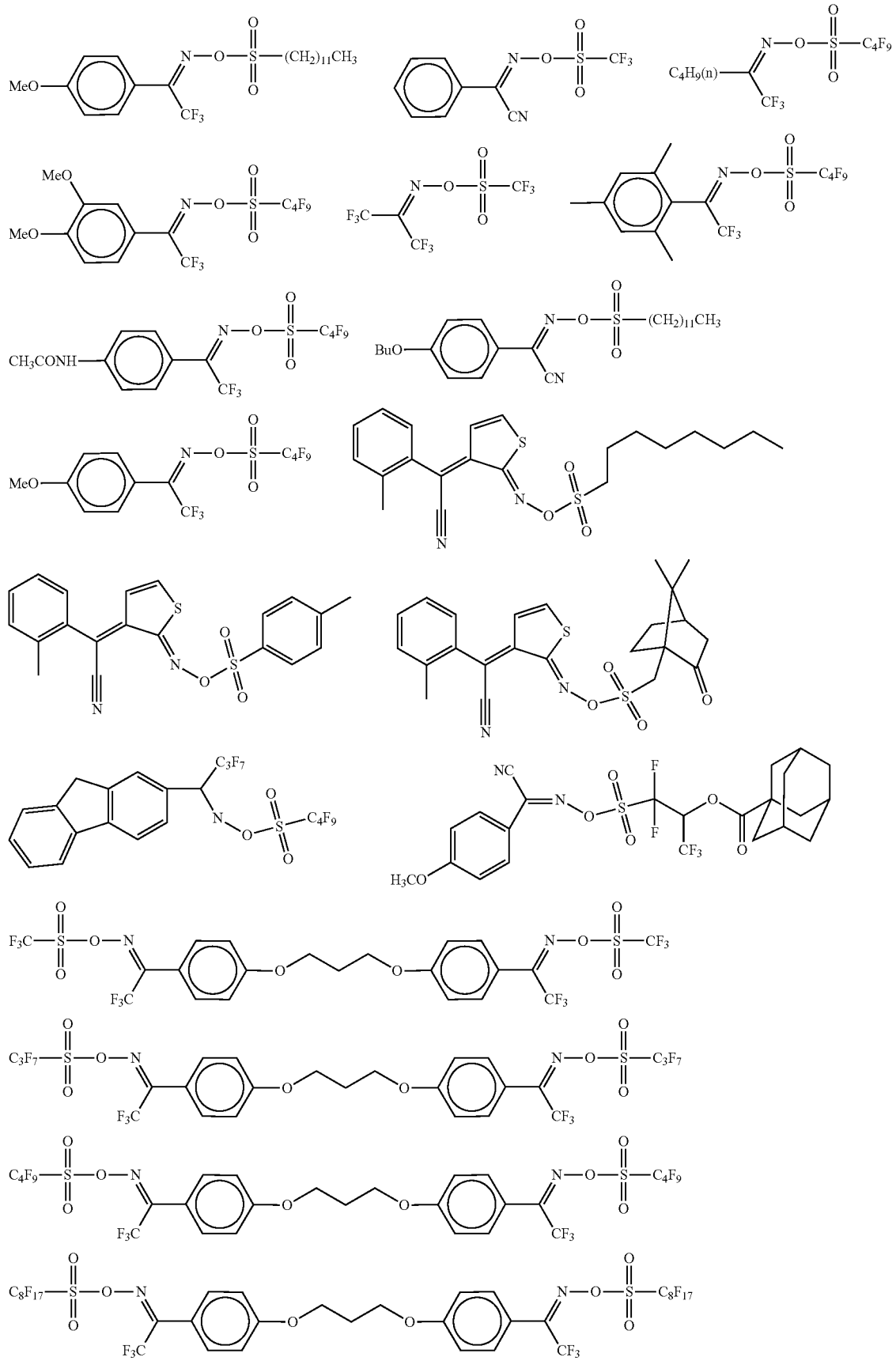

-continued
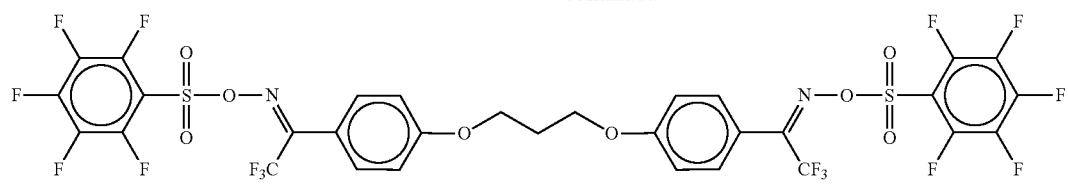
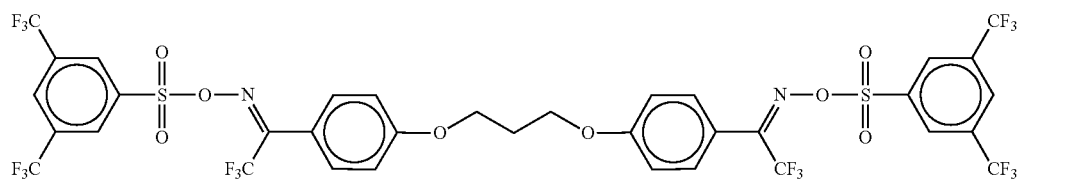
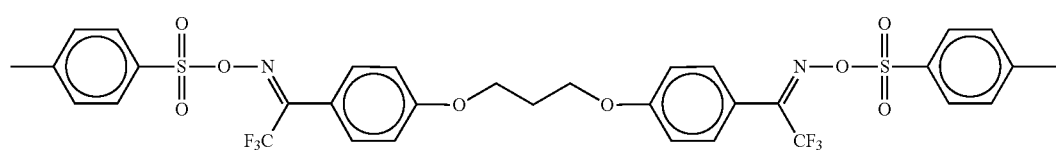
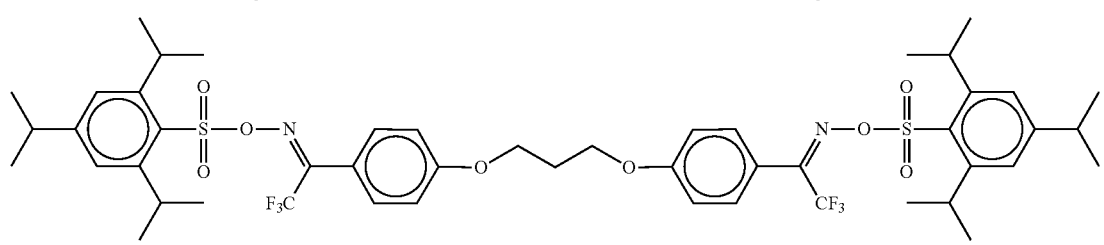
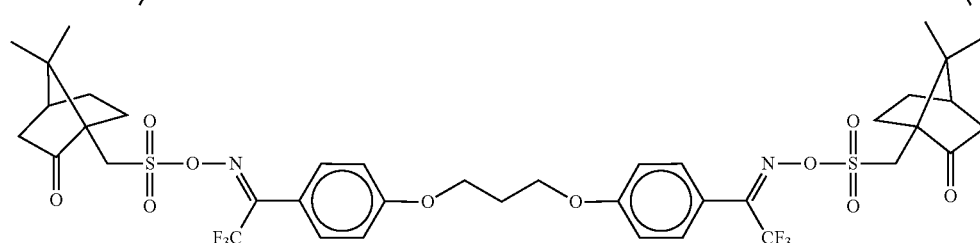
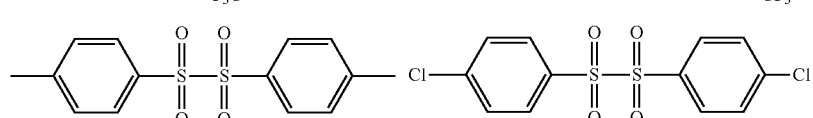
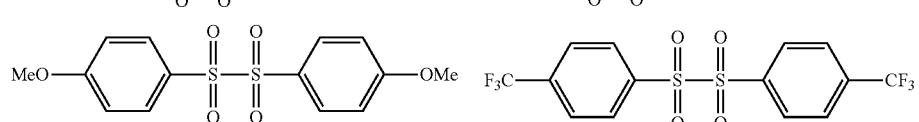
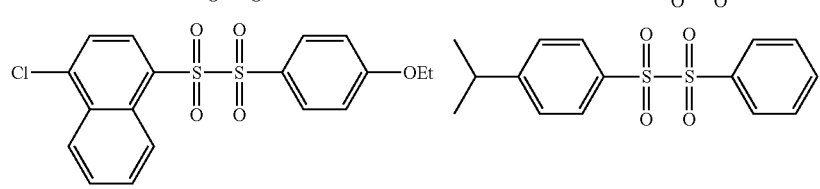
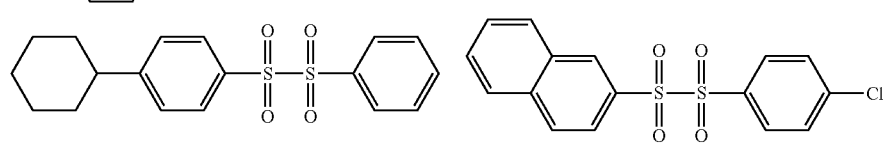
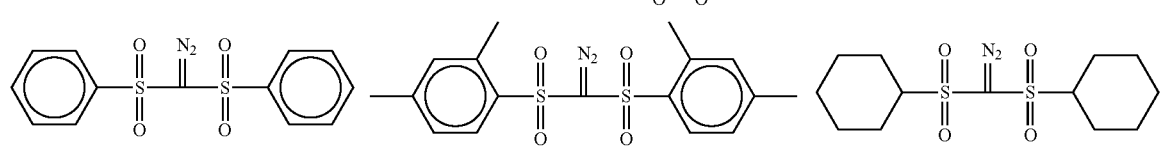

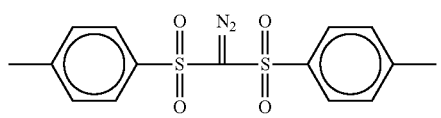 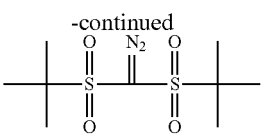

One type of compound (B) may be used alone, or two or more types thereof may be used in combination.

The content of compound (B) in the actinic-ray- or radiation-sensitive resin composition is preferably in the range of 0.1 to 15 mass %, more preferably 0.5 to 13 mass %, further more preferably 1 to 12 mass % and most preferably 4 to 10 mass %, based on the total solids of the composition.

The compound (B) may be used in combination with an acid generator (hereinafter also referred as "compound (B')") other than the compound (B).

The compound (B') is not particularly limited as long as it is a common one. As preferred compounds (B'), there can be mentioned the compounds of general formulae (ZI) and (ZII) below.

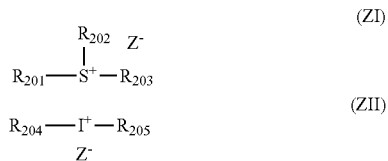

In general formula (ZI), each of $R_{201}$, $R_{202}$ and $R_{203}$ independently represents an organic group.

The number of carbon atoms of each of the organic groups represented by $R_{201}$, $R_{202}$ and $R_{203}$ is generally in the range of 1 to 30, preferably 1 to 20.

Two of $R_{201}$ to $R_{203}$ may be bonded to each other to thereby form a ring structure, and the ring within the same may contain an oxygen atom, a sulfur atom, an ester bond, an amido bond or a carbonyl group. As the group formed by the bonding of two of $R_{201}$ to $R_{203}$, there can be mentioned an alkylene group (for example, a butylene group or a pentylene group).

$Z^-$ represents a normucleophilic anion (anion whose capability of inducing a nucleophilic reaction is markedly low).

As $Z^-$, there can be mentioned, for example, a sulfonate anion (an aliphatic sulfonate anion, an aromatic sulfonate anion, a camphor sulfonate anion or the like), a carboxylate anion (an aliphatic carboxylate anion, an aromatic carboxylate anion, an aralkyl carboxylate anion or the like), a sulfonylimide anion, a bis(alkylsulfonyl)imide anion, a tris(alkylsulfonyl)methide anion or the like.

The aliphatic moiety in the aliphatic sulfonate anion and aliphatic carboxylate anion may be an alkyl group or a cycloalkyl group, being preferably a linear or branched alkyl group having 1 to 30 carbon atoms or a cycloalkyl group having 3 to 30 carbon atoms.

As a preferred aromatic group in the aromatic sulfonate anion and aromatic carboxylate anion, there can be mentioned an aryl group having 6 to 14 carbon atoms, for example, a phenyl group, a tolyl group, a naphthyl group or the like.

Substituents may be introduced in the above-mentioned alkyl group, cycloalkyl group and aryl group. As particular examples of the substituents, there can be mentioned a nitro group, a halogen atom such as a fluorine atom, a carboxyl group, a hydroxyl group, an amino group, a cyano group, an alkoxy group (preferably having 1 to 15 carbon atoms), a cycloalkyl group (preferably having 3 to 15 carbon atoms), an aryl group (preferably having 6 to 14 carbon atoms), an alkoxycarbonyl group (preferably having 2 to 7 carbon atoms), an acyl group (preferably having 2 to 12 carbon atoms), an alkoxycarbonyloxy group (preferably having 2 to 7 carbon atoms), an alkylthio group (preferably having 1 to 15 carbon atoms), an alkylsulfonyl group (preferably having 1 to 15 carbon atoms), an alkyliminosulfonyl group (preferably having 2 to 15 carbon atoms), an aryloxysulfonyl group (preferably having 6 to 20 carbon atoms), an alkylaryloxysulfonyl group (preferably having 7 to 20 carbon atoms), a cycloalkylaryloxysulfonyl group (preferably having 10 to 20 carbon atoms), an alkyloxyalkyloxy group (preferably having 5 to 20 carbon atoms), a cycloalkylalkyloxyalkyloxy group (preferably having 8 to 20 carbon atoms) and the like. With respect to the aryl group or ring structure of each of these groups, as its substituent, there can further be mentioned an alkyl group (preferably having 1 to 15 carbon atoms).

As a preferred aralkyl group in the aralkyl carboxylate anion, there can be mentioned an aralkyl group having 6 to 12 carbon atoms, for example, a benzyl group, a phenethyl group, a naphthylmethyl group, a naphthylethyl group, a naphthylbutyl group or the like.

As the sulfonylimide anion, there can be mentioned, for example, a saccharin anion.

The alkyl group in the bis(alkylsulfonyl)imide anion and tris(alkylsulfonyl)methide anion is preferably an alkyl group having 1 to 5 carbon atoms. As substituents introducible in these alkyl groups, there can be mentioned a halogen atom, an alkyl group substituted with a halogen atom, an alkoxy group, an alkylthio group, an alkyloxysulfonyl group, an aryloxysulfonyl group, a cycloalkylaryloxysulfonyl group and the like. A fluorine atom and an alkyl group substituted with a fluorine atom are preferred.

As other $Z^-$, there can be mentioned, for example, phosphorus fluoride, boron fluoride, antimony fluoride or the like.

$Z^-$ is preferably an aliphatic sulfonate anion substituted at its at least α-position of sulfonic acid with a fluorine atom, an aromatic sulfonate anion substituted with a fluorine atom or a group containing a fluorine atom, a bis(alkylsulfonyl)imide anion whose alkyl group is substituted with a fluorine atom, or a tris(alkylsulfonyl)methide anion whose alkyl group is substituted with a fluorine atom. More preferably, $Z^-$ as a normucleophilic anion is a perfluorinated aliphatic sulfonate anion (further more preferably having 4 to 8 carbon atoms) or a benzenesulfonate anion containing a fluorine atom. Further more preferably, the normucleophilic anion is a nonafluorobutanesulfonate anion, a perfluorooctanesulfonate anion, a pentafluorobenzenesulfonate anion or a 3,5-bis(trifluoromethyl)benzenesulfonate anion.

From the viewpoint of acid strength, it is preferred for the pKa value of generated acid to be −1 or less so as to ensure a sensitivity enhancement.

As the organic groups represented by $R_{201}$, $R_{202}$ and $R_{203}$, there can be mentioned an aryl group (preferably having 6 to 15 carbon atoms), a linear or branched alkyl group (preferably having 1 to 10 carbon atoms), a cycloalkyl group (preferably having 3 to 15 carbon atoms) and the like.

Preferably, at least one of $R_{201}$, $R_{202}$ and $R_{203}$ is an aryl group. More preferably, these three are simultaneously aryl groups. The aryl groups include not only a phenyl group, a naphthyl group and the like but also heteroaryl groups, such as an indole residue and a pyrrole residue. Substituents may further be introduced in these aryl groups. As the substituents, there can be mentioned a nitro group, a halogen atom such as a fluorine atom, a carboxyl group, a hydroxyl group, an amino group, a cyano group, an alkoxy group (preferably having 1 to 15 carbon atoms), a cycloalkyl group (preferably having 3 to 15 carbon atoms), an aryl group (preferably having 6 to 14 carbon atoms), an alkoxycarbonyl group (preferably having 2 to 7 carbon atoms), an acyl group (preferably having 2 to 12 carbon atoms), an alkoxycarbonyloxy group (preferably having 2 to 7 carbon atoms) and the like. The appropriate substituents are not limited to these.

Two selected from among $R_{201}$, $R_{202}$ and $R_{203}$ may be bonded via a single bond or a connecting group to each other. The connecting group may be any of an alkylene group (preferably having 1 to 3 carbon atoms), —O—, —S—, —CO—, —SO$_2$— and the like. These are however nonlimiting.

As preferred structures in which at least one of and $R_{203}$ is not an aryl group, there can be $R_{201}$, $R_{202}$ mentioned the cation structures of the compounds set forth in Sections 0046 and 0047 of JP-A-2004-233661, compounds set forth in Sections 0040 to 0046 of JP-A-2003-35948, compounds of formulae (I-1) to (1-70) shown as examples in US 2003/0224288 A1, compounds of formulae (IA-1) to (IA-54) and (IB-1) to (IB-24) shown as examples in US 2003/0077540 A1 and the like.

In general formula (ZII), each of $R_{204}$ and $R_{205}$ independently represents an aryl group, an alkyl group or a cycloalkyl group.

These aryl, alkyl and cycloalkyl groups represented by $R_{204}$ and $R_{205}$ are the same as set forth above in connection with $R_{201}$ to $R_{203}$ of the compounds (ZI).

Substituents may further be introduced in the aryl, alkyl and cycloalkyl groups represented by $R_{204}$ and $R_{205}$. The substituents are also the same as those introducible in the aryl, alkyl and cycloalkyl groups represented by $R_{201}$ to $R_{203}$ of the compounds (ZI).

$Z^-$ represents a normucleophilic anion, which is the same as that represented by $Z^-$ in general formula (ZI).

Most preferred examples of the compounds (B') are shown below.

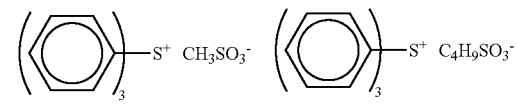
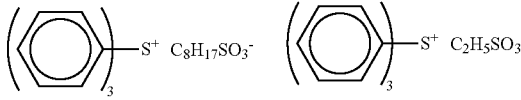
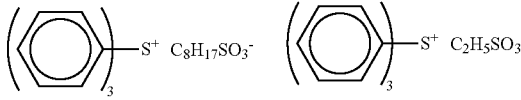
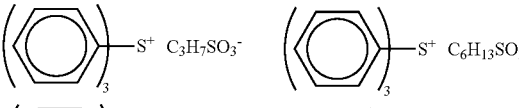
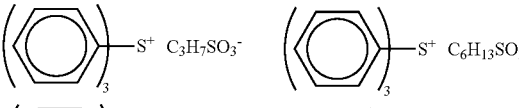
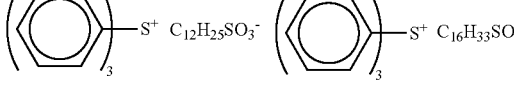
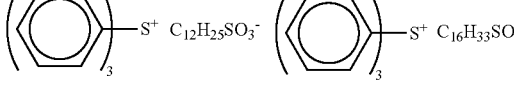

-continued

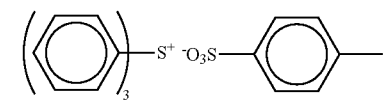
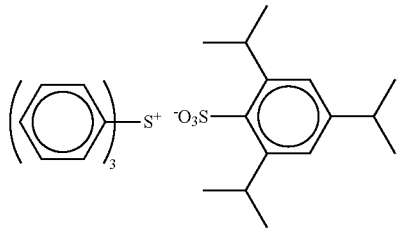
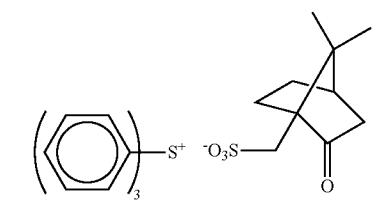
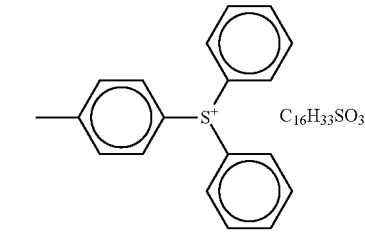
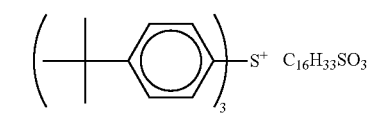
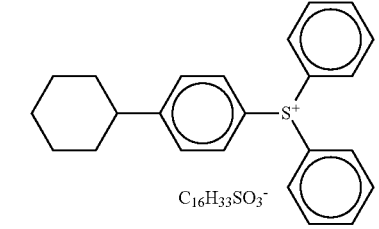
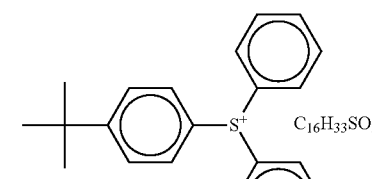
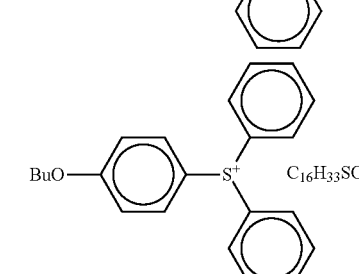
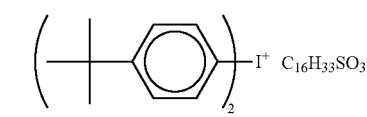

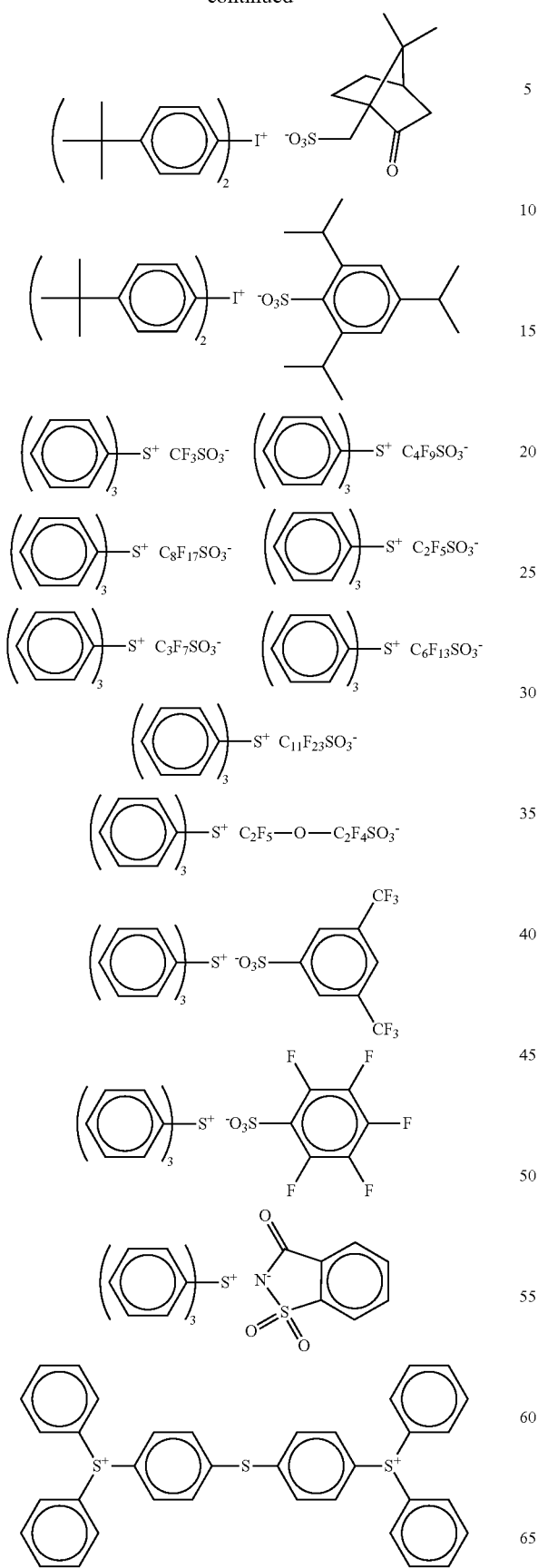
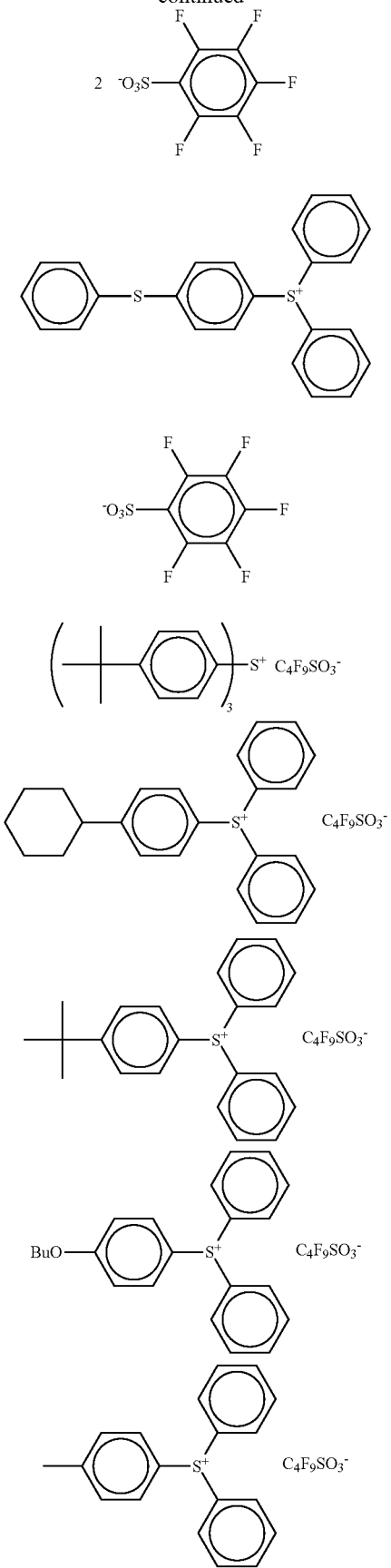

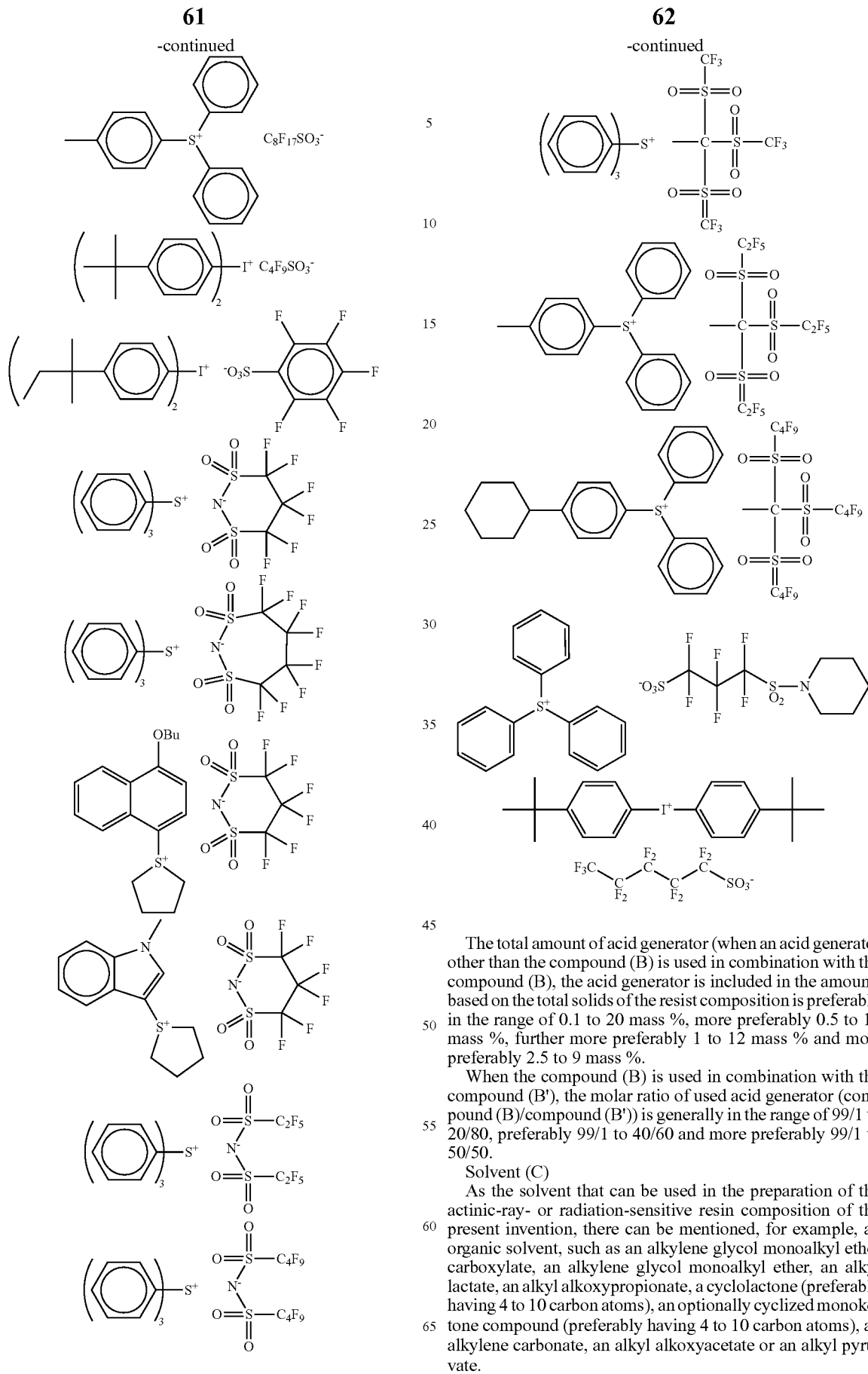

The total amount of acid generator (when an acid generator other than the compound (B) is used in combination with the compound (B), the acid generator is included in the amount) based on the total solids of the resist composition is preferably in the range of 0.1 to 20 mass %, more preferably 0.5 to 17 mass %, further more preferably 1 to 12 mass % and most preferably 2.5 to 9 mass %.

When the compound (B) is used in combination with the compound (B'), the molar ratio of used acid generator (compound (B)/compound (B')) is generally in the range of 99/1 to 20/80, preferably 99/1 to 40/60 and more preferably 99/1 to 50/50.

Solvent (C)

As the solvent that can be used in the preparation of the actinic-ray- or radiation-sensitive resin composition of the present invention, there can be mentioned, for example, an organic solvent, such as an alkylene glycol monoalkyl ether carboxylate, an alkylene glycol monoalkyl ether, an alkyl lactate, an alkyl alkoxypropionate, a cyclolactone (preferably having 4 to 10 carbon atoms), an optionally cyclized monoketone compound (preferably having 4 to 10 carbon atoms), an alkylene carbonate, an alkyl alkoxyacetate or an alkyl pyruvate.

As particular examples of these solvents, there can be mentioned those set forth in Sections [0441] to [0455] of US Patent Application Publication No. 2008/0187860.

In the present invention, a mixed solvent comprised of a mixture of a solvent containing a hydroxyl group in its structure and a solvent containing no hydroxyl group may be used as the organic solvent.

Example compounds mentioned above can be appropriately used as the solvent containing a hydroxyl group and solvent containing no hydroxyl group. The solvent containing a hydroxyl group is preferably an alkylene glycol monoalkyl ether, an alkyl lactate or the like, more preferably propylene glycol monomethyl ether (PGME, also known as 1-methoxy-2-propanol) or ethyl lactate. The solvent containing no hydroxyl group is preferably an alkylene glycol monoalkyl ether acetate, an alkyl alkoxypropionate, an optionally cyclized monoketone compound, a cyclolactone, an alkyl acetate or the like. Of these, propylene glycol monomethyl ether acetate (PGMEA, also known as 1-methoxy-2-acetoxypropane), ethyl ethoxypropionate, 2-heptanone, γ-butyrolactone, cyclohexanone and butyl acetate are especially preferred. Propylene glycol monomethyl ether acetate, ethyl ethoxypropionate and 2-heptanone are most preferred.

The mixing ratio (mass) of a solvent having a hydroxyl group and a solvent having no hydroxyl group is in the range of 1/99 to 99/1, preferably 10/90 to 90/10 and more preferably 20/80 to 60/40. The mixed solvent containing 50 mass % or more of a solvent containing no hydroxyl group is especially preferred from the viewpoint of uniform applicability.

The solvent preferably contains propylene glycol monomethyl ether acetate, more preferably being a solvent comprised only of propylene glycol monomethyl ether acetate or a mixed solvent comprised of two or more types of solvents in which propylene glycol monomethyl ether acetate is contained.

[4] Basic Compound (D)

The actinic-ray- or radiation-sensitive resin composition of the present invention may contain a basic compound (D) so as to decrease any performance alteration over time from exposure to bake.

As preferred basic compounds, there can be mentioned the compounds having the structures of the following formulae (A) to (E).

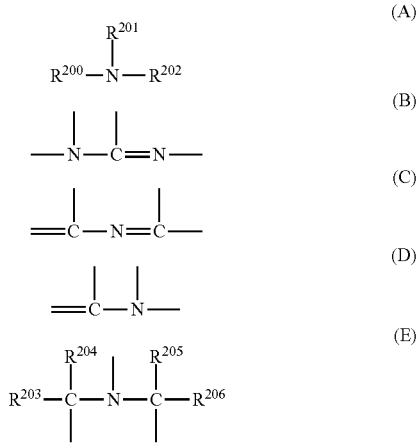

In general formulae (A) and (E), $R^{200}$, $R^{201}$ and $R^{202}$ may be identical to or different from each other and each represent a hydrogen atom, an alkyl group (preferably having 1 to 20 carbon atoms), a cycloalkyl group (preferably having 3 to 20 carbon atoms) or an aryl group (having 6 to 20 carbon atoms). $R^{201}$ and $R^{202}$ may be bonded to each other to thereby form a ring. $R^{203}$, $R^{204}$, $R^{205}$ and $R^{206}$ may be identical to or different from each other and each represent an alkyl group having 1 to 20 carbon atoms.

With respect to these alkyl groups, as a preferred substituted alkyl group, there can be mentioned an aminoalkyl group having 1 to 20 carbon atoms, a hydroxyalkyl group having 1 to 20 carbon atoms or a cyanoalkyl group having 1 to 20 carbon atoms.

More preferably, the alkyl groups in general formulae (A) and (E) are unsubstituted.

As preferred compounds of the formulae, there can be mentioned guanidine, aminopyrrolidine, pyrazole, pyrazoline, piperazine, aminomorpholine, an aminoalkylmorpholine, piperidine and the like. As more preferred compounds, there can be mentioned compounds with an imidazole structure, a diazabicyclo structure, an onium hydroxide structure, an onium carboxylate structure, a trialkylamine structure, an aniline structure or a pyridine structure, alkylamine derivatives having a hydroxyl group and/or an ether bond, aniline derivatives having a hydroxyl group and/or an ether bond, and the like.

As the compounds with an imidazole structure, there can be mentioned imidazole, 2,4,5-triphenylimidazole, benzimidazole and the like. As the compounds with a diazabicyclo structure, there can be mentioned 1,4-diazabicyclo[2,2,2]octane, 1,5-diazabicyclo[4,3,0]non-5-ene, 1,8-diazabicyclo[5,4,0]undec-7-ene and the like. As the compounds with an onium hydroxide structure, there can be mentioned a triarylsulfonium hydroxide, phenacylsulfonium hydroxide, and sulfonium hydroxides having a 2-oxoalkyl group such as triphenylsulfonium hydroxide, tris(t-butylphenyl)sulfonium hydroxide, bis(t-butylphenyl)iodonium hydroxide, phenacylthiophenium hydroxide, 2-oxopropylthiophenium hydroxide and the like. As the compounds with an onium carboxylate structure, there can be mentioned those having a carboxylate at the anion moiety of the compounds with an onium hydroxide structure, for example, an acetate, an adamantane-1-carboxylate, a perfluoroalkyl carboxylate and the like. As the compounds with a trialkylamine structure, there can be mentioned tri(n-butyl)amine, tri(n-octyl)amine and the like. As the compounds with an aniline structure, there can be mentioned 2,6-diisopropylaniline, N,N-dimethylaniline, N,N-dibutylaniline, N,N-dihexylaniline and the like. As the alkylamine derivatives having a hydroxyl group and/or an ether bond, there can be mentioned ethanolamine, diethanolamine, triethanolamine, tris(methoxyethoxyethyl)amine and the like. As the aniline derivatives having a hydroxyl group and/or an ether bond, there can be mentioned N,N-bis(hydroxyethyl)aniline and the like.

As preferred basic compounds, there can be further mentioned an amine compound having a phenoxy group, an ammonium salt compound having a phenoxy group, an amine compound having a sulfonic ester group and an ammonium salt compound having a sulfonic ester group.

Each of the above amine compound having a phenoxy group, ammonium salt compound having a phenoxy group, amine compound having a sulfonic ester group and ammonium salt compound having a sulfonic ester group preferably contains at least one alkyl group bonded to the nitrogen atom thereof. Further preferably, the alkyl group in its chain contains an oxygen atom, thereby forming an oxyalkylene group. The number of oxyalkylene groups in each molecule is one or more, preferably 3 to 9 and more preferably 4 to 6. Among the oxyalkylene groups, the structures of —CH$_2$CH$_2$O—, —CH(CH$_3$)CH$_2$O— and —CH$_2$CH$_2$CH$_2$O— are preferred.

As specific examples of the above amine compound having a phenoxy group, ammonium salt compound having a phenoxy group, amine compound having a sulfonic ester group and ammonium salt compound having a sulfonic ester group, there can be mentioned the compounds (C1-1) to (C3-3) shown as examples in Section [0066] of U.S. Patent Application Publication No. 2007/0224539, which are however nonlimiting.

It is optional for the actinic-ray- or radiation-sensitive resin composition of the present invention to contain a basic compound. When a basic compound is contained, the amount of basic compound used is generally in the range of 0.001 to 10 mass %, preferably 0.01 to 5 mass %, based on the total solids of the actinic-ray- or radiation-sensitive resin composition.

The molar ratio of acid generator to basic compound (acid generator/basic compound) used in the composition is preferably in the range of 2.5 to 300. Namely, a molar ratio of 2.5 or higher is preferred from the viewpoint of the enhancement of sensitivity and resolution. A molar ratio of 300 or below is preferred from the viewpoint of the inhibition of any resolution deterioration due to resist pattern thickening over time until baking treatment after exposure. The molar ratio of acid generator/basic compound is more preferably in the range of 5.0 to 200, further more preferably 7.0 to 150.

[5] Surfactant (E)

It is optional for the actinic-ray- or radiation-sensitive resin composition of the present invention to further contain a surfactant. When a surfactant is contained, it is preferred to contain any one, or two or more members, of fluorinated and/or siliconized surfactants (fluorinated surfactant, siliconized surfactant and surfactant containing both fluorine and silicon atoms).

The actinic-ray- or radiation-sensitive resin composition of the present invention when containing the surfactant would, in the use of an exposure light source of 250 nm or below, especially 220 nm or below, produce a resist pattern of less adhesion and development defects with favorable sensitivity and resolution.

As the fluorinated and/or siliconized surfactants, there can be mentioned those described in section of US Patent Application Publication No. 2008/0248425. For example, there can be mentioned Eftop EF301 and EF303 (produced by Shin-Akita Kasei Co., Ltd.), Florad FC 430, 431 and 4430 (produced by Sumitomo 3M Ltd.), Megafac F171, F173, F176, F189, F113, F110, F177, F120 and R08 (produced by Dainippon Ink & Chemicals, Inc.), Surflon S-382, SC101, 102, 103, 104, 105, 106 and KH-20 (produced by Asahi Glass Co., Ltd.), Troy Sol S-366 (produced by Troy Chemical Co., Ltd.), GF-300 and GF-150 (produced by TOAGOSEI CO., LTD.), Sarfron S-393 (produced by SEIMI CHEMICAL CO., LTD.), Eftop EF121, EF122A, EF122B, RF122C, EF125M, EF135M, EF351, EF352, EF801, EF802 and EF601 (produced by JEMCO INC.), PF636, PF656, PF6320 and PF6520 (produced by OMNOVA), and FTX-204G, 208G, 218G, 230G, 204D, 208D, 212D, 218D and 222D (produced by NEOS). Further, polysiloxane polymer KP-341 (produced by Shin-Etsu Chemical Co., Ltd.) can be employed as the siliconized surfactant.

As the surfactant, besides the above publicly known surfactants, use can be made of a surfactant based on a polymer containing a fluoroaliphatic group derived from a fluoroaliphatic compound produced by a telomerization technique (also known as a telomer process) or an oligomerization technique (also known as an oligomer process). The fluoroaliphatic compound can be synthesized by the process described in JP-A-2002-90991.

As the relevant surfactant, there can be mentioned Megafac F178, F-470, F-473, F-475, F-476 or F-472 (produced by Dainippon Ink & Chemicals, Inc.), a copolymer from an acrylate (or methacrylate) having a C$_6$F$_{13}$ group and poly(oxyalkylene) acrylate (or methacrylate), a copolymer from an acrylate (or methacrylate) having a C$_3$F$_7$ group, poly(oxyethylene) acrylate (or methacrylate) and poly(oxypropylene) acrylate (or methacrylate), or the like.

Moreover, in the present invention, use can be made of surfactants other than the fluorinated and/or siliconized surfactants, described in section [0280] of US Patent Application Publication No. 2008/0248425.

These surfactants may be used either individually or in combination.

It is optional for the actinic-ray- or radiation-sensitive resin composition of the present invention to contain a surfactant. When the actinic-ray- or radiation-sensitive resin composition contains a surfactant, the amount of surfactant used is preferably in the range of 0.0001 to 2 mass %, more preferably 0.0005 to 1 mass %, based on the total mass of the actinic-ray- or radiation-sensitive resin composition (excluding the solvent).

[6] Other additive (F)

It is optional for the actinic-ray- or radiation-sensitive resin composition of the present invention to contain a carboxylic acid onium salt. As the carboxylic acid onium salt, there can be mentioned any of those described in sections [0605] to [0606] of US Patent Application Publication No. 2008/0187860.

These carboxylic acid onium salts can be synthesized by reacting a sulfonium hydroxide, an iodonium hydroxide or an ammonium hydroxide and a carboxylic acid with silver oxide in an appropriate solvent.

When the actinic-ray- or radiation-sensitive resin composition contains a carboxylic acid onium salt, the content thereof is generally in the range of 0.1 to 20 mass %, preferably 0.5 to 10 mass % and further more preferably 1 to 7 mass %, based on the total solids of the composition.

According to necessity, the actinic-ray- or radiation-sensitive resin composition of the present invention may further contain a dye, a plasticizer, a photosensitizer, a light absorber, an alkali-soluble resin, a dissolution inhibitor, a compound capable of accelerating the dissolution in a developer (for example, a phenolic compound of 1000 or less molecular weight, or a carboxylated alicyclic or aliphatic compound), etc.

The above phenolic compound of 1000 or less molecular weight can be easily synthesized by persons of ordinary skill in the art to which the present invention pertains while consulting the processes described in, for example, JP-A's H4-122938 and H2-28531, U.S. Pat. No. 4,916,210 and EP 219294.

As the carboxylated alicyclic or aliphatic compound, there can be mentioned, for example, a carboxylic acid derivative of steroid structure such as cholic acid, deoxycholic acid or lithocholic acid, an adamantanecarboxylic acid derivative, adamantanedicarboxylic acid, cyclohexanecarboxylic acid, cyclohexanedicarboxylic acid or the like. These are however nonlimiting.

From the viewpoint of enhancing the resolving power, the actinic-ray- or radiation-sensitive resin composition of the present invention is preferably used with a film thickness of 30 to 250 nm. More preferably, the composition is used with a film thickness of 30 to 200 nm. This film thickness can be attained by setting the solid content of the composition within an appropriate range so as to cause the composition to have an appropriate viscosity, thereby improving the applicability and film forming property.

The solid concentration of the actinic-ray- or radiation-sensitive resin composition of the present invention is generally in the range of 1.0 to 15 mass %, preferably 2.5 to 13 mass % and more preferably 3.0 to 12 mass %. The resist solution can be uniformly applied onto substrates by regulating the solid concentration so as to fall within this range. Further, a resist pattern exhibiting a high resolution and a rectangular profile and excelling in etching resistance can be formed by the regulation. Although the reason therefor is not necessarily apparent, it is presumed that very possibly, the aggregation of materials, especially photoacid generators, in the resist solution can be inhibited by regulating the solid concentration so as to be 10 mass % or below, preferably 5.7 mass % or below, so that a uniform resist film can be formed.

The term "solid concentration" means the percentage of the weight of non-solvent resist components based on the total weight of the actinic-ray- or radiation-sensitive resin composition.

The actinic-ray- or radiation-sensitive resin composition of the present invention is used in such a manner that the above-mentioned components are dissolved in a given organic solvent, preferably the above-mentioned mixed solvent, and filtered and applied onto a given support (substrate). The filter medium for use in the filtration is preferably one made of a polytetrafluoroethylene, polyethylene or nylon that has a pore size of 0.1 µm or less, preferably 0.05 µm or less and more preferably 0.03 µm or less. In the filtration, as described in, for example, JP-A-2002-62667, a cyclic filtration may be carried out, or two or more types of filters may be connected in series or parallel. Moreover, the composition may be filtered two or more times. Further, the composition may be deaerated prior to or after the filtration.

[7] Method of Forming Pattern

The method of forming a pattern according to the present invention (negative pattern forming method) comprises at least the operations of:

(a) forming the actinic-ray- or radiation-sensitive resin composition into a film (actinic-ray- or radiation-sensitive film), (b) exposing the film to light, and (c) developing the exposed film with a developer comprising an organic solvent.

In the operation (b), the exposure may be a liquid-immersion exposure.

In the pattern forming method of the present invention, the exposing operation (b) is preferably followed by a baking operation (d).

The pattern forming method of the present invention may further comprise an operation of development using an alkali developer (e).

In the pattern forming method of the present invention, the exposing operation (b) can be conducted two or more times.

In the pattern forming method of the present invention, the baking operation (d) can be conducted two or more times.

The actinic-ray- or radiation-sensitive film is one formed from the above actinic-ray- or radiation-sensitive resin composition of the present invention. In particular, the film is preferably formed on a substrate. In the pattern forming method of the present invention, the operation of forming the film of the actinic-ray- or radiation-sensitive resin composition on a substrate, the operation of exposing the film to light, and the operation of developing the exposed film can be carried out using generally known techniques.

Preferably, the operation of prebake (PB) is performed after the film formation but prior to the exposing operation.

(d) rinsing the developed film with a rinse liquid containing an organic solvent.

Also preferably, an operation of post-exposure bake (PEB) is performed after the exposing operation but prior to the developing operation.

In both the PB operation and the PEB operation, the baking is preferably performed at 70 to 130° C., more preferably 80 to 120° C.

The baking time is preferably in the range of 30 to 300 seconds, more preferably 30 to 180 seconds and further more preferably 30 to 90 seconds.

The baking can be performed by means provided in the common exposure/development equipment. The baking can also be performed using a hot plate or the like.

The baking accelerates the reaction in exposed areas, so that the sensitivity and pattern profile can be enhanced.

With respect to the wavelength of the light source for use in the exposure equipment according to the present invention, there can be mentioned a KrF excimer laser (248 nm), an EUV (13 nm) or electron beams. A KrF excimer laser is preferred.

The substrate used for film formation in the present invention is not particularly limited. Use can be made of any of an inorganic substrate of silicon, SiN, $SiO_2$, TiN or the like, a coated inorganic substrate such as SOG and substrates commonly employed in a semiconductor production process for an IC or the like, a circuit board production process for a liquid crystal, a thermal head or the like and other photoapplication lithography processes. Further, according to necessity, an organic antireflection film may be provided between the film and the substrate.

For example, an antireflection film may be provided as an underlayer of the resist. As the antireflection film, use can be made of both an inorganic film of titanium, titanium dioxide, titanium nitride, chromium oxide, carbon, amorphous silicon or the like and an organic film comprised of a light absorber and a polymer material. The former film in the stage of film formation requires equipment, such as a vacuum vapor deposition apparatus, a CVD apparatus or a sputtering apparatus. As the organic antireflection film, there can be mentioned, for example, one comprised of a condensate of diphenylamine derivative and formaldehyde-modified melamine resin, an alkali-soluble resin and a light absorber as described in Jpn. Pat. Appln. KOKOKU Publication No. H7-69611; one comprised of a product of reaction between a maleic anhydride copolymer and a diamine light absorber as described in U.S. Pat. No. 5,294,680; one containing a resin binder and a methylolmelamine thermal crosslinking agent as described in JP-A-H6-118631; an acrylic resin antireflection film simultaneously having a carboxylic acid group, an epoxy group and a light absorbing group in each molecule thereof as described in JP-A-H6-118656; one comprised of a methylolmelamine and a benzophenone light absorber as described in JP-A-H8-87115; one obtained by adding a low-molecular light absorber to a polyvinyl alcohol resin as described in JP-A-H8-179509; or the like.

Also, as the organic antireflection film, use can be made of commercially available organic antireflection films, such as DUV30 Series and DUV40 Series produced by Brewer Science Inc. and AR-2, AR-3 and AR-5 produced by Shipley Co., Ltd.

Further, according to necessity, an antireflection film can be provided as an upper layer of the resist.

As the antireflection film, there can be mentioned, for example, AQUATAR-II, AQUATAR-III, AQUATAR-VII, etc. manufactured by AZ Electronic Materials Co., Ltd.

In the pattern forming method of the present invention, as the developer (hereinafter also referred to as an organic developer) for use in the operation of development with the developer comprising an organic solvent, use can be made of a polar solvent, such as a ketone solvent, an ester solvent, an alcohol solvent, an amide solvent or an ether solvent, and a hydrocarbon solvent.

As the ketone solvent, there can be mentioned, for example, 1-octanone, 2-octanone, 1-nonanone, 2-nonanone, acetone, 2-heptanone (methyl amyl ketone), 4-heptanone, 1-hexanone, 2-hexanone, diisobutyl ketone, cyclohexanone, methylcyclohexanone, phenylacetone, methyl ethyl ketone, methyl isobutyl ketone, acetylacetone, acetonylacetone, ionone, diacetonyl alcohol, acetyl carbinol, acetophenone, methyl naphthyl ketone, isophorone, propylene carbonate or the like.

As the ester solvent, there can be mentioned, for example, methyl acetate, butyl acetate, ethyl acetate, isopropyl acetate, pentyl acetate, isopentyl acetate, amyl acetate, propylene glycol monomethyl ether acetate, ethylene glycol monoethyl ether acetate, diethylene glycol monobutyl ether acetate, diethylene glycol monoethyl ether acetate, ethyl 3-ethoxypropionate, 3-methoxybutyl acetate, 3-methyl-3-methoxybutyl acetate, methyl formate, ethyl formate, butyl formate, propyl formate, ethyl lactate, butyl lactate, propyl lactate or the like.

As the alcohol solvent, there can be mentioned, for example, an alcohol, such as methyl alcohol, ethyl alcohol, n-propyl alcohol, isopropyl alcohol, n-butyl alcohol, sec-butyl alcohol, tert-butyl alcohol, isobutyl alcohol, n-hexyl alcohol, n-heptyl alcohol, n-octyl alcohol or n-decanol; a glycol solvent, such as ethylene glycol, diethylene glycol or triethylene glycol; a glycol ether solvent, such as ethylene glycol monomethyl ether, propylene glycol monomethyl ether, ethylene glycol monoethyl ether, propylene glycol monoethyl ether, diethylene glycol monoethyl ether, triethylene glycol monoethyl ether or methoxymethylbutanol; or the like.

As the ether solvent, there can be mentioned, for example, not only any of the above-mentioned glycol ether solvents but also dioxane, tetrahydrofuran or the like.

As the amide solvent, there can be mentioned, for example, N-methyl-2-pyrrolidone, N,N-dimethylacetamide, N,N-dimethylformamide, hexamethylphosphoric triamide, 1,3-dimethyl-2-imidazolidinone or the like.

As the hydrocarbon solvent, there can be mentioned, for example, an aromatic hydrocarbon solvent, such as toluene or xylene, or an aliphatic hydrocarbon solvent, such as pentane, hexane, octane or decane.

Two or more of these solvents may be mixed together before use. Alternatively, each of the solvents may be used in a mixture with a solvent other than those mentioned above or water. From the viewpoint of the fullest exertion of the effects of the present invention, it is preferred for the water content of the whole developer to be below 10 mass %. More preferably, the developer contains substantially no water.

Namely, the amount of organic solvent used in the organic developer is preferably in the range of 90 to 100 mass %, more preferably 95 to 100 mass %, based on the whole amount of the developer.

It is especially preferred for the organic developer to be one comprising at least one organic solvent selected from the group consisting of a ketone solvent, an ester solvent, an alcohol solvent, an amide solvent and an ether solvent.

The vapor pressure of the organic developer at 20° c. is preferably 5 kPa or below, more preferably 3 kPa or below and most preferably 2 kPa or below. When the vapor pressure of the organic developer is kPa or below, the evaporation of the developer on a substrate or in a development cup can be suppressed so that the temperature uniformity within the plane of the wafer can be enhanced to thereby improve the dimensional uniformity within the plane of the wafer.

As particular examples of the organic developers exhibiting a vapor pressure of 5 kPa or below, there can be mentioned a ketone solvent, such as 1-octanone, 2-octanone, 1-nonanone, 2-nonanone, 2-heptanone (methyl amyl ketone), 4-heptanone, 2-hexanone, diisobutyl ketone, cyclohexanone, methylcyclohexanone, phenylacetone or methyl isobutyl ketone; an ester solvent, such as butyl acetate, pentyl acetate, isopentyl acetate, amyl acetate, propylene glycol monomethyl ether acetate, ethylene glycol monoethyl ether acetate, diethylene glycol monobutyl ether acetate, diethylene glycol monoethyl ether acetate, ethyl 3-ethoxypropionate, 3-methoxybutyl acetate, 3-methyl-3-methoxybutyl acetate, butyl formate, propyl formate, ethyl lactate, butyl lactate or propyl lactate; an alcohol solvent, such as n-propyl alcohol, isopropyl alcohol, n-butyl alcohol, sec-butyl alcohol, tert-butyl alcohol, isobutyl alcohol, n-hexyl alcohol, n-heptyl alcohol, n-octyl alcohol or n-decanol; a glycol solvent, such as ethylene glycol, diethylene glycol or triethylene glycol; a glycol ether solvent, such as ethylene glycol monomethyl ether, propylene glycol monomethyl ether, ethylene glycol monoethyl ether, propylene glycol monoethyl ether, diethylene glycol monomethyl ether, triethylene glycol monoethyl ether or methoxymethylbutanol; an ether solvent, such as tetrahydrofuran; an amide solvent, such as N-methyl-2-pyrrolidone, N,N-dimethylacetamide or N,N-dimethylformamide; an aromatic hydrocarbon solvent, such as toluene or xylene, and an aliphatic hydrocarbon solvent, such as octane or decane.

As particular examples of the organic developers exhibiting a vapor pressure of 2 kPa or below as an especially preferred range, there can be mentioned ketone solvent, such as 1-octanone, 2-octanone, 1-nonanone, 2-nonanone, 4-heptanone, 2-hexanone, diisobutyl ketone, cyclohexanone, methylcyclohexanone or phenylacetone; an ester solvent, such as butyl acetate, amyl acetate, propylene glycol monomethyl ether acetate, ethylene glycol monoethyl ether acetate, diethylene glycol monobutyl ether acetate, diethylene glycol monoethyl ether acetate, ethyl 3-ethoxypropionate, 3-methoxybutyl acetate, 3-methyl-3-methoxybutyl acetate, ethyl lactate, butyl lactate or propyl lactate; an alcohol solvent, such as n-butyl alcohol, sec-butyl alcohol, tert-butyl alcohol, isobutyl alcohol, n-hexyl alcohol, n-heptyl alcohol, n-octyl alcohol or n-decanol; a glycol solvent, such as ethylene glycol, diethylene glycol or triethylene glycol; a glycol ether solvent, such as ethylene glycol monomethyl ether, propylene glycol monomethyl ether, ethylene glycol monoethyl ether, propylene glycol monoethyl ether, diethylene glycol monomethyl ether, triethylene glycol monoethyl ether or methoxymethylbutanol; an amide solvent, such as N-methyl-2-pyrrolidone, N,N-dimethylacetamide or N,N-dimethylformamide; an aromatic hydrocarbon solvent, such as xylene; and an aliphatic hydrocarbon solvent, such as octane or decane.

According to necessity, an appropriate amount of surfactant can be added to the organic developer.

The surfactant is not particularly limited. For example, use can be made of any of ionic and nonionic fluorinated and/or siliconized surfactants and the like. As such fluorinated and/or siliconized surfactants, there can be mentioned, for example, those described in JP-A's S62-36663, S61-226746, S61-226745, S62-170950, S63-34540, H7-230165, H8-62834, H9-54432 and H9-5988 and U.S. Pat. Nos. 5,405,720, 5,360,692, 5,529,881, 5,296,330, 5,436,098, 5,57,6143, 5,294,511 and 5,824,451. Nonionic surfactants are preferred. Although nonionic surfactants are not particularly limited, using a fluorinated surfactant or siliconized surfactant is more preferred.

The amount of surfactant added is generally in the range of 0.001 to 5 mass %, preferably 0.005 to 2 mass % and further more preferably 0.01 to 0.5 mass % based on the whole amount of the developer.

As the development method, use can be made of, for example, a method in which the substrate is dipped in a tank filled with a developer for a given period of time (dip method), a method in which a developer is puddled on the surface of the substrate by its surface tension and allowed to stand still for a given period of time to thereby effect development (puddle method), a method in which a developer is sprayed onto the surface of the substrate (spray method), or a method in which a developer is continuously discharged onto the substrate being rotated at a given speed while scanning a developer discharge nozzle at a given speed (dynamic dispense method).

With respect to the above various development methods, when the operation of discharging a developer toward a resist film through a development nozzle of a development apparatus is included, the discharge pressure of discharged developer (flow rate per area of discharged developer) is preferably 2 ml/sec/mm$^2$ or below, more preferably 1.5 ml/sec/mm$^2$ or below and further more preferably 1 ml/sec/mm$^2$ or below. There is no particular lower limit of the flow rate. However, from the viewpoint of through-put, it is preferred for the flow rate to be 0.2 ml/sec/mm$^2$ or higher.

Pattern defects attributed to any resist residue after development can be markedly reduced by regulating the discharge pressure of discharged developer so as to fall within the above range.

The detail of the mechanism thereof has not been elucidated. However, it is presumed that regulating the discharge pressure so as to fall within the above range would decrease the pressure of the developer on the resist film, thereby inhibiting any inadvertent shaving or crumbling of the resist film/resist pattern.

The discharge pressure of developer (ml/sec/mm$^2$) refers to a value exhibited at the outlet of the development nozzle of the development apparatus.

For the regulation of the discharge pressure of developer, there can be employed, for example, a method in which the discharge pressure is regulated by means of a pump or the like, or a method in which the discharge pressure is changed through pressure regulation by supply from a pressure tank.

The operation of developing with a developer comprising an organic solvent may be followed by the operation of discontinuing the development by replacement with another solvent.

The operation of developing with a developer comprising an organic solvent is preferably followed by the operation of rinsing the developed film with a rinse liquid.

The rinse liquid for use in the rinse operation after the operation of development with a developer comprising an organic solvent is not particularly limited as long as it does not dissolve the resist pattern, and solutions comprising common organic solvents can be used as the same. It is preferred for the rinse liquid to be one comprising at least one organic solvent selected from the group consisting of a hydrocarbon solvent, a ketone solvent, an ester solvent, an alcohol solvent, an amide solvent and an ether solvent.

Particular examples of the hydrocarbon solvent, ketone solvent, ester solvent, alcohol solvent, amide solvent and ether solvent are the same as set forth above in connection with the developer comprising an organic solvent.

The operation of developing with the developer comprising an organic solvent is preferably followed by the operation of rinsing with a rinse liquid comprising at least one organic solvent selected from the group consisting of a ketone solvent, an ester solvent, an alcohol solvent and an amide solvent; more preferably followed by the operation of rinsing with a rinse liquid comprising an alcohol solvent or an ester solvent; further more preferably followed by the operation of rinsing with a rinse liquid comprising a monohydric alcohol; and most preferably followed by the operation of rinsing with a rinse liquid comprising a monohydric alcohol having 5 or more carbon atoms.

As the monohydric alcohol for use in the rinse operation, there can be mentioned a linear, branched or cyclic monohydric alcohol. Particular examples thereof include 1-butanol, 2-butanol, 3-methyl-1-butanol, tert-butyl alcohol, 1-pentanol, 2-pentanol, 1-hexanol, 4-methyl-2-pentanol, 1-heptanol, 1-octanol, 2-hexanol, cyclopentanol, 2-heptanol, 2-octanol, 3-hexanol, 3-heptanol, 3-octanol and 4-octanol. Particular examples of the most preferred monohydric alcohols each having 5 or more carbon atoms include 1-hexanol, 2-hexanol, 4-methyl-2-pentanol, 1-pentanol and 3-methyl-1-butanol.

Two or more of these components may be mixed together before use. Also, they may be mixed with other organic solvents before use.

The water content of the rinse liquid is preferably 10 mass % or below, more preferably 5 mass % or below and most preferably 3 mass % or below. Favorable development performance can be attained by controlling the water content of the rinse liquid at 10 mass % or below.

With respect to the rinse liquid for use after the operation of developing with a developer comprising an organic solvent, the vapor pressure thereof at 20° C. is preferably in the range of 0.05 to 5 kPa, more preferably 0.1 to 5 kPa and most preferably 0.12 to 3 kPa. When the vapor pressure of the rinse liquid is in the range of 0.05 to 5 kPa, not only can the temperature uniformity within the plane of the wafer be enhanced but also the swell attributed to the penetration of the rinse liquid can be suppressed to thereby improve the dimensional uniformity within the plane of the wafer.

An appropriate amount of surfactant may be added to the rinse liquid before use.

In the rinse operation, the wafer having undergone the development with a developer comprising an organic solvent is rinsed with the above rinse liquid comprising an organic solvent. The method of rinse treatment is not particularly limited. For example, use can be made of any of a method in which the rinse liquid is continuously applied onto the substrate being rotated at a given speed (spin application method), a method in which the substrate is dipped in a tank filled with the rinse liquid for a given period of time (dip method) and a method in which the rinse liquid is sprayed onto the surface of the substrate (spray method). Preferably, the rinse treatment is carried out according to the spin application method, and thereafter the substrate is rotated at a rotating speed of 2000 to 4000 rpm to thereby remove the rinse liquid from the top of the substrate. Also, preferably, a baking operation (post-bake) is carried out subsequent to the rinse operation. Any inter-pattern and intra-pattern remaining developer and rinse liquid are removed by carrying out the bake. The bake operation subsequent to the rinse operation is generally performed at 40 to 160° C., preferably 70 to 95° C., for a period of 10 seconds to 3 minutes, preferably 30 to 90 seconds.

When the pattern forming method of the present invention further includes the operation of developing with an alkali developer, as the alkali developer, use can be made of, for example, any of alkaline aqueous solutions of an inorganic alkali such as sodium hydroxide, potassium hydroxide, sodium carbonate, sodium silicate, sodium metasilicate or aqueous ammonia, a primary amine such as ethylamine or n-propylamine, a secondary amine such as diethylamine or di-n-butylamine, a tertiary amine such as triethylamine or methyldiethylamine, an alcoholamine such as dimethylethanolamine or triethanolamine, a quaternary ammonium salt such as tetramethylammonium hydroxide or tetraethylammonium hydroxide, a cycloamine such as pyrrole or piperidine, and the like.

Appropriate amounts of an alcohol and a surfactant may be added to the above alkaline aqueous solutions before the use thereof.

The alkali concentration of the alkali developer is generally in the range of 0.1 to 20 mass %.

The pH value of the alkali developer is generally in the range of 10.0 to 15.0.

A 2.38 mass % aqueous tetramethylammonium hydroxide solution is particularly preferred.

Pure water is used as the rinse liquid for use in the rinse treatment after the alkali development. Before the use thereof, an appropriate amount of surfactant may be added thereto.

Further, the development operation or rinse operation may be followed by the operation of removing any portion of developer or rinse liquid adhering onto the pattern by use of a supercritical fluid.

Furthermore, the present invention relates to a process for manufacturing an electronic device in which the above-described pattern forming method of the present invention is included, and relates to an electronic device manufactured by the process.

The electronic device of the present invention can be appropriately mounted in electrical and electronic equipments (household electronic appliance, OA/media-related equipment, optical apparatus, telecommunication equipment and the like).

Example

The present invention will be described in greater detail below by way of its examples. However, the gist of the present invention is in no way limited to these examples.

(Preparation of Resist Composition)

Solutions each of 6 mass % solid content were prepared by using the individual components of Table 1 below. Each of the obtained solutions was passed through a polyethylene filter of 0.1 μm pore size. Thus, the intended resist compositions were obtained.

TABLE 1

| Resist | Resin (A) (mass ratio) | Compound (B) (mass %) | Basic compd. (D) (mass %) | Surfactant (mass %) | Solvent (ratio) |
|---|---|---|---|---|---|
| Res-01 | Pol-01 | PAG-1 (6.27) | Amine-1 (0.16) | W-4 (0.30) | A1/B1 (70/30) |
| Res-02 | Pol-02/Pol-10 (70/30) | PAG-5 (8.61) | Amine-3 (0.31) | W-2 (0.30) | A1/A3 (80/20) |
| Res-03 | Pol-03 | PAG-7 (6.40) | Amine-5 (0.22) | W-4 (0.30) | A1/A3 (60/40) |
| Res-04 | Pol-04/Pol-05 (80/20) | PAG-6/PAG-3 (4.07/6.7) | — | W-1 (0.30) | A1/B2 (70/30) |
| Res-05 | Pol-06 | PAG-8 (7.13) | Amine-4/Amine-5 (0.26/0.13) | W-3 (0.30) | A1/B1 (60/40) |
| Res-06 | Pol-07 | PAG-2 (6.89) | — | W-2 (0.30) | A1/A2 (80/20) |
| Res-07 | Pol-08 | PAG-4 (8.99) | Amine-6 (0.25) | — | A1/A3 (90/10) |
| Res-08 | Pol-09 | PAG-1 (5.31) | Amine-2 (0.31) | W-4 (0.30) | A1 (100) |
| Res-09 | Pol-09 | PAG-ref (6.64) | Amine-3 (0.38) | W-4 (0.30) | A1/B1 (60/40) |
| Res-10 | Pol-10 | PAG-4 (8.99) | Amine-1 (0.16) | W-4 (0.30) | A1 (100) |
| Res-11 | Pol-11 | PAG-6 (5.13) | Amine-4 (0.30) | W-1 (0.30) | A1/A3 (80/20) |

The designations appearing in Table 1 are as follows.

[Resin (A)]

Pol-1 to Pol-11 indicated in Table 2 below were used as acid-decomposable resins. In the table, Mw means the weight average molecular weight (polystyrene-equivalent) determined by GPO (solvent: THF) analysis, and Pd means the polydispersity index (Mw/Mn; in which Mn means the number average molecular weight (polystyrene-equivalent)).

TABLE 2

| Resin (A) | Unit 1 | Unit 2 | Unit 3 | Unit 4 | Composition ratio | Mw | Pd |
|---|---|---|---|---|---|---|---|
| Pol-01 | Unit 1-1 | Unit 2-4 | Unit 3-6 | — | 30/50/20 | 21400 | 1.9 |

TABLE 2-continued
| Resin (A) | Unit 1 | Unit 2 | Unit 3 | Unit 4 | Composition ratio | Mw | Pd |
|---|---|---|---|---|---|---|---|
| Pol-02 | Unit 1-3 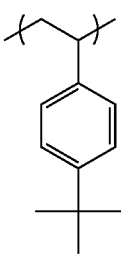 | Unit 2-1 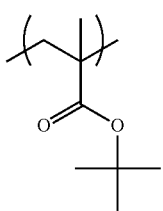 | Unit 3-1 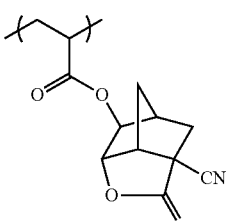 | — | 20/70/10 | 15300 | 1.6 |
| Pol-03 | Unit 1-5 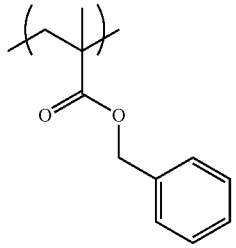 | Unit 2-1 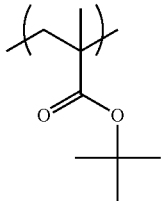 | Unit 3-2 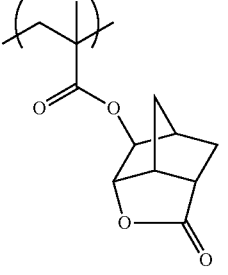 | Unit 3-6 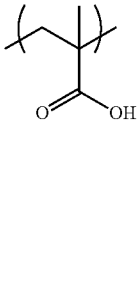 | 40/40/10/10 | 19600 | 2.0 |
| Pol-04 | Unit 1-6 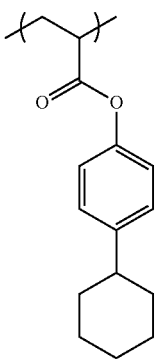 | Unit 2-2 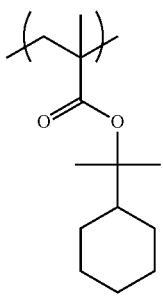 | Unit 1-2 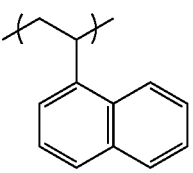 | | 40/50/10 | 31200 | 2.1 |
| Pol-05 | Unit 1-7 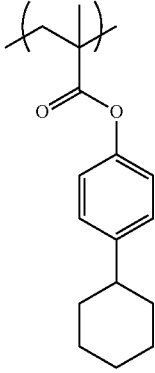 | Unit 2-5 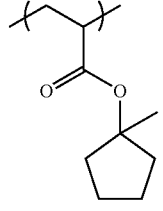 | Unit 3-4 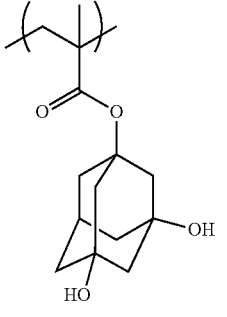 | Unit 1-13 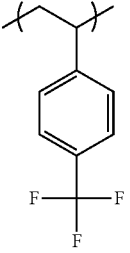 | 35/45/10/10 | 12300 | 1.7 |

TABLE 2-continued

| Resin (A) | Unit 1 | Unit 2 | Unit 3 | Unit 4 | Composition ratio | Mw | Pd |
|---|---|---|---|---|---|---|---|
| Pol-06 | Unit 1-8 | Unit 2-3 | Unit 3-3 | — | 20/60/20 | 22400 | 1.8 |
| Pol-07 | Unit 1-9 | Unit 2-6 | Unit 2-3 | Unit 3-7 | 20/40/20/20 | 17400 | 1.7 |
| Pol-08 | Unit 1-10 | Unit 2-7 | — | — | 40/60 | 14800 | 1.7 |
| Pol-09 | Unit 1-11 | Unit 2-4 | Unit 3-5 | — | 40/50/10 | 25400 | 1.8 |

TABLE 2-continued
| Resin (A) | Unit 1 | Unit 2 | Unit 3 | Unit 4 | Composition ratio | Mw | Pd |
|---|---|---|---|---|---|---|---|
| Pol-10 | Unit 1-14 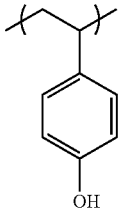 | Unit 2-5 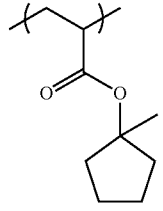 | Unit 3-2 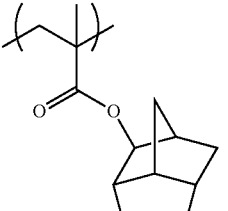 | — | 30/50/20 | 16100 | 1.7 |
| Pol-11 | Unit 3-1 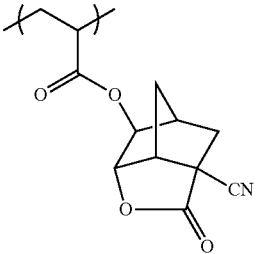 | Unit 2-2 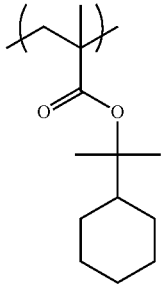 | Unit 3-6 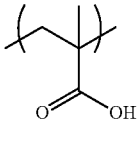 | — | 40/50/10 | 10700 | 1.7 |
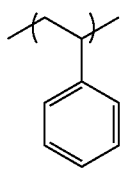
Unit 1-1
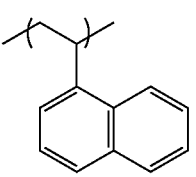
Unit 1-2
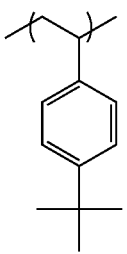
Unit 1-3
-continued
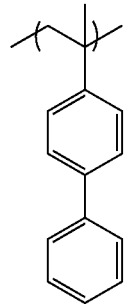
Unit 1-4
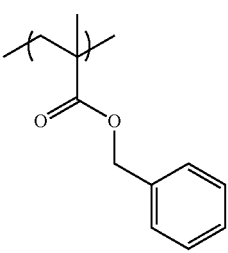
Unit 1-5

Unit 1-6
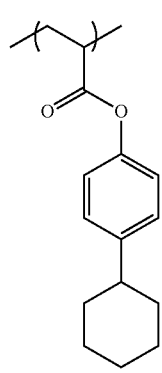
Unit 1-7
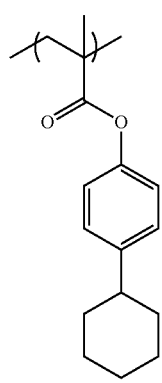
Unit 1-8
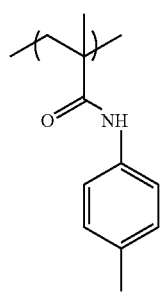
Unit 1-9
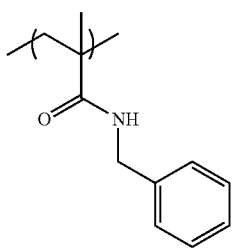
Unit 1-10
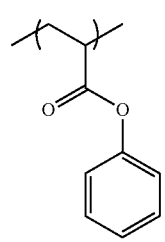
Unit 1-11
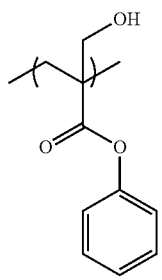
Unit 1-12
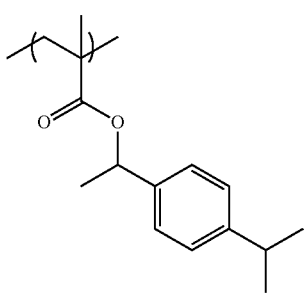
Unit 1-13
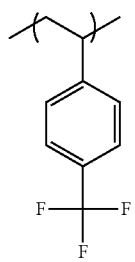
Unit 1-14
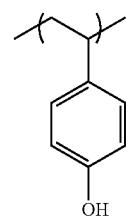
Unit 2-1
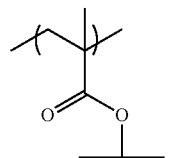
Unit 2-2
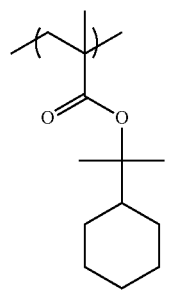

-continued
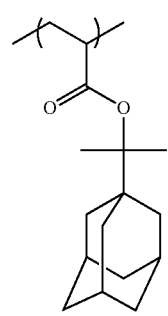
Unit 2-3
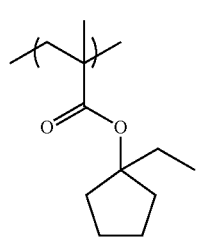
Unit 2-4
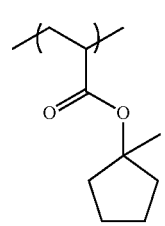
Unit 2-5
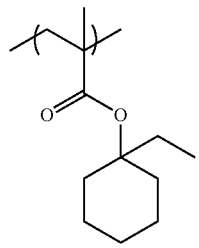
Unit 2-6
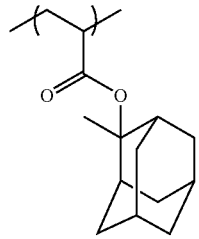
Unit 2-7
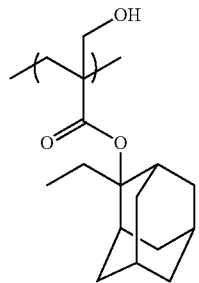
Unit 2-8
-continued
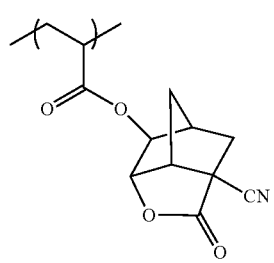
Unit 3-1
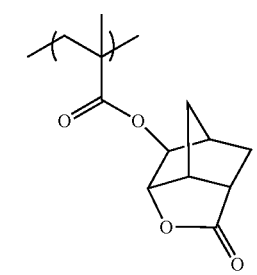
Unit 3-2
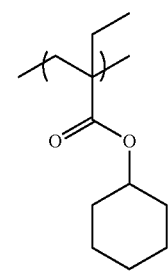
Unit 3-3
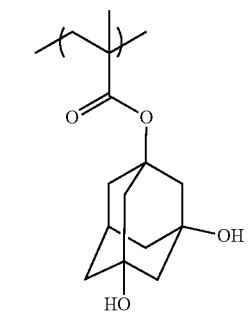
Unit 3-4
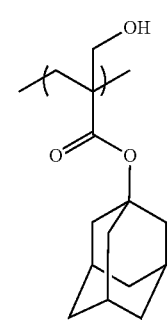
Unit 3-5
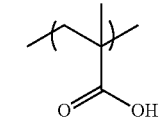
Unit 3-6

Unit 3-7
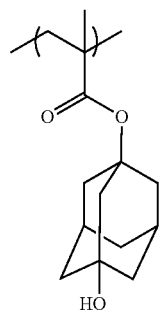
[Nonionic compound (B)]
PAG-1
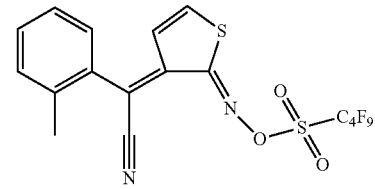
PAG-2
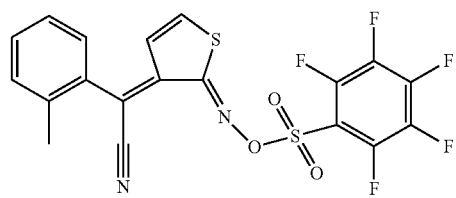
PAG-3
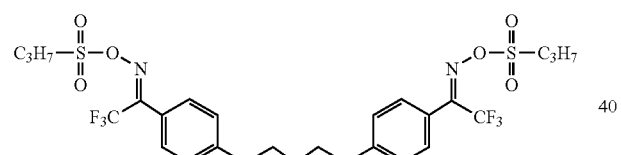
PAG-4
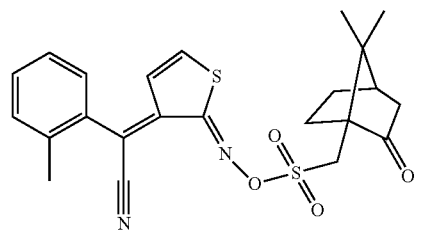
PAG-5
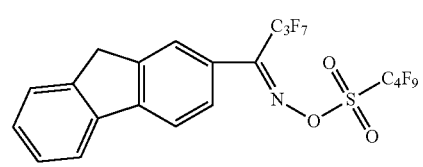
PAG-6
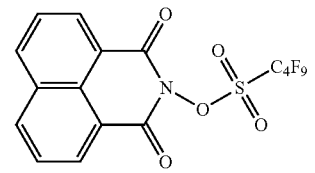
PAG-7
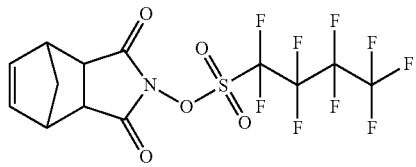
PAG-8
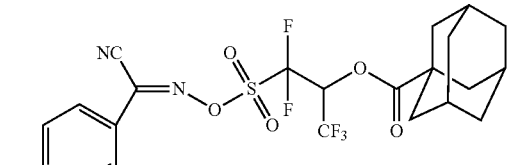
PAG-ref
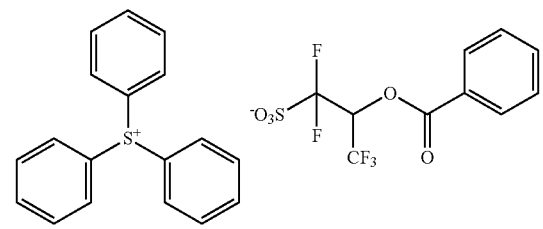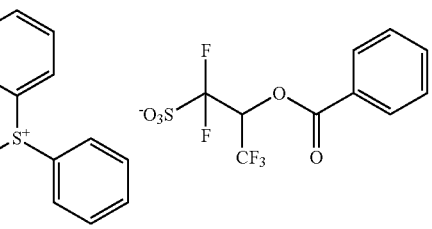
[Basic compound (D)]
Amine-1
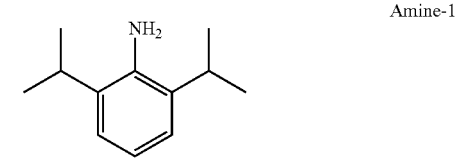
Amine-2
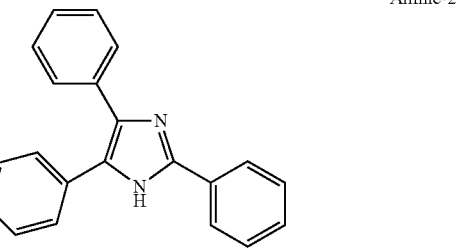
Amine-3
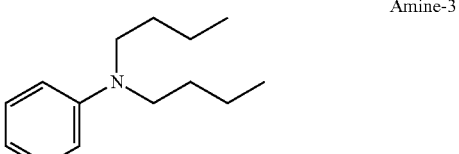
Amine-4
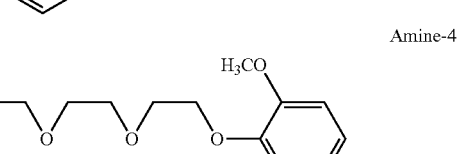
Amine-5
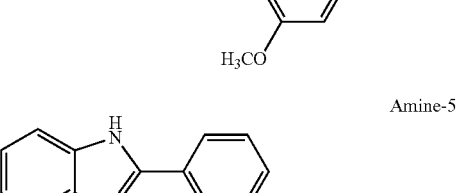

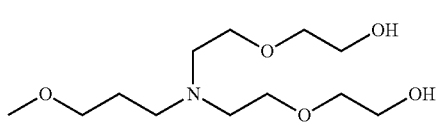

Amine-6

[Surfactant]

W-1: Megafac F176 (produced by Dainippon Ink & Chemicals, Inc.; fluorinated),

W-2: Megafac R08 (produced by Dainippon Ink & Chemicals, Inc.; fluorinated and siliconized), W-3: polysiloxane polymer KP-341 (produced by Shin-Etsu Chemical Co., Ltd.; siliconized), and W-4: compound of the formula below:

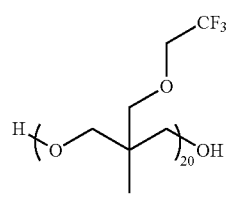

[Solvent]

A1: propylene glycol monomethyl ether acetate,
A2: γ-butyrolactone,
A3: cyclohexanone,
B1: propylene glycol monomethyl ether, and
B2: ethyl lactate.

<Evaluation>

With respect to each of the above obtained resist compositions, the resolution, residue defect and etching resistance were evaluated in accordance with the following evaluation methods. Results are given in Table 3.

[Resolution]

An organic antireflection film DUV44 (produced by Brewer Science Inc.) was applied onto a silicon wafer, thereby forming a 60 nm-thick antireflection film. Each of the above prepared resist compositions was applied thereonto and baked (prebaked, PB) for 60 seconds, thereby forming a 200 nm-thick resist film. The thus obtained wafer was patternwise exposed to light by means of a KrF excimer laser scanner (NA0.80). Thereafter, the exposed wafer was baked (post-exposure baked, PEB) for 60 seconds, and developed using a developer indicated in the following table for 30 seconds.

When no rinse treatment was performed, the wafer after the development was rotated at a rotating speed of 4000 rpm for 30 seconds. Thus, a line-and-space pattern was obtained. The minimum pitch in which an image was formed was denoted as a resolution.

When a rinse treatment was to be performed, the wafer after the development was rinsed with a rinse liquid indicated in the following table and rotated at a rotating speed of 4000 rpm for 30 seconds. Thus, a line-and-space pattern was obtained. The minimum pitch in which an image was formed was denoted as a resolution.

[Residue Defect]

An organic antireflection film DUV44 (produced by Brewer Science Inc.) was applied onto a silicon wafer, thereby forming a 60 nm-thick antireflection film. Each of the above prepared resist compositions was applied thereonto and baked (prebaked, PB) for 60 seconds, thereby forming a 200 nm-thick resist film. The thus obtained wafer was patternwise exposed to light by means of a KrF excimer laser scanner (NA0.80). Thereafter, the exposed wafer was baked (post-exposure baked, PEB) for 60 seconds, developed with a developer for 30 seconds, and rinsed with a rinse liquid. The rinsed wafer was rotated at a rotating speed of 4000 rpm for 30 seconds. Thus, a line-and-space pattern of 180 nm half pitch was obtained. Any residue defects on the thus obtained pattern were numerically rated, thereby identifying the number of residue defects per 8-inch silicon wafer, and evaluated as follows.

A: 0 to 50 defects,
B: 51 to 100 defects,
C: 101 to 150 defects, and
D: 151 or more defects.

[Etching Resistance]

Each of the above prepared resist compositions was applied onto a silicon wafer and baked (prebaked, PB) for 60 seconds, thereby forming a 100 nm-thick resist film. The whole surface of the obtained resist film was exposed to light by means of a KrF excimer laser scanner (NA0.80). Thereafter, the exposed resist film was developed with a negative developer for 30 seconds, and rinsed with a rinse liquid. The thus obtained wafer was rotated at a rotating speed of 4000 rpm for 30 seconds, thereby obtaining an exposed film. The resultant exposed film was etched for 30 seconds by means of an etching apparatus (model M-6000 manufactured by Hitachi High-Technologies Corporation). Any difference between the film thickness before the etching and that after the etching was measured, thereby determining the etching rate per second. Obtained results were evaluated as follows.

A: 0.70 to less than 0.85 nm/sec,
B: 0.85 to less than 0.95 nm/sec,
C: 0.95 to less than 1.05 nm/sec, and
D: 1.05 nm/sec or greater.

TABLE 3

| Ex. | Resist | PB | PEB | Developer | Rinse liquid | Resolution | Residue defect | Etching resistance |
|---|---|---|---|---|---|---|---|---|
| Ex. 1 (KrF-01) | Res-01 | 100° C./60 s | 120° C./60 s | S-1 | — | 120 nm | B | C |
| Ex. 2 (KrF-02) | Res-02 | 110° C./60 s | 120° C./60 s | S-2 | S-6 | 115 nm | A | C |
| Ex. 3 (KrF-03) | Res-03 | 110° C./60 s | 110° C./60 s | S-2 | S-5 | 110 nm | A | A |
| Ex. 4 (KrF-04) | Res-04 | 100° C./60 s | 100° C./60 s | S-1 | S-5 | 110 nm | B | A |
| Ex. 5 (KrF-05) | Res-05 | 90° C./60 s | 110° C./60 s | S-1 | S-7 | 120 nm | A | B |
| Ex. 6 (KrF-06) | Res-06 | 100° C./60 s | 120° C./60 s | S-1 | S-8 | 115 nm | B | B |
| Ex. 7 (KrF-07) | Res-07 | 100° C./60 s | 120° C./60 s | S-1 | S-3 | 125 nm | A | C |
| Ex. 8 (KrF-08) | Res-08 | 110° C./60 s | 100° C./60 s | S-2 | S-4 | 110 nm | A | B |
| Ex. 9 (KrF-09) | Res-10 | 100° C./60 s | 120° C./60 s | S-1 | S-4 | 130 nm | C | B |
| Comp. Ex. 1 (KrF-10) | Res-09 | 100° C./60 s | 110° C./60 s | S-1 | S-5 | 140 nm | D | B |
| Comp. Ex. 2 (KrF-11) | Res-11 | 100° C./60 s | 100° C./60 s | S-1 | S-5 | 150 nm | C | D |

The designations appearing in Table 3 are as follows.
[Developer and Rinse Liquid]
S-1: butyl acetate,
S-2: pentyl acetate,
S-3: anisole,
S-4: 1-hexanol,
S-5: 4-methyl-2-pentanol,
S-6: decane,
S-7: octane, and
S-8: 1-hexanol.

It is apparent from the favorable resist-pattern-forming performance exhibited in the above results that the pattern forming method of the present invention can be appropriately used in the process for manufacturing a semiconductor.

What is claimed is:

1. A method of forming a pattern, comprising;
    forming an actinic-ray- or radiation-sensitive resin composition into a film, the actinic-ray- or radiation-sensitive resin composition comprising;
        a resin (A) comprising a repeating unit containing a group that when acted on by an acid, is decomposed to thereby produce a polar group and comprising an aromatic group, which resin when acted on by an acid, decreases its solubility in an organic solvent,
        a nonionic compound (B) that when exposed to actinic rays or radiation, generates an acid, and
        a solvent (C);
    exposing the film to a KrF light; and
    developing the exposed film with a developer comprising an organic solvent to thereby form a negative pattern,
    wherein the nonionic compound (B) is expressed by general formula (B1) or (B2) below,

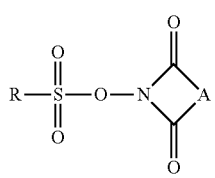

(B1)

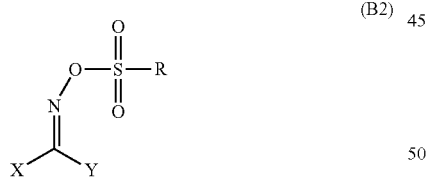

(B2)

in general formula (B1),
R represents an organic group, and
A represents an alkylene group, a cycloalkylene group, an alkenylene group, a cycloalkenylene group or an arylene group; and
in general formula (B2),
R represents an organic group, and
each of X and Y independently represents an alkyl group, a cycloalkyl group, an aryl group, a cyano group or a nitro group, provided that X and Y may be bonded to each other to thereby form a ring,
provided that X or Y of any of compounds of general formula (B2) may be bonded to X or Y of any of other compounds of general formula (B2) via a connecting group or a single bond.

2. The method according to claim 1, wherein the repeating unit containing a group that when acted on by an acid, is decomposed to thereby produce a polar group, contained in the resin (A) is expressed by general formula (I) below,

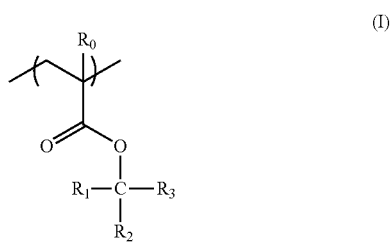

(I)

in which
$R_0$ represents a hydrogen atom or a linear or branched alkyl group optionally substituted with a fluorine atom or a hydroxyl group, and
each of $R_1$, $R_2$ and $R_3$ independently represents an optionally substituted linear or branched alkyl group or an optionally substituted cycloalkyl group, provided that any two of $R_1$, $R_2$ and $R_3$ may be bonded to each other to thereby form a monocyclic or polycyclic structure.

3. The method according to claim 1, wherein a repeating unit containing the aromatic group contained in the resin (A) is expressed by general formula (II) below,

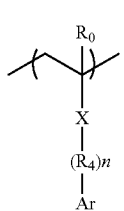

(II)

in which
$R_0$ represents a hydrogen atom or a linear or branched alkyl group optionally substituted with a fluorine atom or a hydroxyl group,
X represents a single bond or a bivalent connecting group,
Ar represents an optionally substituted aromatic group, provided that when a substituent is introduced in the aromatic group, the substituent is any of an alkyl group (optionally substituted), a cycloalkyl group (optionally substituted), an aryl group, a halogen atom, a cyano group, an amino group, a nitro group and a carboxyl group,
$R_4$ represents an optionally substituted alkylene group, and
n is an integer of 0 to 4.

4. The method according to claim 3, wherein in general formula (II), X is —COO— or —CONH—.

5. The method according to claim 1, wherein any of repeating units of general formula (III) below is contained in the resin (A) in an amount of up to 20 mol % based on all the repeating units of the resin (A),

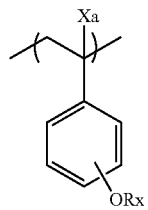

in which
Xa represents a hydrogen atom or a linear or branched alkyl group, and
Rx represents a hydrogen atom or a group that when acted on by an acid, is decomposed to thereby be cleaved.

6. The method according to claim 1, wherein the resin (A) contains neither any aromatic group containing a phenolic hydroxyl group nor any aromatic group containing a phenolic hydroxyl group whose hydrogen atom is replaced by a group that when acted on by an acid, is decomposed to thereby be cleaved.

7. The method according to claim 1, wherein the developer is a developer comprising at least one organic solvent selected from among a ketone solvent, an ester solvent, an alcohol solvent, an amide solvent and an ether solvent.

8. An actinic-ray- or radiation-sensitive resin composition for use in the method according to claim 1.

9. The actinic-ray- or radiation-sensitive resin composition according to claim 8, comprising a resin (A) comprising a repeating unit containing a group that when acted on by an acid, is decomposed to thereby produce a polar group and comprising an aromatic group, which resin when acted on by an acid, decreases its solubility in an organic solvent, a non-ionic compound (B) that when exposed to actinic rays or radiation, generates an acid and a solvent (C).

10. The actinic-ray- or radiation-sensitive resin composition according to claim 8, wherein the repeating unit containing a group that when acted on by an acid, is decomposed to thereby produce a polar group, contained in the resin (A) is expressed by general formula (I) below,

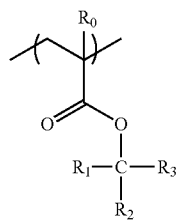

in which
$R_0$ represents a hydrogen atom or a linear or branched alkyl group optionally substituted with a fluorine atom or a hydroxyl group, and
each of $R_1$, $R_2$ and $R_3$ independently represents an optionally substituted linear or branched alkyl group or an optionally substituted cycloalkyl group, provided that any two of $R_1$, $R_2$ and $R_3$ may be bonded to each other to thereby form a monocyclic or polycyclic structure.

11. The actinic-ray- or radiation-sensitive resin composition according to claim 8, wherein a repeating unit containing the aromatic group contained in the resin (A) is expressed by general formula (II) below,

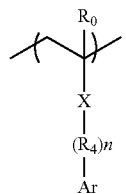

in which
$R_0$ represents a hydrogen atom or a linear or branched alkyl group optionally substituted with a fluorine atom or a hydroxyl group,
X represents a single bond or a bivalent connecting group,
Ar represents an optionally substituted aromatic group, provided that when a substituent is introduced in the aromatic group, the substituent is any of an alkyl group (optionally substituted), a cycloalkyl group (optionally substituted), an aryl group, a halogen atom, a cyano group, an amino group, a nitro group and a carboxyl group,
$R_4$ represents an optionally substituted alkylene group, and
n is an integer of 0 to 4.

12. The actinic-ray- or radiation-sensitive resin composition according to claim 11, wherein in general formula (II), X is —COO— or —CONH—.

13. The actinic-ray- or radiation-sensitive resin composition according to claim 8, wherein the content of any of repeating units of general formula (III) below contained in the resin (A) is up to 20 mol % based on all the repeating units of the resin (A),

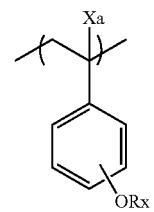

in which
Xa represents a hydrogen atom or a linear or branched alkyl group, and
Rx represents a hydrogen atom or a group that when acted on by an acid, is decomposed to thereby be cleaved.

14. The actinic-ray- or radiation-sensitive resin composition according to claim 8, wherein the resin (A) contains neither any aromatic group containing a phenolic hydroxyl group nor any aromatic group containing a phenolic hydroxyl group whose hydrogen atom is replaced by a group that when acted on by an acid, is decomposed to thereby be cleaved.

15. An actinic-ray- or radiation-sensitive film formed from the actinic-ray- or radiation-sensitive resin composition according to claim 8.

16. A process for manufacturing a semiconductor device, comprising the method according to claim 1.

17. A semiconductor device manufactured by the process of claim 16.

18. The actinic-ray- or radiation-sensitive resin composition according to claim 11, wherein X represents a single bond and/or n is an integer of 1 to 4.

* * * * *